(12) United States Patent
Cyrankowski et al.

(10) Patent No.: US 9,472,374 B2
(45) Date of Patent: Oct. 18, 2016

(54) TESTING ASSEMBLY INCLUDING A MULTIPLE DEGREE OF FREEDOM STAGE

(71) Applicant: Hysitron, Inc., Eden Prairie, MN (US)

(72) Inventors: Edward Cyrankowski, Woodbury, MN (US); Syed Amanulla Syed Asif, Bloomington, MN (US); Ryan Major, Crystal, MN (US); Derek Rasugu, Shakopee, MN (US); Yuxin Feng, Plymouth, MN (US)

(73) Assignee: HYSITRON, INC., Eden Prairie, MN (US)

( * ) Notice: Subject to any disclaimer, the term of this patent is extended or adjusted under 35 U.S.C. 154(b) by 0 days.

(21) Appl. No.: 14/347,173

(22) PCT Filed: Sep. 28, 2012

(86) PCT No.: PCT/US2012/058019
§ 371 (c)(1),
(2) Date: Mar. 25, 2014

(87) PCT Pub. No.: WO2013/049641
PCT Pub. Date: Apr. 4, 2013

(65) Prior Publication Data
US 2014/0231670 A1   Aug. 21, 2014

Related U.S. Application Data

(60) Provisional application No. 61/540,317, filed on Sep. 28, 2011.

(51) Int. Cl.
*H01J 37/20* (2006.01)
*G02B 21/26* (2006.01)
(Continued)

(52) U.S. Cl.
CPC .............. *H01J 37/20* (2013.01); *G01N 3/04* (2013.01); *G01N 3/42* (2013.01); *G02B 21/26* (2013.01);
(Continued)

(58) Field of Classification Search
CPC ................ G01N 21/13; H01J 37/20
USPC ..................... 250/442.11; 359/392, 384
See application file for complete search history.

(56) References Cited

U.S. PATENT DOCUMENTS

| 5,103,095 A | 4/1992 | Elings et al. |
| 5,227,626 A | 7/1993 | Okada et al. |

(Continued)

FOREIGN PATENT DOCUMENTS

| JP | 60136143 A | 7/1985 |
| JP | 01311550 A | 12/1989 |

(Continued)

OTHER PUBLICATIONS

"Japanese Application Serial No. 2014-533420, Office Action mailed Sep. 2, 2014", With English Translation, 11 pgs.
(Continued)

*Primary Examiner* — Jack Berman
*Assistant Examiner* — Kevin Chung
(74) *Attorney, Agent, or Firm* — Schwegman Lundberg & Woessner, P.A.

(57) ABSTRACT

A multiple degree of freedom sample stage or testing assembly including a multiple degree of freedom sample stage. The multiple degree of freedom sample stage includes a plurality of stages including linear, and one or more of rotation or tilt stages configured to position a sample in a plurality of orientations for access or observation by multiple instruments in a clustered volume that confines movement of the multiple degree of freedom sample stage. The multiple degree of freedom sample stage includes one or more clamping assemblies to statically hold the sample in place throughout observation and with the application of force to the sample, for instance by a mechanical testing instrument. Further, the multiple degree of freedom sample stage includes one or more cross roller bearing assemblies that substantially eliminate mechanical tolerance between elements of one or more stages in directions orthogonal to a moving axis of the respective stages.

20 Claims, 20 Drawing Sheets

(51) Int. Cl.
*G02B 21/32* (2006.01)
*G21K 5/10* (2006.01)
*G01N 3/04* (2006.01)
*G01N 3/42* (2006.01)

(52) U.S. Cl.
CPC ............... *G02B 21/32* (2013.01); *G21K 5/10* (2013.01); *G01N 2203/0026* (2013.01); *G01N 2203/0206* (2013.01); *H01J 2237/202* (2013.01); *H01J 2237/2062* (2013.01); *H01J 2237/28* (2013.01)

(56) References Cited

U.S. PATENT DOCUMENTS

| | | | |
|---|---|---|---|
| 5,412,597 | A | 5/1995 | Miyazaki et al. |
| 5,559,329 | A | 9/1996 | Joseph et al. |
| 6,058,592 | A | 5/2000 | Cadwallader et al. |
| 6,403,968 | B1 | 6/2002 | Hazaki et al. |
| 6,538,254 | B1* | 3/2003 | Tomimatsu et al. ...... 250/442.11 |
| 6,583,411 | B1 | 6/2003 | Altmann et al. |
| 8,008,633 | B2 | 8/2011 | Fujiyoshi et al. |
| 2003/0094583 | A1 | 5/2003 | Jang et al. |
| 2005/0139781 | A1* | 6/2005 | Hazaki ................. G01N 23/225 250/442.11 |
| 2007/0023684 | A1* | 2/2007 | Lewis et al. ............. 250/442.11 |
| 2007/0045537 | A1* | 3/2007 | Joseph ................. B81C 99/003 250/310 |
| 2010/0017920 | A1* | 1/2010 | Park ....................... B82Y 35/00 850/1 |
| 2010/0108884 | A1 | 5/2010 | Lou et al. |

FOREIGN PATENT DOCUMENTS

| | | |
|---|---|---|
| JP | 2000097836 A | 4/2000 |
| JP | 2000221409 A | 8/2000 |
| JP | 2004104001 A | 4/2004 |
| JP | 2005286164 A | 10/2005 |
| JP | 2008046324 A | 2/2008 |
| JP | 2008305679 A | 12/2008 |
| JP | 2010128360 A | 6/2010 |
| JP | 2010181339 A | 8/2010 |
| WO | WO-2013049641 A1 | 4/2013 |

OTHER PUBLICATIONS

"International Application Serial No. PCT/US2012/058019, International Preliminary Report on Patentability mailed Feb. 18, 2014", 4 pgs.

"International Application Serial No. PCT/US2012/058019, International Search Report mailed Mar. 11, 2013", 4 pgs.

"International Application Serial No. PCT/US2012/058019, Invitation to Pay Additional Fees and Partial Search Report mailed Dec. 3, 2012", 2 pgs.

"International Application Serial No. PCT/US2012/058019, Written Opinion mailed Jan. 3, 2014", 13 pgs.

"International Application Serial No. PCT/US2012/058019, Written Opinion mailed Mar. 11, 2013", 14 pgs.

Yamaguchi, Naoki, "When to choose crossed roller bearings", Retrieved from online<http://www.designworldonline.com/when-to-choose-crossed-roller-bearings/>, (May 17, 2010), 5 pgs.

"Japanese Application Serial No. 2014-533420, Notice of Rejection of Grounds mailed Jan. 6, 2015", 7 pgs.

"European Application Serial No. 12835945.2, Extended European Search Report mailed Oct. 13, 2015", 9 pgs.

European Application Serial No. 12835945.2, Extended European Search Report mailed Mar. 17, 2016, 21 pgs.

\* cited by examiner

TESTING ASSEMBLY INCLUDING A MULTIPLE DEGREE OF FREEDOM STAGE

RELATED APPLICATIONS

This patent application is a U.S. National Stage Filing from International Patent Application Serial No. PCT/US2012/058019, filed Sep. 28, 2012 and published on Apr. 4, 2013 as WO 2013/049641, which claims the benefit of priority to U.S. Provisional Patent Application Ser. No. 61/540,317, filed on Sep. 28, 2011, the contents of which applications are incorporated herein by reference in their entirety.

TECHNICAL FIELD

This document pertains generally, but not by way of limitation, to assemblies for and methods of mechanically testing samples at a micron or lower scale.

BACKGROUND

Instrument housing chambers, for instance, a chamber of a scanning electron microscope (SEM), optical microscope, transmission electron microscope or other multi-instrument assembly contains a plurality of instruments and detectors tightly clustered around and directed toward a centralized location near a sample stage. The centralized location is small and limits access to the sample, for instance by mechanical testing instruments installed within the chamber.

In one example, a mechanical testing instrument is installed within an access orifice of the instrument housing chamber. The mechanical testing instrument is affirmatively coupled with the instrument housing wall and extends from the wall toward the centralized location in a limited or single orientation (e.g., at static installation angle relative to the sample stage). The mechanical testing instrument extending from the wall to the centralized location consumes valuable space in the instrument housing chamber. A sample in the instrument housing chamber must be oriented toward the instrument to facilitate mechanical testing. For instance, the sample stage must orient the sample at an angle complementary to the installation angle. Because the installation angle relative to the sample stage is acute, obtuse or the like it is difficult to accurately position the sample for mechanical testing without time consuming and difficult actuation of the sample stage into awkward orientations. Moreover, the orientation of the sample may be at a less than ideal angle (e.g., non-orthogonal) and frustrate the accuracy of mechanical testing through indentation or scratching. Further still, the extension of the mechanical testing instrument from the wall consumes valuable space otherwise available for instruments, electronics and the like within the instrument housing chamber. Moreover, decoupling of the sample from the mechanical test instrument creates a large mechanical loop that extends through the instrument housing wall which may add to uncertainty and error during quantitative mechanical testing.

In another example, a testing assembly including a mechanical testing instrument and a stage is coupled with the sample stage of the instrument housing chamber. The stages of these testing assemblies provide limited (e.g., linear) orientation of the sample relative to the mechanical testing instrument and the cluster of instruments and detectors of the instrument chamber housing. The orientation flexibility of the sample is limited by the compact chamber of the instrument housing as well as the instruments and detectors clustered around the centralized location of the instrument housing sample stage. Further, mechanical testing may be performed and then the sample must be reoriented for examination or further work by the instruments and detectors of the instrument chamber housing.

Additionally, the provision of linear stages adds tolerance to the stage carrying the sample and correspondingly frustrates the accurate positioning of the sample including micron or smaller testing locations of interest relative to instruments. Tolerance is required to facilitate motion between portions of the stages, and with each degree of freedom the tolerance of the stage is compounded. Moreover, through mechanical testing the sample and the stage experience forces, moments and the like that can undesirably move the sample because of tolerances and further frustrate the accuracy of measurements and the observation of a micron or smaller testing location of interest.

OVERVIEW

The inventors have recognized, among other things, that a problem to be solved can include the positioning of a sample for observation and mechanical interaction and testing within a compact chamber of an instrument housing, such as a scanning electron microscope (SEM). The chamber of such an instrument housing includes a series of instruments and detectors (e.g., FIB instruments, one or more electron back scatter detectors (EBSD), an electron gun for an SEM and the like) clustered around a centralized testing location as well as the physical boundaries of the instrument housing walls. To make full use of all or a subset of the instruments and detectors within the instrument housing a sample must be oriented and positioned within the compact chamber according to the testing parameters of the instruments and detectors (e.g., focal points, working distances, and cooperative positioning needs of two or more instruments such as an electron gun and an EBSD). The orientation and position of the sample for each instrument and detector must be within the centralized location and not result in impingement or collision of the sample or a stage with any of the clustered instruments or detectors surrounding the centralized testing location (e.g., a localized coincidence region including a plurality of working regions of one or more instruments).

In an example, the present subject matter can provide a solution to this problem, such as by the provision of a testing assembly incorporating a multiple degree of freedom sample stage. In one example, the testing assembly is coupled with the existing sample stage of the instrument housing (e.g., the sample stage of an SEM). The testing assembly uses a multiple degree of freedom sample stage including linear, rotation and tilt stages to accurately, reliably and quickly position and reposition a sample within the chamber according to the testing parameters (e.g., working regions, such as focal points, instrument ranges and the like) of each of the instruments used successively or at the same time. Further, the positioning and orienting of the sample occurs within the centralized location (localized coincidence region) of the compact chamber surrounded by the clustered instruments and the detectors. The combination of rotation, tilt and linear positioning facilitates the orienting and positioning of a sample at the centralized location according to the working regions of the one or more instruments. Moreover, the positioning and repositioning of the sample is performed without opening of the chamber and manual repositioning.

In another example, the testing assembly includes one or more stages coupled with a mechanical testing instrument (e.g., a transducer including an indentation or scratch probe, tensile grips or the like) to provide at least one additional degree of freedom to the testing assembly. For instance, a sample that is tilted and rotated to direct the sample toward a first instrument is retained in close proximity to the centralized location of the compact chamber defined by the focal points or working distances (e.g., the working regions) of the one or more instruments and detectors as well as their physical housings. The mechanical testing instrument is similarly positionable relative to the sample to mechanically test the sample. The testing assembly thereby positions and orients the sample according to the parameters of each of the instruments originally present within the compact chamber of the instrument housing while at the same time positioning a mechanical testing instrument to interact with the sample. Moving the mechanical testing instrument maintains the sample in the desired orientation of the instruments and detectors, allows for their use and also allows for contemporaneous mechanical testing of the sample.

As described herein, the multiple degree of freedom sample stage (and in some examples the mechanical testing instrument) allows for the positioning and orienting of a sample within a centralized location (e.g., localized coincidence region) of the compact chamber and substantially prevents impingement or collision of the multiple degree of freedom sample stage with the instruments and detectors tightly clustered around the centralized location.

Another problem to be solved can include the tolerance of the various stages used to position and orient a sample within the centralized location of the instrument housing. Because the instruments, detectors and the mechanical testing instrument test at micron or smaller locations on the sample even minor tolerance in the stages can move a sample location of interest out of alignment for testing or observation. When compounded with multiple stages providing multiple degrees of freedom, the tolerance of each of the stages can further enhance the inaccuracy of the sample location positioning and orientation. Furthermore, mechanical testing of the sample by indenting, scratching and the like can impermissibly move the sample out of alignment with one or more of the instruments or detectors because of tolerance in the stages or a failure to affirmatively lock one or more of the stages in place prior to mechanical testing. Excessive compliance in the stages adds to uncertainty in mechanical measurements and further frustrates the ability to extract quantitative mechanical data from the testing.

In another example, the disclosed subject matter can provide a solution to this problem, such as by the provision of cross roller bearing assemblies for one or more linear stages that provide a solid structural interface between each stage and stage base. The surface to surface engagement between the cylindrical bearing surfaces and the opposed interface surfaces substantially eliminates relative movement of the components of each linear stage along axes not coincident with the linear axes of the respective stages. Additionally, one or more of the rotation and tilt stages includes clamping assemblies that affirmatively hold the stage of each actuator static relative to the respective stage base. The clamping assemblies bias the stage into engagement with the stage base with multiple points of contact to tightly hold the stage in the desired position. Even with engagement by the mechanical testing instrument with the sample (e.g., indenting, scratching and the like) and corresponding transmission of forces to the multiple degree of freedom sample stage, the sample is reliably held in the desired position and orientation for testing and observation. The multiple degree of freedom stage is thereby able to provide the flexibility of the linear, tilt and rotation positioning without the compounded tolerances provided in other multiple degree of freedom assemblies.

This overview is intended to provide an overview of subject matter of the disclosure. It is not intended to provide an exclusive or exhaustive explanation of the disclosure. The detailed description is included to provide further information about the disclosure.

BRIEF DESCRIPTION OF THE DRAWINGS

In the drawings, which are not necessarily drawn to scale, like numerals may describe similar components in different views. The drawings illustrate generally, by way of example, but not by way of limitation, various embodiments of the disclosure.

DETAILED DESCRIPTION

Figure 1:
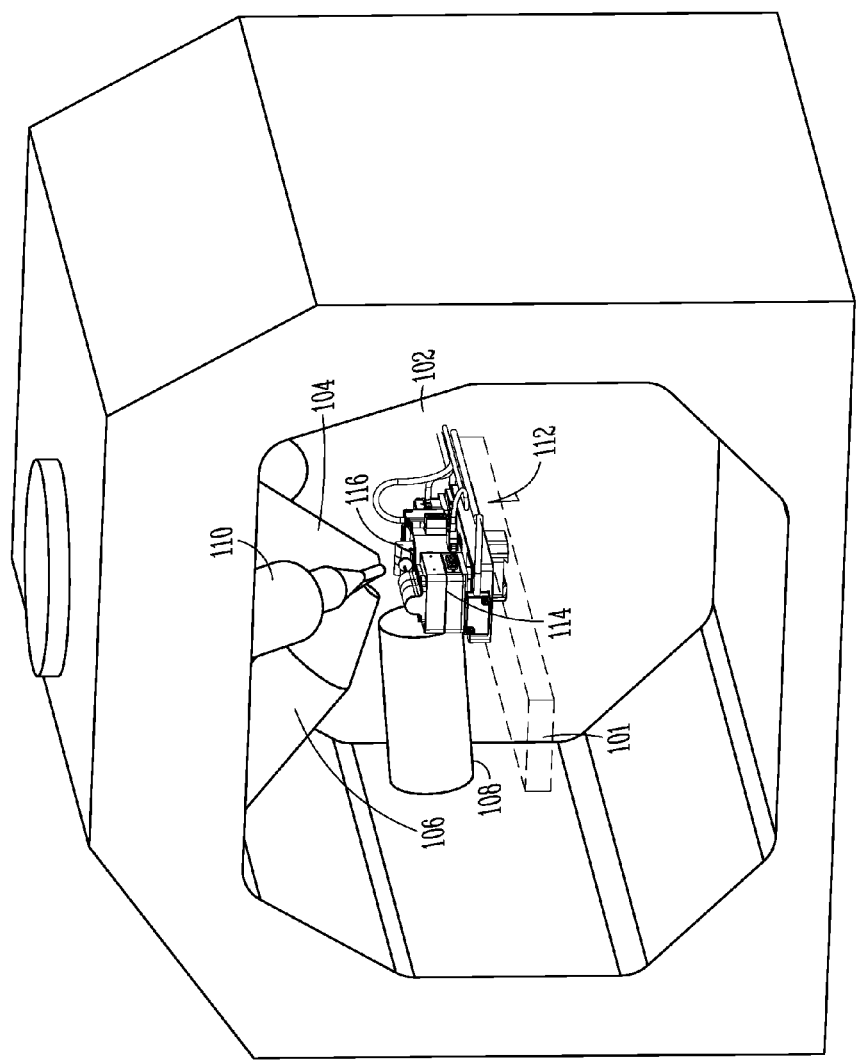
FIG. 1 is an isometric cutaway view of one example of a multi-instrument assembly including a multiple degree of freedom sample stage.

FIG. 1 shows a partial cutaway view of a multi-instrument assembly 100. As shown, the multi-instrument assembly 100 includes a microscope chamber 102 surrounding a testing assembly 112 and a plurality of instruments including first, second, third, and fourth instruments 104, 106, 108, 110. As shown, each of the first through fourth instruments 104-110 is tightly clustered around an area adjacent to the testing assembly 112. For instance, the first through fourth instruments 104-110 are arranged and include instrument axis and focal points or working distances (e.g., working regions) defining or within a localized coincidence region near the testing assembly 112, for instance, adjacent to a multiple degree of freedom sample stage 116. As will be described in further detail below, the multiple degree of freedom sample stage 116, a component of the testing assembly 112, is configured to orient a sample on a sample stage surface into a plurality of orientations relative to two or more of the instruments of the first through fourth instruments 104-110.

As shown in FIG. 1, the testing assembly 112 is positioned within the microscope chamber 102, as previously described herein. As shown, the testing assembly 112 includes a mechanical testing instrument 114 such as an indenter, a scratch (laterally moving) mechanical testing instrument, tensile testing instrument, and the like. The mechanical testing instrument 114 is configured to interact with a sample present on a sample surface stage of the multiple degree of freedom sample stage 116. The multiple degree of freedom sample stage 116 coupled with the testing assembly 112 provides multiple degrees of freedom to position and orient the sample on the sample surface stage relative to one or more of the first through fourth instruments 104-110 and the mechanical testing instrument 114. For instance, the multiple degree of freedom and sample stage 116 is configured to position a sample for interaction with the mechanical testing instrument 114 while at the same time allowing for observation and further manipulation by one or more of the first through fourth instruments, 104-110. Stated another way, the multiple degree of freedom sample stage facilitates the mechanical testing of a sample on the sample stage surface while at the same time (or contemporaneously) the sample is observed or manipulated by one or more of the first through fourth instruments, 104-110. In a similar manner, the multiple degree of freedom sample stage 116 allows for the positioning and orientation of the sample within the compact volume of the localized coincidence region formed by each of the first through fourth instruments, 104-110. As will be described in further detail herein, the multiple degree of freedom sample stage 116 allows for the positioning and orientation of the sample within this tight clustered area within the microscope chamber 102 without interaction or collision with any of the first through fourth instruments 104-110. Stated another way, the multiple degree of freedom sample stage 116 is configured to orient the sample stage surface (e.g., one or more of the sample, the sample stage surface, or a portion of the sample stage surface) to each of the working regions in the localized coincidence region through a combination of movement of two or more of the plurality of linear, rotation and tilt stages.

In one example the multi-instrument assembly 100 includes a microscope instrument such as a scanning electron microscope including, for instance, a first instrument 104 such as an electron gun and a second instrument 108 such as an electron back scatter detector. In another option, the multi-instrument assembly 100 includes a third instrument 110 such as a secondary electron detector and a fourth instrument 106 such as a focused ion beam gun. In one example, the fourth instrument 106 is a tool configured to further process the sample positioned on the sample stage surface. For instance, the fourth instrument 106, in one example a focused ion beam gun, is configured to remove portions of the sample and expose previously unavailable portions of the sample for further study and interaction with the mechanical testing instrument 114 and one or more of the first through third instruments 104-108.

Overview of the Testing Assembly

Figure 2:
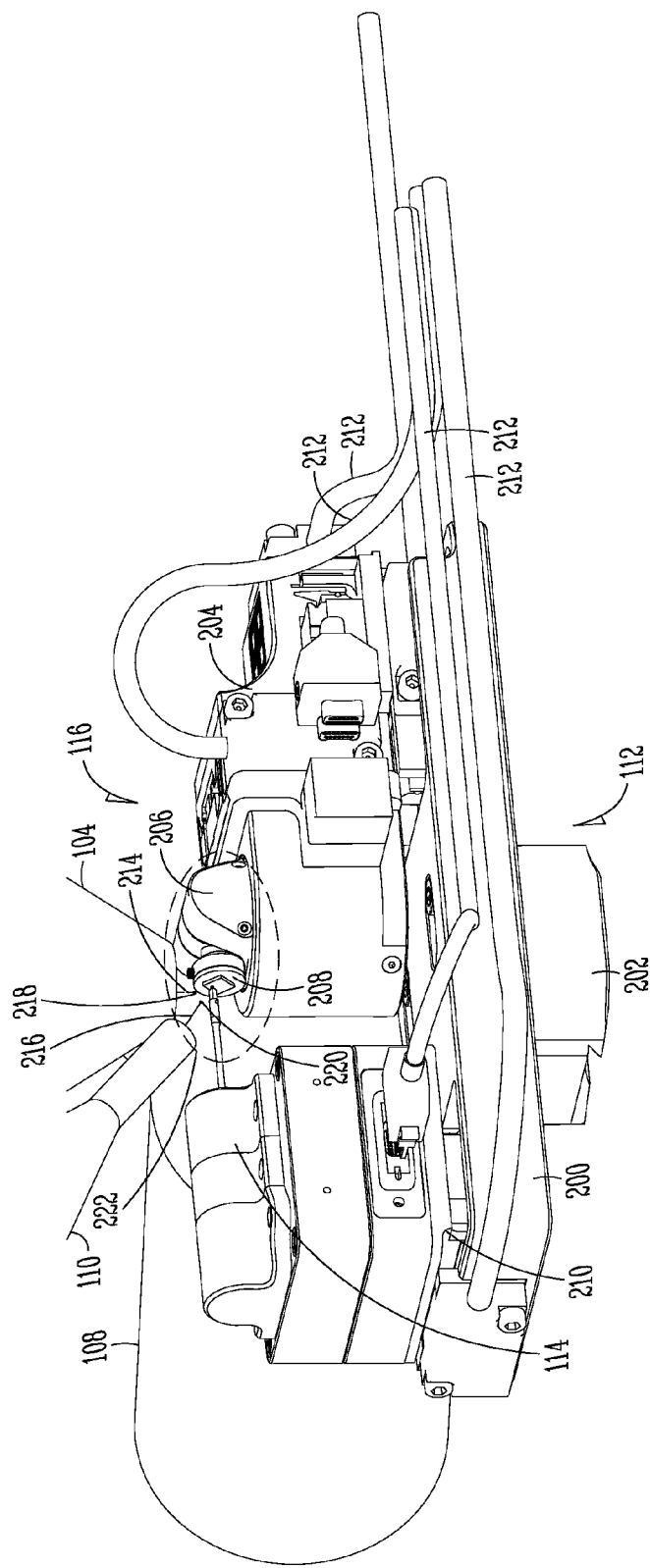
FIG. 2 is an isometric view of a testing assembly that includes the multiple degree of freedom sample stage shown in FIG. 1 with a sample stage surface in a first orientation.

FIG. 2 shows one example of the testing assembly 112 previously shown in FIG. 1. As previously described, the testing assembly 112 includes a mechanical testing instrument 114 in one example. The testing assembly 112 further includes a multiple degree freedom sample stage 116. Referring now to FIG. 2, the testing assembly 112 includes a testing assembly platform 200 sized and shaped to receive and mount each of the mechanical testing instrument 114 and the multiple degree of freedom sample stage 116. The testing assembly platform 200 further includes an assembly mount 202. The assembly mount 202 in one example is configured for positioning with and engagement to a mounting stage 101 of the multi-instrument assembly 100 (see FIG. 1). The assembly mount 202 allows for the actuation of the testing assembly relative to the instruments 104-110 of the multi-instrument assembly 100. Further, the multiple degree of freedom sample stage 116 provides additional orientation and positioning ability for a sample positioned on the sample stage surface of the multiple degree of freedom sample stage 116.

Referring again to FIG. 2, the multiple degree of freedom sample stage 116 includes, in the example shown, a linear stage assembly 204. In one example, the linear stage assembly includes X, Y, and Z linear stages configured to position the sample stage surface 208 along one or more of the linear axes. Additionally, the multiple degree of freedom sample stage 116 includes a rotation and tilt stage assembly 206 coupled with the linear stage assembly 204. In one example, the rotation and tilt stage assembly 206 is coupled in series with the linear stage assembly 204. In another example, one or more of the rotation and tilt stages is interposed between one or more of the linear stages of the linear stage assembly 204.

In yet another example, the mechanical testing instrument 114 is coupled with the testing assembly platform 200 with a mechanical testing instrument linear stage 210 (e.g., a stage configured to move the instrument relatively along an X axis) interposed therebetween. In one example, the mechanical testing instrument linear stage 210 includes one or more linear stages (one or more of X, Y or Z linear stages) configured to move the mechanical testing instrument 114 relative to the sample stage surface 208 as well as one or more of the first through fourth instruments 104-110.

As further shown in FIG. 2, actuation and sensing cabling 212 extends to one or more portions of the testing assembly 112, for instance to each of the linear stages of the linear stage assembly 204 as well as each of the rotation and tilt stages of the rotation and tilt stage assembly 206. Additionally, in another example actuation and sensing cabling 212 is provided for the mechanical testing instrument 114, as well as the mechanical testing instrument linear stage 210.

The actuation and sensing cabling 212 facilitates the actuation of each of the linear, rotation and tilt stages, the mechanical testing instrument, and the like. In another example, the actuation and sensing cabling 212 is coupled with encoders provided with each of the stages of the linear stage assembly 204, the rotation and tilt stage assembly 206, and the mechanical testing instrument linear stage 210 to facilitate the accurate actuation and positioning and orientation measurement of the instruments and sample stage surface 208 as described herein.

Referring again to FIG. 2, each of the instruments 104, 110 is shown with respective first instrument and second instrument axes 214, 216. In one example, each of the instruments includes first and second focal points 218, 220, respectively. In one example, the focal points include working distances, for instance a range of distances from the first and second instruments 104, 110. The instrument axes and focal points 214-220 described herein are exemplary. Additionally, the instruments described and shown in FIG. 1, for instance the second instrument 106 and third instrument 108 include corresponding instrument axes and focal points. In one example, the instrument axes and focal points define working regions that correspondingly form a localized coincidence region 222 in a tightly clustered position between each of the instruments 104-110 according to the consolidated or composite of the working regions. The coincidence region 222 provides a volume within the microscope chamber 102 within which the sample stage surface 208 including a sample thereon must be positioned within to provide access and utility for each of the instruments 104-110 as well as the mechanical testing instrument 114. Stated another way, the multiple degree of freedom sample stage 116 includes rotational, tilting, and linear degrees of freedom to position the sample stage surface 208 in substantially any desired orientation within the coincidence region 222 to provide access for observation and interaction with one or more of the instruments 104-110 and the mechanical testing instrument 114.

Further, the multiple degree of freedom sample stage 116 is configured to position the sample stage surface 208 within the coincidence region 222 without undesired collision with any of the instruments 104-110 and the mechanical testing instrument 114. Optionally, the mechanical testing instrument 114 on the mechanical testing instrument linear stage 210 is configured to cooperate with movement of the multiple degree of freedom sample stage 116 to ensure mechanical testing interaction is possible with the sample stage surface 208 in a variety of orientations that also align the sample with one or more the instruments 104-110. For instance, a sample is aligned with the mechanical testing instrument 114 while the sample is also oriented relative to one or more of the instruments 104-110.

Linear Stages of the Linear Stage Assembly

Figure 3:
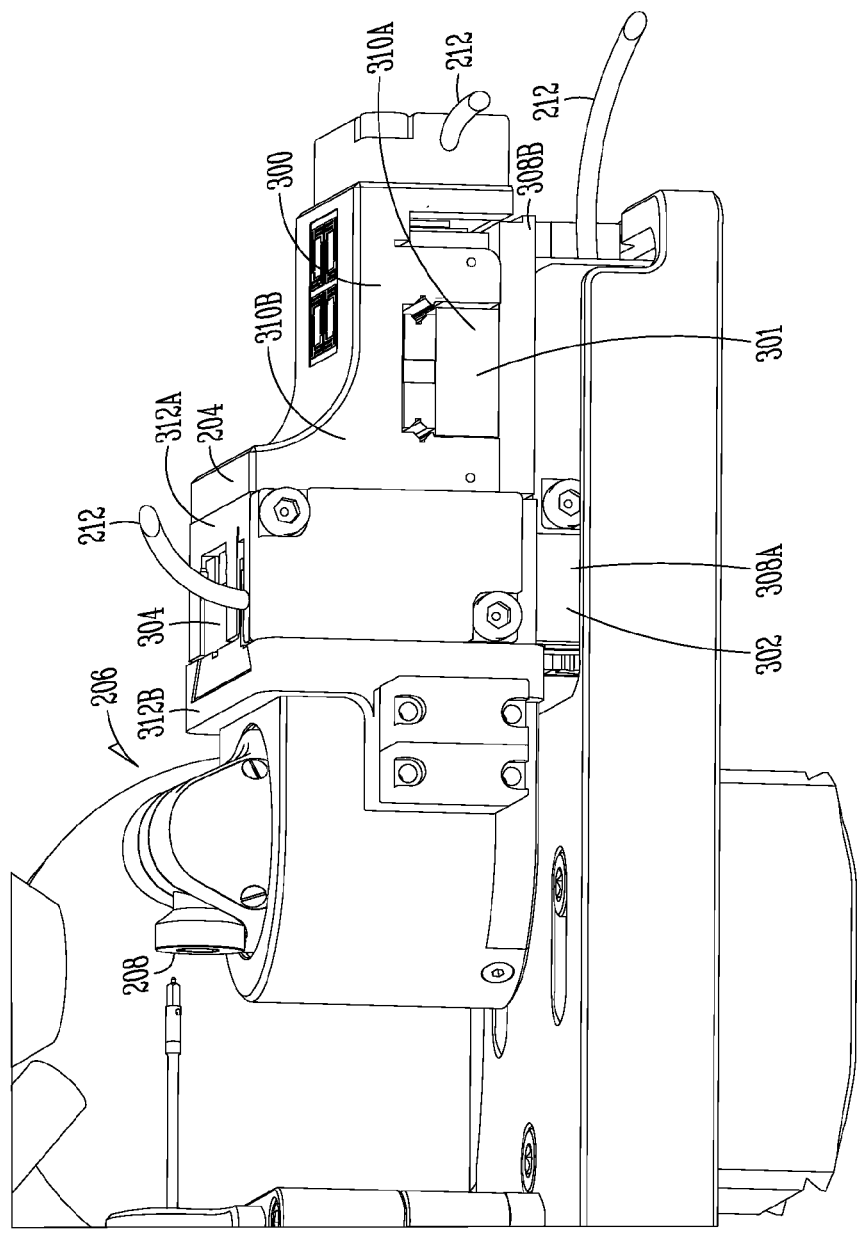
FIG. 3 is a detailed isometric view of the multiple degree of freedom sample stage shown in FIG. 1.

FIG. 3 shows a perspective view of the linear stage assembly 204. In the example shown in FIG. 3, the linear stage assembly 204 includes an X axis linear stage 300, a Y axis linear stage 302, and a Z axis linear stage 304. As described herein, each of the linear stages includes a stage base and a stage platform. In one example, the stage base is considered the base portion of each of the linear stages and the stage platform is the portion moved relative to the stage base. For instance, with regard to the Y axis linear stage 302, the Y axis linear stage includes a stage base 308A and a moveable stage platform 308B coupled with the stage base 308A. In another example, the X axis linear stage 300 includes a stage base 310A and a movable stage platform 310B movable relative to the stage base 310A. Similarly, the Z axis linear stage 304 includes a stage platform 312B movable relative to a stage base 312A. As shown in FIG. 3, one or more of the stage bases 308A, 310B, and 312B is in some examples part of a stage platform 308B, 310B, 312B of one of the other linear stages 300-304. Stated another way, the stage platform or stage base of one of the linear stages is in at least some examples a portion, for instance an integral or coupled portion, of the other stage bases or stage platforms of the other linear stages 300-304. The linear stages 300-304 are thereby provided in series to provide X, Y, and Z movability of the sample stage surface 208.

As shown in the example in FIG. 3, the linear stage assembly 204 is coupled with the rotation and tilt stage assembly 206. In one example, the X, Y, and Z axes linear stages 300, 302, 304 are configured to orient and position the sample stage surface 208, including the rotation and tilt stage assembly 206. In another example, the X, Y and Z axes linear stages 300, 302, 304 (and 210) include, but are not limited to, one or more linear stages manufactured and sold by Physik Instrumente GmbH & CO. of Germany; Dynamic Structures and Materials, LLC of Franklin Tenn.; Attocube Systems AG of Germany; SmarAct GmbH of Germany; and PiezoSystem Jena GmbH of Germany. The linear stages 300, 302, 304 include actuators 301 (Shown in FIG. 3 with stage 300 and stages 302, 304 include duplicate or similar actuators 301) that move the stage platforms relative to the respective stage bases and include, but are not limited to, linear drive stages having stepper motors, piezo motors, voice coil actuators, stick-slip actuators and the like. One example of a motor usable with one or more of the linear stages 300, 302, 304 is a linear motor provided by Dynamic Structures and Materials, LLC having model number 1-30.

Optionally, the linear stages 300, 302, 304 are configured to provide precise linear movement along a desired axis (e.g., the X, Y or Z axis), and as described herein otherwise constrain lateral movement of the stage platforms 308B, 310B, 312B relative to the respective stage bases 308A, 310A, 312A and the corresponding linear axes. For instance, as described herein, cross roller bearing assemblies (shown in FIG. 7) provide surface to surface contact by way of crossed roller bearings. The surface to surface contact constrains lateral motion of the platforms relative to the bases (e.g., provides a minimal tolerance that allows for linear motion but substantially prevents lateral movement). Stated another way, the cross roller bearing assemblies provide rigid structural support through surface-to-surface contact between each of the stage platforms and stage bases. The cross roller bearing assemblies provide a stiff supportive structure between the stage platforms and the stage bases to substantially prevent movement of the stage platforms relative to the stage bases in any axis except along the linear axis of the stages 300, 302, 304. In other examples, the linear stages include other bearing assemblies, including, but not limited to ball bearings, sliding bearings and the like.

In another example, the linear stages 300, 302, 304 include one or more clamping or locking features that lock (e.g., anchor, hold, retain and the like) the stage platforms 308B, 310B, 312B relative to the respective stage bases 308A, 310A, 312A in an unpowered configuration. That is to say, one or more of the linear stages 300, 302, 304 anchors the respective stage platform 308B, 310B or 312B relative to the respective stage base 308A, 310A or 312A when the actuator of the stage is not operated. The clamping or locking feature cooperates with the bearing assemblies (e.g., cross roller bearing assemblies) to provide individual stages that are structurally stable along each axis (X, Y and Z) while static, and capable of precise linear movement with stage platforms 308B, 310B, 312B that are constrained from moving laterally (e.g., substantially prevented from lateral movement). The linear stages 300, 302, 304 in combination thereby provide a linear stage assembly 204 that allows movement along each of the linear axes (X, Y and Z axes) that also minimizes tolerance between the stage platforms and bases. The lateral constraint provided in each of the linear stages, for instance by the cross roller bearing assemblies in combination with the clamping or locking features of one or more of the linear stages 300, 302, 304 accordingly ensures the linear stage assembly 204 is stable and supports the sample stage surface 208 in any desired static orientation for mechanical testing.

Mechanical Testing Instrument

Figure 4:
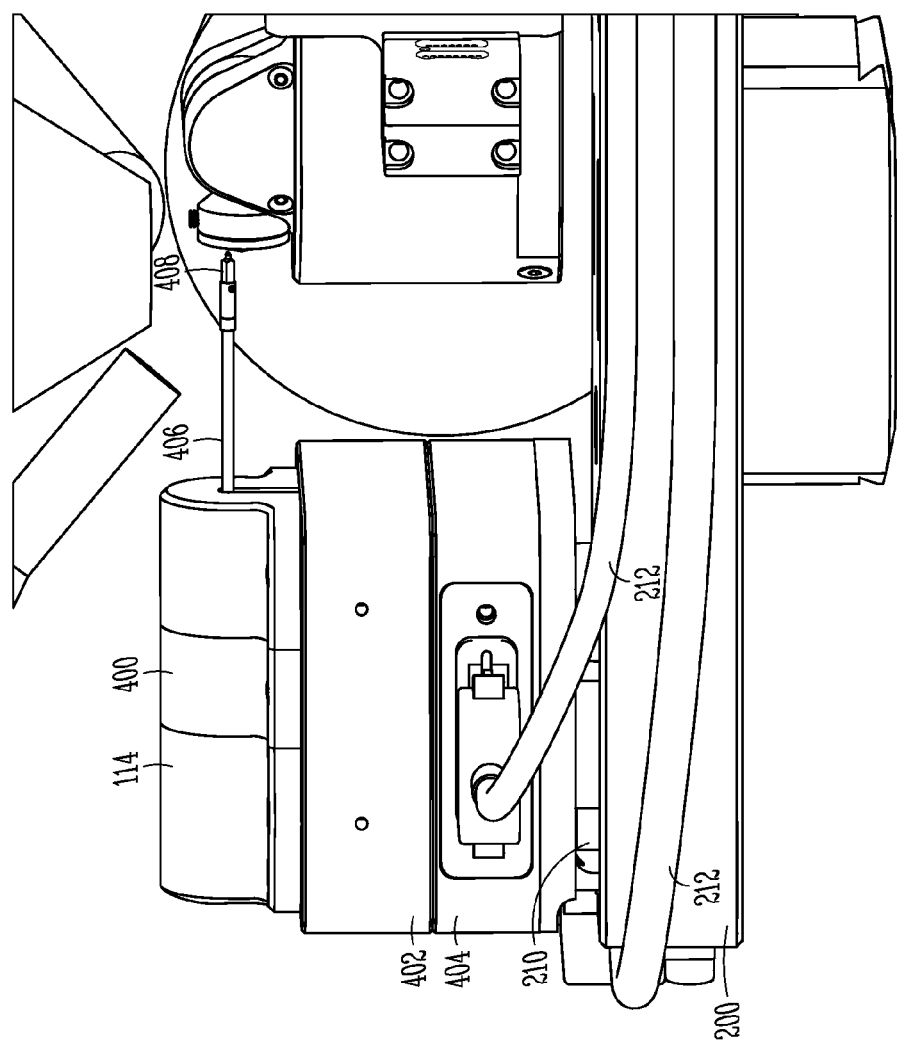
FIG. 4 is an isometric view of one example of mechanical testing instrument coupled with the testing assembly.

FIG. 4 shows the mechanical testing instrument 114 previously shown in FIG. 1. As shown, the mechanical testing instrument 114 includes an instrument housing 400 including therein transducers, sensors and the like configured for operation and sensing of movement of the instrument shaft 406 and an instrument tip 408 at the end of the instrument shaft 406. As described herein, the mechanical testing instrument 114 is configured to engage with and test (e.g., indent, scratch, provide tensile force through grip features and the like) a sample present on the sample stage surface 206 coupled with the multiple degree of freedom sample stage 116. In another example, the mechanical testing instrument 114 includes a three dimensional transducer configured to provide one or more of indentation, scratching and the like of the instrument tip 408 over the sample present on the sample stage surface 208.

In one example, the mechanical testing instrument 114 includes a modular design. For instance the mechanical testing instrument 114 includes an instrument interface 402 sized and shaped for corresponding engagement with a complementary electromechanical interface 404. In one example, the electromechanical interface 404 is coupled with a portion of the mechanical testing instrument linear stage 210. The electromechanical interface 404 provides a mechanical interface for the structural components of the mechanical testing instrument 114 and at the same time provides an electrical interface for the transducer and any other instruments, sensors, or detectors of the mechanical testing instrument 114. In another example, the electromechanical interface 404 provides mechanical and electrical connections with any of a number of instruments configured for modular connection with the electromechanical interface 404 for instance at an instrument interface 402 of the respective instruments. For instance, the mechanical testing instrument 114 includes, but is not limited to an array of separate instruments such as an indenter, a scanner, a detector, and the like. Each of the instruments is configured for one or more of mechanical engagement and testing with the sample present on the sample stage surface 208 and/or observation and scanning or detection of features and characteristics of the sample present on the sample stage surface 208.

Referring again to FIG. 4, the mechanical testing instrument linear stage 210 (e.g., a linear X stage) is shown coupling the mechanical testing instrument 114 (including for instance the electromechanical interface 404) with the testing assembly platform 200. As described herein, the mechanical testing instrument linear stage 210 provides for at least linear movement of the mechanical testing instrument 114, relative to the multiple degree of freedom sample stage 116 including, for instance, a sample present on the sample stage surface 208.

The Testing Assembly Mount

Figure 5:
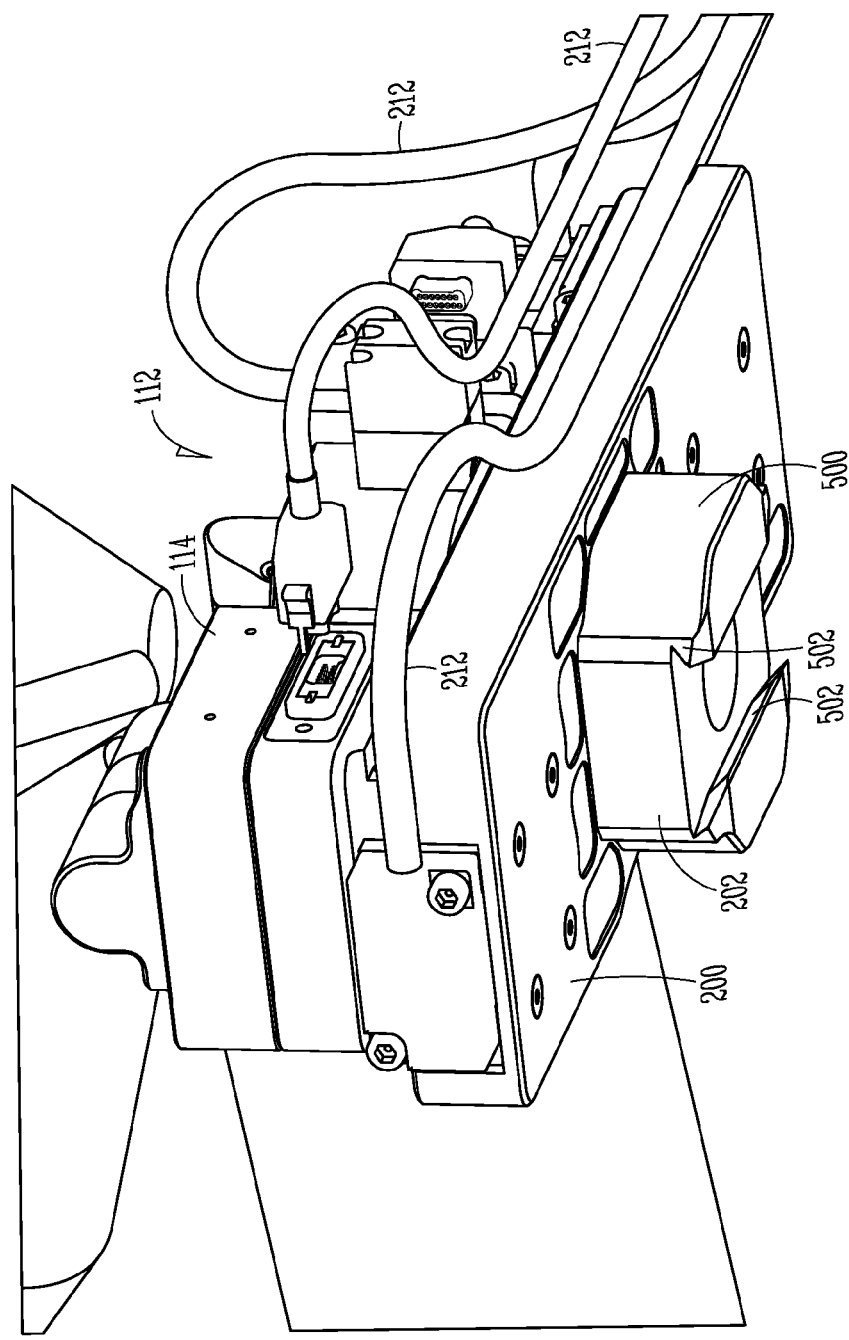
FIG. 5 is a bottom isometric view of the testing assembly of FIG. 2 including one example of an assembly mount.

FIG. 5 shows another view of the testing assembly 112 including the testing assembly platform 200. In the view shown in FIG. 5, a bottom portion of the testing assembly 112 is provided. As previously described, in one example the testing assembly 112 includes an assembly mount 202 provided on a portion of the testing assembly platform 200. As shown in FIG. 5, the assembly mount 202 extends from the testing assembly platform 200 and is configured for cooperative engagement with a mounting stage 101 of the multi-instrument assembly 100. In one example, the assembly mount 202 includes a mount perimeter 500. The mount perimeter 500 is sized and shaped for complementary engagement (e.g., reception) within a corresponding orifice of the mounting stage 101 of the multi-instrument microscope 100. For instance, the mount perimeter 500 is non-circular and complementary to the mounting stage orifice of the multi-instrument assembly 100. The non-circular perimeter ensures the testing assembly platform 200 is non-rotatably coupled with the mounting stage 101 of the multi-instrument assembly 100. Further, the non-circular perimeter 500 of the assembly mount 202 ensures that movement of the testing assembly 112, for instance, provided by the mounting stage 101 of the multi-instrument assembly 100 is accurately and reliably transmitted to the testing assembly platform 200 (for instance by avoiding relative rotation between a circular orifice and a circular mount). Accordingly, a multi-instrument assembly 100 configured to actuate a mounting stage 101 is thereby able to provide further flexibility of orientation (e.g., one or more of linear, rotational and tilting) in addition to multiple degrees of freedom provided by the testing assembly 112, as described herein.

In another example, the assembly mount 202 includes a platform coupling feature 502 such as a dovetail extending along at least one of the surfaces of the assembly mount 202. In one example, the platform coupling feature 502 is sized and shaped for complementary engagement with a corresponding feature of the mounting stage 101 of the multi-instrument assembly 100. The platform coupling feature 502 affirmatively engages the testing assembly 112 with the multi-instrument assembly 100 (e.g., when mounted) to thereby provide a solid structural support rigidly coupled with the assembly 100.

Figure 6:
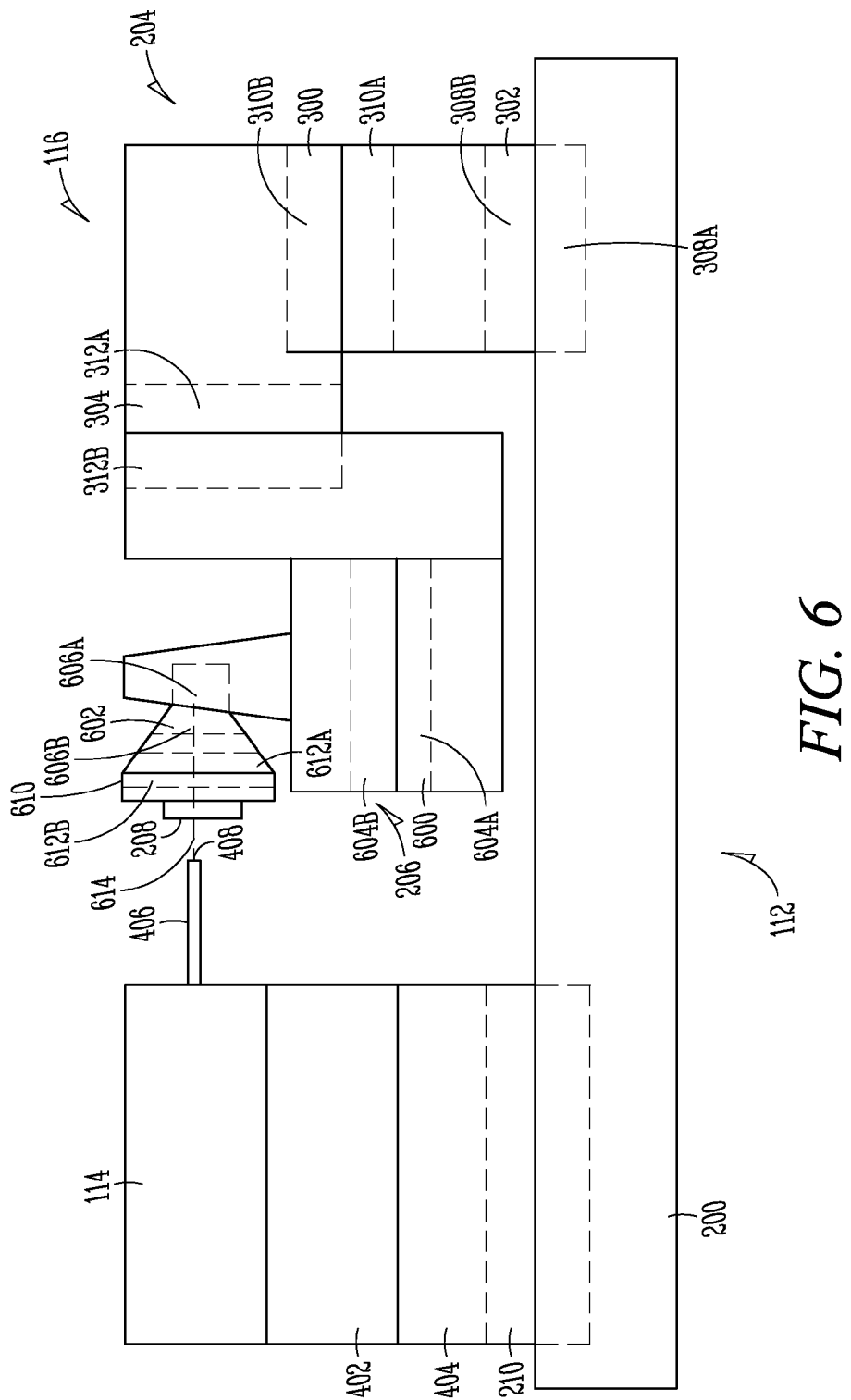
FIG. 6 is a schematic view of the testing assembly of FIG. 2 including multiple linear stages, a rotation stage and a tilt stage.

Schematic Representation of the Multiple Degrees of Freedom for the Testing Assembly FIG. 6 shows a schematic representation of the testing assembly 112 including, for instance, the mechanical testing instrument 114 and the multiple degree of freedom sample stage 116. As previously described, each of the multiple degree of freedom sample stage 116 and the optional mechanical testing instrument 114 are coupled with a testing assembly platform 200 and thereby form a unitary design configured for coupling with a mounting stage 101 of a multi-instrument assembly, such as the assembly 100 shown in FIG. 1.

The schematic representation in FIG. 6 shows each of the degrees of freedom of movement of the testing assembly 112 including the degrees of freedom for the sample stage surface 208 as well as the mechanical testing instrument 114

(including the instrument shaft 406 and the instrument tip 408). As described herein, the multiple degrees of freedom for both the multiple degree of freedom sample stage 116 and the mechanical testing instrument 114 in combination with the stage provide enhanced flexibility for the positioning and orienting of the sample on the sample stage surface 208 relative to one or more instruments such as the instruments 104-110 and the mechanical testing instrument 114 shown in FIG. 1. Stated another way, with the compact form factor of the testing assembly 112, a sample is capable of being positioned and oriented relative to one or more instruments in a plurality of orientations to provide access and interactivity with the instruments along with in situ testing with the mechanical testing instrument 114 despite the tight clustered nature of the instruments 104-110 without requiring manual repositioning of the sample relative to the desired instruments.

Referring again to FIG. 6, a rotation stage 600 is shown coupled with the linear stage assembly 204. In one example, the rotation stage 600 is coupled in series with the linear stage assembly 204. In another example, the rotation stage 600 is coupled between one or more of the X, Y or Z axis linear stages 300-304. In a similar manner, a tilt stage 602 is coupled with the rotation stage 600. The tilt stage 602 is shown coupled in series with the rotation stage 600. In another example, the tilt stage 602, similarly to the rotation stage 600, may be interposed between one or more of the rotation stage 600 and a linear stage such as the X, Y or Z axis linear stages 300-304. Optionally, the tilt stage 602 is positionable between any of the linear stages 300-304. In still another example, any one of the rotation and tilt stages 600, 602 is positionable between the testing assembly platform 200 and one or more of the linear stages 300-304.

Referring first to the rotation stage 600, the rotation stage 600 includes a stage base 604A coupled with the stage 312B of the Z axis linear stage 304. Additionally, the rotation stage 600 includes a stage platform 604B movably coupled with the stage base 604A. The stage platform 604B is rotatable relative to the stage base 604A according to the actuation of one more actuators described later herein.

Referring again to FIG. 6, the tilt stage 602 is shown with a corresponding stage base 606A and stage platform 606B. In one example, the stage platform 606B is coupled with the sample stage surface 208. The stage platform 606B is tiltable relative to the stage base 606A, and in one example the stage platform 606B, including the sample stage surface 208 coupled thereon, is configured for movement, for instance, over an arc of 180 degrees from the position shown in FIG. 6. Stated another way, the sample stage surface 208 and the stage platform 606B are positionable in an orientation opposed to the orientation shown in FIG. 6. In another example, the rotation stage 600 is rotatable over an arc of approximately 180 degrees thereby allowing for positioning of the sample stage surface 208 in substantially any orientation along the 360 degree circuit of the rotation stage 600. The rotation stage 600 and the tilt stage 602 when operated in combination allow for the positioning of sample stage surface 208 along a full 360 degree circuit around the center axis of the rotation stage 600.

Optionally, the multiple degree of freedom sample stage includes a sample rotational stage 610 interposed between the sample stage surface 208 and the tilt stage 602. In one example, the sample rotational stage 610 includes a stage base 612A and a stage platform 612B. The stage base 612A is in one example coupled with the stage platform 606B of the tilt stage 602, and the stage platform 612B is coupled with the sample stage surface 208. The sample rotation stage 610 is operable to rotate the sample stage surface 208 and a sample thereon around a sample surface rotation axis 614 (shown in FIG. 6). Rotation provided by the sample rotation stage 610 facilitates the positioning and alignment of a sample (e.g., a heterogenous sample, sample with multiple testing locations and the like) with one or more instruments, as described herein. The sample rotation stage 610 provides an additional degree of freedom to the testing assembly 112, for instance a sixth degree of freedom in combination with the rotation and tilt stages 600, 602 and the linear stages 300, 302, 304.

The sample rotation stage 610 in another example, is configured similarly to the rotation or tilt stages 600, 602 described in detail herein. For instance, the sample rotation stage 610 includes one or more motors, such as piezo motors that operate to rotate the stage platform 612B and the sample stage surface 208. In another example and similarly to the rotation or tilt stages 600, 602, while the sample rotation stage 610 is relaxed (e.g., the motor is not operated), the stage 610 operates to clamp the stage platform 612B in place to stably and reliably position the sample thereon for mechanical testing using mechanical engagement with the sample.

As further shown in FIG. 6, the mechanical testing instrument 114 is coupled with the testing assembly platform 200 with the mechanical testing instrument linear stage 210. In one example, the mechanical testing instrument linear stage 210 provides one or more linear axes of movement to the mechanical testing instrument 114. In one example, the mechanical testing instrument linear stage 210 provides movement along an X axis, for instance along an axis parallel to the X axis of the X axis linear stage 300 of the linear stage assembly 204.

In one example, the provision of dual linear stages on each of the mechanical testing instrument 114 and for the multiple degree of freedom sample stage 116 allows for the positioning of the sample stage surface 208 and the mechanical testing instrument 114 in a form factor substantially defined by the testing assembly platform 200. For instance, if the testing assembly 112 is viewed in a plan view, movement of the sample stage surface 208, for instance along an X axis corresponding to the X axis linear stage 300 shown in FIG. 6, would normally move the sample stage surface 208 relative to the testing platform 200 and in some circumstances move one or more of the linear stages 300-304 and/or the rotation and tilt stages 600, 602 substantially out of the perimeter of the testing assembly platform 200. When used in cooperation with the mechanical testing instrument linear stage 210, the mechanical testing instrument linear stage may be moved in an opposed direction relative to the movement of the multiple degree of freedom sample stage 116 along the linear axis of the mechanical testing instrument linear stage 210. In this manner, the projection of the mechanical testing instrument 114 and the multiple degree of freedom sample stage 116 outside of the boundary of the testing platform 200 is substantially minimized. Stated another way, if the sample stage surface 208 requires orientation into a configuration that would push the multiple degree of freedom sample stage 116 substantially outside of the bounds of the testing platform 200, for instance to orient the sample relative to an instrument as well as the mechanical testing instrument 114. The mechanical testing instrument 114 may instead be cooperatively moved in an opposed direction to thereby minimize the projection of both the mechanical testing instrument 114 and the multiple degree of freedom sample stage 116 beyond the perimeter of the testing assembly platform 200.

Referring again to FIG. 6, the linear stage assembly 204 is shown again with the schematic representation. For instance, the Y axis linear stage 302 includes a stage base 308A and a stage platform 308B. Similarly, the X axis linear stage 300 includes a stage base 310A and a stage platform 310B. The Z axis linear stage 304 includes a stage base 312A and a stage platform 312B. As shown in FIG. 6, the stage platforms and stage bases of each of the stages, including the rotation and tilt stages 600, 602, may, in some examples, be integral to corresponding stage bases and stages of other actuators. For instance, the stage platform 308B of the Y axis linear stage 302 is coupled with or integral to the stage base 310A of the X axis linear stage 300. In a similar manner, the stage base 604A of the rotation stage 600 is integral to or coupled with the stage platform 312B of the Z axis linear stage 304.

The multiple degree of freedom sample stage 116 with the linear stage assembly 204, including the X, Y and Z axes linear stages 300-304 as well as the rotation and tilt stages 600, 602, provides at least five degrees of freedom for the sample stage surface 208. As described above, the mechanical instrument linear stage 210 provides an enhanced degree of freedom and flexibility for cooperative positioning of the sample stage surface 208 as well as the mechanical testing instrument 114. In the case of the multiple degree of freedom sample stage 116, the X axis linear stage 300 is configured to provide movement of at least the sample stage surface 208 into and out of the page as shown in FIG. 6. In a similar manner, the Y axis linear stage 302 is configured to provide movement of the sample stage surface 208 from the left to the right or the right to the left as shown in FIG. 6. The Z axis linear stage 308 correspondingly provides movement of the sample stage surface 208 towards the top and the bottom of the page as shown in FIG. 6. The rotation stage 600 provides rotation of the sample stage surface 208 and the tilt stage 602 provides tilting of the sample stage surface 208. The multiple degrees of freedom (e.g., five or more degrees of freedom) provided by at least the multiple degree of freedom sample stage 116 thereby provides flexibility in the orienting and positioning of the sample stage surface 208 relative to any of the instruments 104-110 show in FIG. 1 as well as the mechanical testing instrument 114. The positioning of the sample stage surface 208 is performed within the tight clustered area provided by the instruments 104-110 in one example. Stated another way, the multiple degree of freedom sample stage 116 allows for the positioning of the sample stage surface 208 in any of a variety of orientations directed into or out of the coincidence region 222 defined by the working regions of one or more of the instruments 104-110 and allows for the reliable and accurate positioning of the sample on the sample stage surface 208 according to the working parameters of each of the instruments 104-110 while at the same time providing sufficient flexibility to allow interaction with the mechanical testing instrument 114, for instance, contemporaneously with observation by any one of the one or more instruments 104-110.

Cross Roller Bearing Assembly

Figure 7:
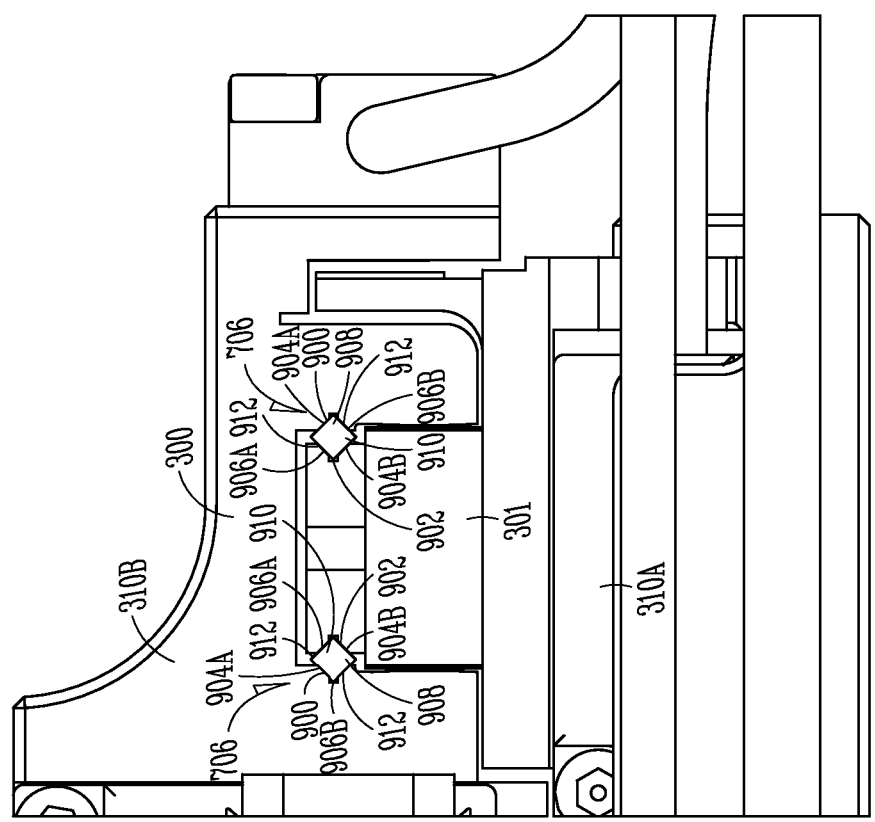
FIG. 7 is a cross sectional view of one example a cross roller bearing assembly interposed between a stage and a stage base.

As described herein, in one example, cross roller bearing assemblies 706 (See FIG. 7) are included between the stage platform and stage bases of one or more of the linear stages such as the X, Y, and Z axis linear stages 300-304 of the linear stage assembly 204 and the mechanical testing instrument linear stage 210. In one example, the cross roller bearing assemblies 706 are interposed between the stage base 310A and the stage platform 310B of the X axis linear stage 300 as shown in FIG. 7. In the example shown in FIG. 7, dual cross roller bearing assemblies 706 are interposed between the stage platform and base 310B, A. As shown, the stage platform 310B includes a first rail channel 900 extending into and out of the page substantially parallel to the linear axis of the X axis linear stage 300. A second rail channel 902 correspondingly extends into and out of the page along the portions of the actuator housing 801 (e.g., associated in one example with the stage base 310A). The first and second rail channels 900, 902 cooperate to form grooves sized and shaped to receive the plurality of roller bearings 908 therein.

As shown, for instance, in FIG. 7, the first and second rail channels 900, 902 include opposed pairs of interface surfaces. In one example, the first rail channel 900 includes a first interface surface 904A and the second rail channel 902 includes a second interface surface 904B opposed to the first interface surface 904A. In corresponding manner, the second rail channel 902 includes a first interface surface 906A and the first rail channel 900 includes a second interface surface 906B opposed to the first interface surface 906A. The like numbered interface surfaces 904A, B, and 906A, B form opposed pairs of interface surfaces aligned with and extending parallel to the linear axis of the respective linear stage.

The roller bearings 908 are positioned within the first and second rail channels 900, 902 and provide the moveable interface between the stage platform 310B and the stage base 310A. For instance, in each of the first and second rail channels 900, 902 of each of the cross roller bearing assemblies 706, a plurality of roller bearings 908 are positioned therein. In one example, the first and second rail channels 900, 902 of the cross roller bearing assembly 706 shown on the left of FIG. 7 include five or more roller bearings 908 provided therein. The roller bearings 908 are provided in an alternately crossed configuration where the cylindrical bearing surfaces 910 (e.g., the cylindrical surfaces of the roller bearings 908 as opposed to the end surfaces of the bearings) are arranged at 90 degree angles relative to each successive roller bearing within the first and second rail channels 900, 902. The roller bearings 908 within the first and second rail channels 900, 902 of the cross roller bearing assembly 706 on the right side of the X axis linear stage 300 shown in FIG. 7 are similarly positioned within the first and second rail channels 900, 902 in an alternately crossed configuration. The cylindrical bearing surfaces 901 cooperate with the opposed interface surfaces 904A, 904B, and 906A, 906B to provide opposed surface to surface engagement between the interface surfaces that correspondingly provides a robust structural coupling between the stage base 310A and the stage platform 310B.

For instance, with the configuration shown in FIG. 7 movement of the stage platform 310B relative to the stage base 310A, for instance by application of lateral force to one or more of the stage platform 310 or the stage base 310A (e.g., orthogonal or off-axis to the linear axis of the X axis linear stage 300), is substantially minimized. The surface to surface engagement between the roller bearings 908 and the interface surfaces 904A, B, and 906A, B minimizes relative tilting or lateral movement of the stage platform and stage base 310B, 310A. Stated another way, the roller bearings 908 and their crossed configuration within the first and second rail channels 900, 902 provide alternating surface to surface interfaces between the opposed interface surfaces 904A, B, and 906A, B, to substantially prevent relative movement orthogonal to the linear axis of the X axis linear stage 300. That is to say, tolerances otherwise provided in other bearing systems (and multiplied across multiple stages coupled in series) are minimized between the multiple stages of the linear stage assembly 204 and the linear stage 210 used with the mechanical testing instrument 114.

The cylindrical bearing surfaces 910 in one example have a shorter length relative to the diameter of the planar end surfaces 912 of each of the roller bearings 908. Because the planar end surfaces 912 have a larger diameter than the length of the cylindrical bearing surfaces 910, movement and engagement of the roller bearings 908 with the opposed interface surface 904A, 904B, and 906A, 906B at the first and second rail channels 900, 902 is focused on the cylindrical bearing surfaces 910. Stated another way, the cylindrical bearing surfaces 901 are shorter than the distance between the opposed interface surfaces 904A, 904B and 906A, 906B. With the planar end surfaces 912 having a greater diameter than the length of the cylindrical bearing surfaces 910, affirmative engagement between the planar end surfaces 912 and the opposed pairs of interface surfaces 904A, 904B, and 906A, 906B is minimized. Instead, the movable coupling is provided between the cylindrical bearing surfaces 910 and the opposed interface surfaces. Only incidental engagement between the planar end surfaces 912 of the roller bearings 908 and the opposed interface surfaces 904A, 904, and 906A, 906B occurs. Stage platform 310B is thereby able to smoothly move relative to the stage base 310A along the linear axis of the stage according to operation of the actuator 301 while being constrained against movement along non-parallel axes as described herein. That is to say, the cross roller bearing assemblies 706 guide movement of the stage platform 310B along the linear axis (the direction of translation) of the stage, while at same time constraining (e.g., minimizing or eliminating) lateral movement, tilting and the like of the stage platform 310B relative to the stage base 310A and the linear axis of the stage.

Importantly, the actuator 301 is able to accurately and reliably move the stage platform 310B relative to the stage base 310A according the minimized tolerance of the cross roller bearing assembly 706. That is to say, the stage platform 310B is constrained to move only along the linear axis of the X axis linear stage 300. Orthogonal movement, for instance, movement due to tolerances between spherical bearings and the like between a stage platform and a stage base is substantially prevented by the cross roller bearing assembly 706 (or assemblies in one example). The interface surfaces 904A, 904B and 906A, 906B in combination with the alternately crossed roller bearings 908 substantially prevents tilting and lateral movement of the stage platform 310B relative to the stage base 310A.

In one example, the roller bearings 908 described herein are constructed with, but not limited to, a ceramic material such as silicon nitride. By constructing the roller bearings 908 with a ceramic material such as silicon nitride, roller bearings 908 may be packed within the first and second rail channels 900, 902 in a side-by-side relationship. For instance, the plurality of roller bearings 908 in each of the first and second roll channels 900, 902 may be positioned within the channel successively with the roller bearings 908 in engagement with each other (e.g., in an alternating crossing relationship as described herein). The roller bearings 908 have a minimal coefficient of friction in engagement of the roller bearings 908, for instance along their cylindrical bearing surfaces 910. The minimized friction has minimal effect on the ease of movability of the stage platform 310B relative to the stage base 310A. In another example, the first and second rail channels 900, 902, for instance, of the actuator housing 801 and the stage 310B are constructed with similar or identical materials to the stage base and platform 310A, B, for instance, titanium, steel, and the like.

Rotation and Tilt Stage Assembly

Figure 8A:
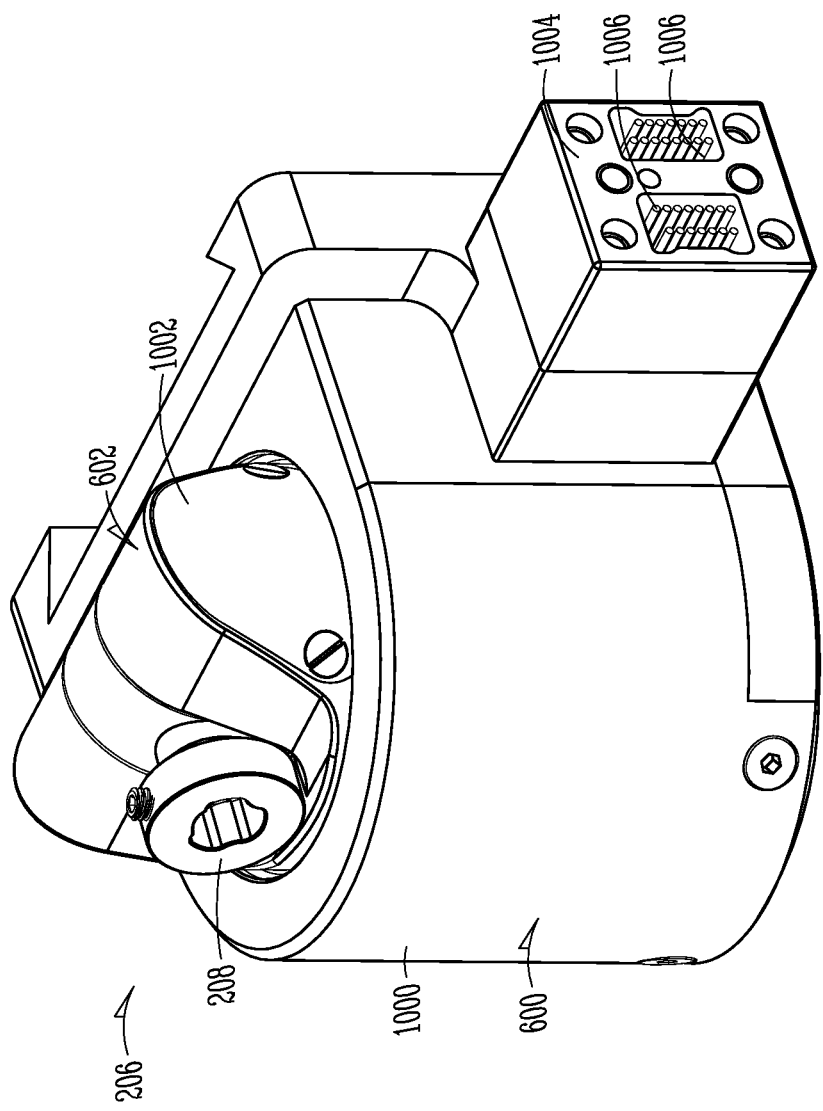
FIG. 8A is an isometric view of one example of an assembly including rotation and tilt stages.

FIG. 8A shows an isometric view of the rotation and tilt assembly 206 previously shown in FIG. 2. As described herein, the rotation tilt assembly 206 is configured for coupling in series with the linear stage assembly 204. In other examples, the rotation and tilt stage assembly 206 is configured for interposing coupling between one or more of the linear stages 300-304 as described herein. In still another example, the rotation and tilt stage assembly 206 is configured for positioning between the testing assembly platform 200 and one or more of the linear stages of the linear stage assembly 204.

Referring again to FIG. 8A, the rotation and tilt stage assembly 206 includes the rotation stage 600 and the tilt stage 602 coupled with the rotation stage. As shown, a rotation stage housing 1000 extends around the rotation stage 600. Similarly, a tilt stage housing 1002 extends over at least a portion of the tilt stage 602. The sample stage surface 208 is shown coupled with the tilt stage 602. In one example, the rotation stage housing 1000 includes an electrical interface 1004 providing rotation and tilt sockets 1006 for coupling with actuation and sensing cabling 212, for instance, for encoder measurements and instructions to operate and detect the position of the rotation and tilt stages 600, 602.

Figure 8B:
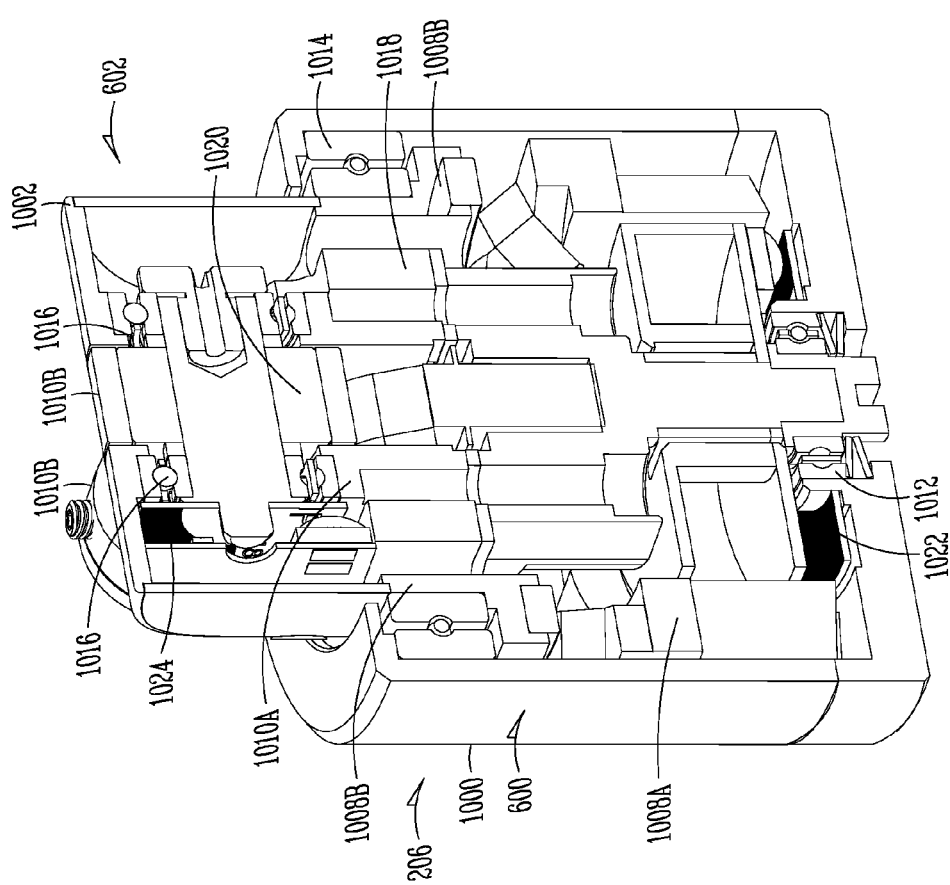
FIG. 8B is a cross sectional view of the assembly of the rotation and tilt stages shown in FIG. 8A.

Referring now to FIG. 8B, the rotation and tilt stage assembly 206 as previously shown in FIG. 8A is shown in cross section. The rotation stage 600 includes a rotation stage platform 1008B and a rotation stage base 1008A. Similarly the tilt stage 602 includes a tilt stage base 1010A and a tilt stage platform 1010B. In one example, the rotation stage platform 1008B and the tilt stage base 1010A are incorporated into a rotation spindle assembly 1018. As shown in FIG. 8B, the rotation spindle assembly 1018 is configured for rotatable movement within the rotation stage housing 1000.

In one example, a plurality of rotational bearings 1012, 1014 are provided between the rotation spindle assembly 1018 and the rotation stage housing 1000. The rotational bearings 1012, 1014 facilitate the rotation of the rotation spindle assembly 1018 relative to the housing 1000. In one example, the rotational bearings 1012, 1014 include a plurality of ball bearings interposed between the respective rotation stage housing 1000 and the rotation spindle assembly 1018. In a similar manner to the rotation spindle assembly 1018, the tilt stage 602 in one example includes a tilt spindle assembly 1020 incorporating the tilt stage platform 1010B. The tilt spindle assembly 1020 is movably coupled with the rotation spindle assembly 1018, for instance, with tilt bearings 1016 on either side of the tilt spindle assembly 1020. In one example, the tilt bearings include ball bearings interposed between the tilt spindle assembly 1020 and the rotation spindle assembly 1018. Optionally, one or both of the rotation and tilt stages 600, 602 include respective rotation encoders 1022 and tilt encoders 1024 to accurately measure the position of the respective rotation spindle assembly 1018 relative to the rotation stage housing 1000 and the position of the tilt spindle assembly 1020 relative to the rotation spindle assembly 1018.

Rotation Stage

Figure 9:
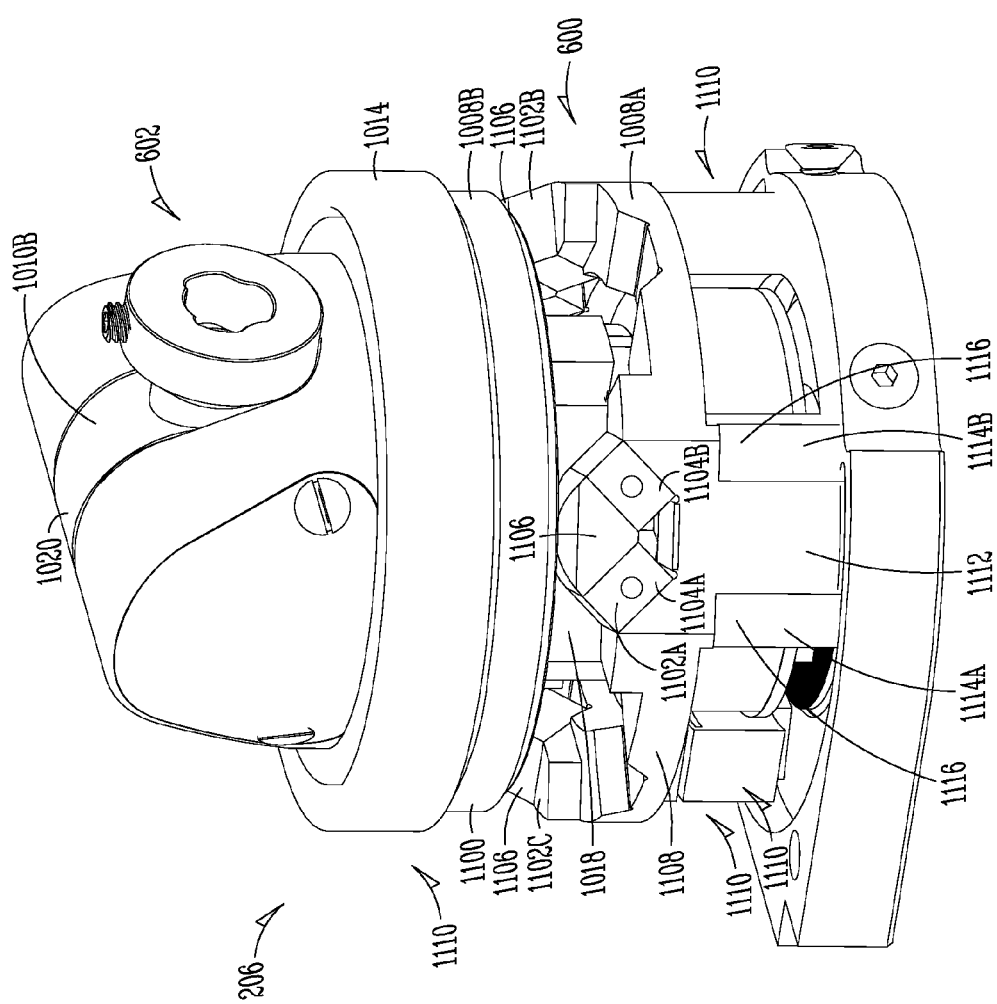
FIG. 9 is an isometric view of piezo motors and a clamping assembly of the rotation stage shown in FIG. 8A.

FIG. 9 shows the rotation and tilt stage assembly 206. In the example shown, the rotation stage housing 1000 has been removed to expose the components within the rotation stage 600. As previously described, the rotation and tilt assembly 206 includes a rotation stage 600 coupled with a tilt stage 602. Referring to FIG. 9, the rotation stage 600 as shown includes the rotation stage platform 1008B rotationally coupled with the rotation stage base 1008A. As previously described, in one example the rotation stage platform 1008B includes a rotation spindle assembly 1018 including a portion of, for instance, the tilt stage base 1010A. (See FIG. 8B). Optionally, the sample rotation stage 610 shown in FIG. 6 is configured similarly to the rotation stage 600 (e.g. with similar motor assemblies and a similar clamping assembly).

As shown in FIG. 9, the rotation stage 600 includes a plurality of piezo motor assemblies 1102A-C (e.g., motors) positioned around the rotation stage 600. Each of the piezo motor assemblies 1102A-C includes first and second opposed piezo motors 1104A, B (e.g., motor elements). Interposed between each of the first and second opposed motors 1104A, B is a drive shoe 1106 engaged with the stage platform 1008B. In one example, the stage platform 1008B includes a rotation flange 1100 coupled with the remainder of the stage platform 1008B. As shown in FIG. 9, the rotation flange 1100 extends around and is engaged with the drive shoes 1106 of the piezo motor assemblies 1102A-C. In one example, the piezo motor assemblies 1102A-C work in parallel to move the rotation flange 1100 to effectuate rotation of the rotation spindle assembly 1018. For instance, the first opposed motors 1104A of each of the piezo motor assemblies 1102A-C are operated in parallel (e.g., simultaneously expanded and relaxed following a saw tooth drive signal to move the drive shoes 1106) to effectuate rotation in one direction while the second opposed motors 1104B of the piezo motor assemblies 1102A-C are operated in parallel to effectuate rotation of the rotation spindle assembly 1018 in an opposed direction (e.g., clockwise versus counterclockwise). Optionally, the opposed motors 1104A of each of the assemblies 1102A-C are operated in sequence (each expanding and relaxing in a preceding or succeeding fashion to the other motors 1104A) to rotate the rotation spindle assembly 1018 in a first direction. Similarly, the opposed motors 1104B of each of the assemblies 1102A-C are operated in sequence to rotate the rotation spindle assembly 1018 in a second opposed direction. In yet another option, the rotation stage 600 includes one or more motor assemblies (e.g., one or more of motor assemblies 1102A-C) and one or more of the motor assemblies are operated to actuate the rotation stage 600.

Referring again to FIG. 9, the piezo motor assemblies 1102A-C are shown coupled with a motor support ring 1108 extending beneath and around the rotation flange 1100. The motor support ring 1108 provides a robust structure for the support of each of the piezo motor assemblies 1102A-C. Additionally, the motor support ring 1108 is supported within the rotation stage base 1008A by a support column 1112 coupled with a plurality of spring elements 1114A, B (e.g., separate spring elements or virtual spring elements of the same spring). As shown in FIG. 9, the plurality of support columns 1112 and spring elements 1114A, B are arranged around the motor support ring 1108 and thereby provide a solid but deflectable coupling with the remainder of the rotation stage base 1008A. The motor support ring 1108 in another example includes spring contact points 1116 positioned adjacent to the sides the piezo motor assemblies 1102A-C (e.g., bracketing the assemblies or having the assemblies interposed therebetween). Optionally, the motor support ring 1108 includes one or more contact points 1116 (one, two, three or more contact points). In one example, a single contact point 1116 is associated with each of the one or more motor assemblies 1102A-C.

In the example shown in FIG. 9, the spring elements 1114A, B positioned on either side of the support columns 1112 (separate springs or elements of a single spring having plural elements extending to the separate contact points 1116 extending from the support column 112) are coupled between the spring contact points 1116 and the support column 1112. As will be described in further detail below, the spring elements 1114A, B provide opposed biasing support to each of the piezo motor assemblies 1102A-C to provide a clamping function through the piezo motor assemblies 1102A-C to the rotatable spindle assembly 1018. In other words, the spring elements 1114A, B clamp the spindle assembly 1018 (e.g., the stage platform 1008B) statically relative to the stage base 1008A) when the piezo motor assemblies 1102A-C are not otherwise rotating the spindle assembly.

Referring again to FIG. 9, a clamping assembly 1110 is shown at either end of the rotation spindle assembly 1018. In one example, the clamping assembly 1110 includes, for instance, the rotation bearing 1014 coupled with the rotation stage base 1008A as well as the spring elements 1114A, B. As previously described, the spring elements 1114A, B are coupled between the support column 1112 and the spring contacts 1116. The spring elements 1114A, B bias the motor support ring 1108 as well as the piezo motor assemblies 1102A-C in an upward direction toward the rotation flange 1100. While the piezo motor assemblies 1102A-C are in a relaxed state (e.g., are not being operated to effectuate rotation of the rotation spindle assembly 1018) the spring elements 1114A, B bias the motor support ring 1108 upwardly and thereby affirmatively engage the drive shoes 1106 against a first surface of the rotation flange 1100 to substantially prevent undesired rotation of the rotation spindle assembly 1018. Stated another way, the rotation spindle assembly 1018 is locked in place and static even when acted upon by outside forces, for instance, upon the tilt spindle assembly 1020 and rotation spindle assembly 1018 (e.g., through mechanical testing of a sample). The drive shoes 1106 of the piezo motor assemblies 1102A-C statically hold the rotation spindle assembly 1018 in place through the application of friction through the normal force applied by the spring elements 1114A, B of each of the springs arranged around the motor support ring 1108.

As shown in FIG. 9, in one example the spring elements 1114A, B include multiple spring elements extending between the support column 1112 and the spring contacts 1116. Optionally, the spring elements 1114A, B include spring elements having at least one switchback extending between a support column 1112 and the spring contacts 1116. In another example, the spring elements 1114A, B each include a single spring element extending between the support column 1112 and each of the spring contacts 1116. The spring elements 1114A, B (whether a single spring or multiple springs) in one example, include, but are not limited to flexural springs having a substantially flat perimeter that is layered one or more times over itself in a serpentine fashion.

As shown in FIG. 9, each of the drive shoes 1106 is arranged around the motor support ring 1108. When engaged with the rotation flange 1100 the drive shoes 1106 of each of the three piezo motor assemblies 1102A-C provide a solid upward biased support to the rotation flange 1100 and thereby clamp the rotation flange 1100 between a clamping surface including, but not limited to, the rotation bearing 1014 (engaged along a second surface of the rotation flange) and the drive shoes 1106 (engaged along a first surface of the rotation flange) to effectuate the static locked positioning of the rotation flange 1100 and the rotation spindle assembly 1118 coupled with the flange 1100. Stated another way, the clamping assembly 1110 clamps the stage platform 1008B between the spring elements 1114A, B (and in one example the motor assemblies 1102A-C) and an opposed portion of the stage base 1008A (e.g., a clamping surface) to lock the stage platform 1008B in place. As described herein, in one example, the clamping assembly 1110 clamps around first and second surfaces of a portion of the stage platform 1008B, such as the rotation flange 1100, with the spring biased motor assemblies 1104A-C and the rotational bearing 1014 associated with the stage base 1008A.

Tilt Stage

Figure 10A:
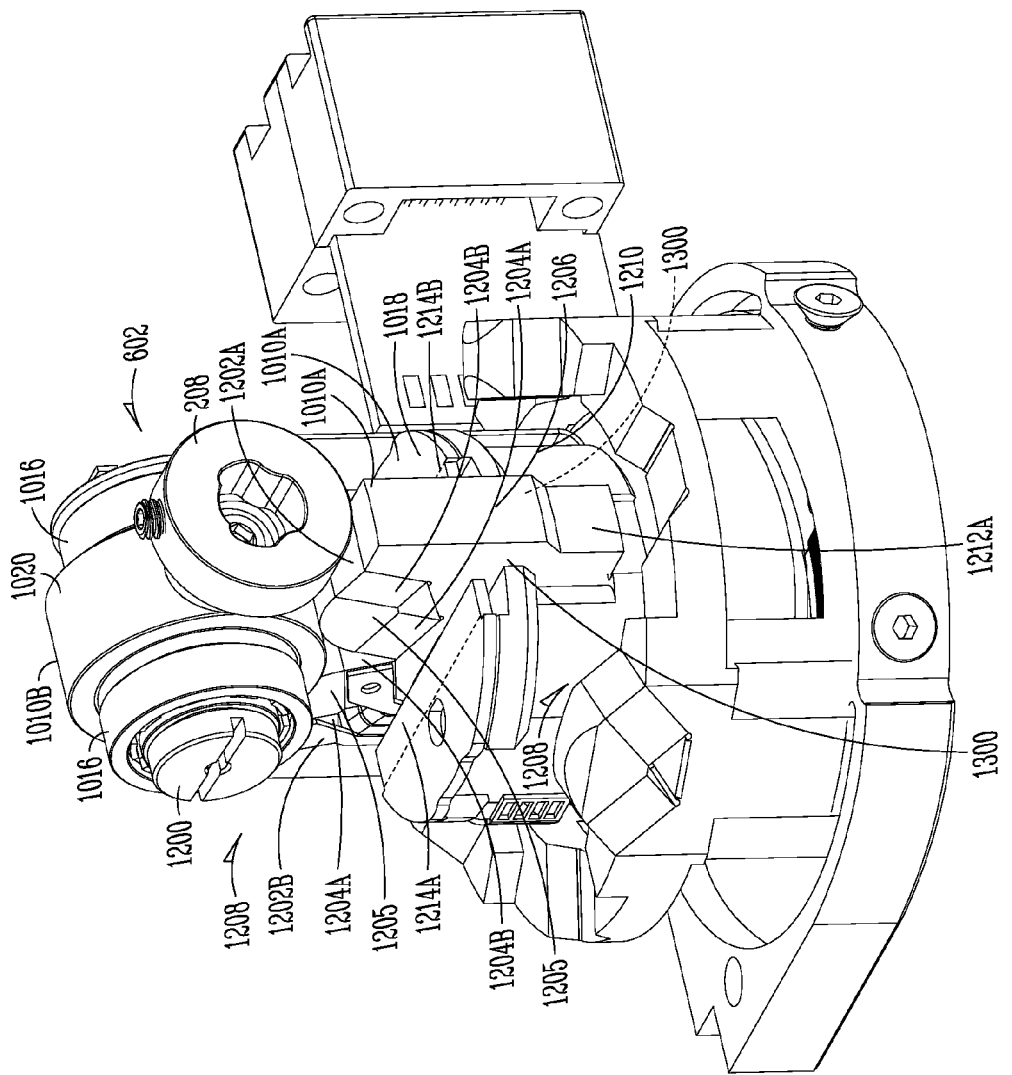
FIG. 10A is an isometric view of piezo motors and a clamping assembly of the tilt stage shown in FIG. 8A.
Figure 10B:
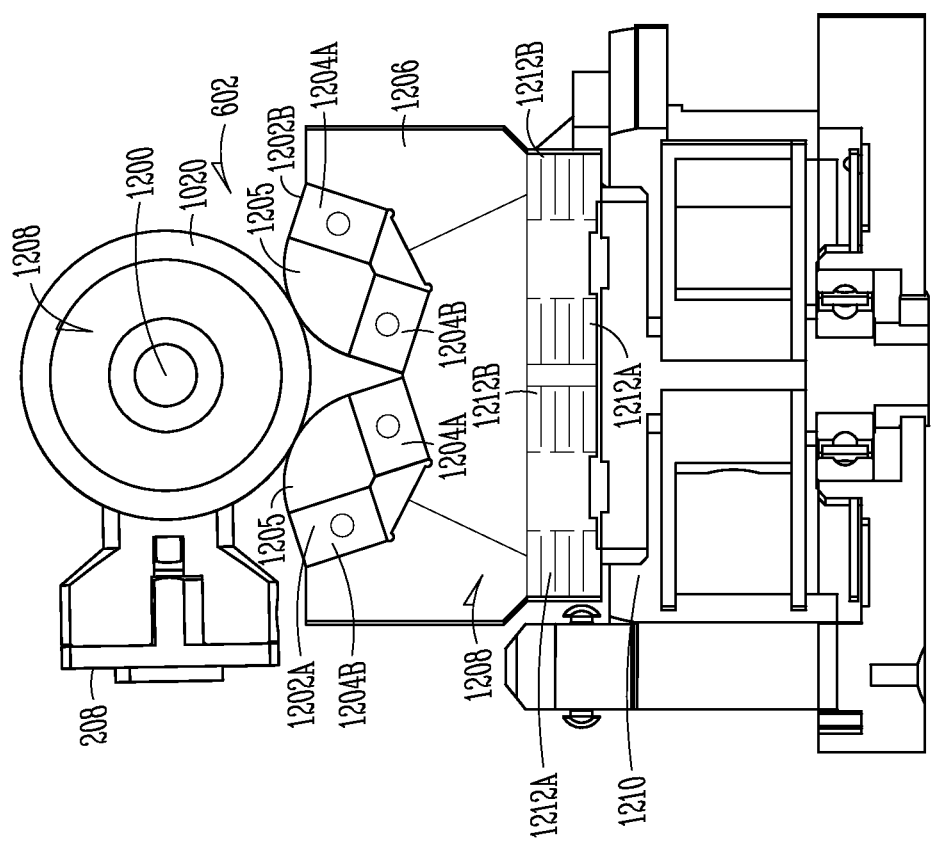
FIG. 10B is a cross sectional view of the tilt stage of FIG. 8A showing a plurality of actuator shoes providing two or more points of contact between the stage base and the stage of the tilt stage.
Figure 12:
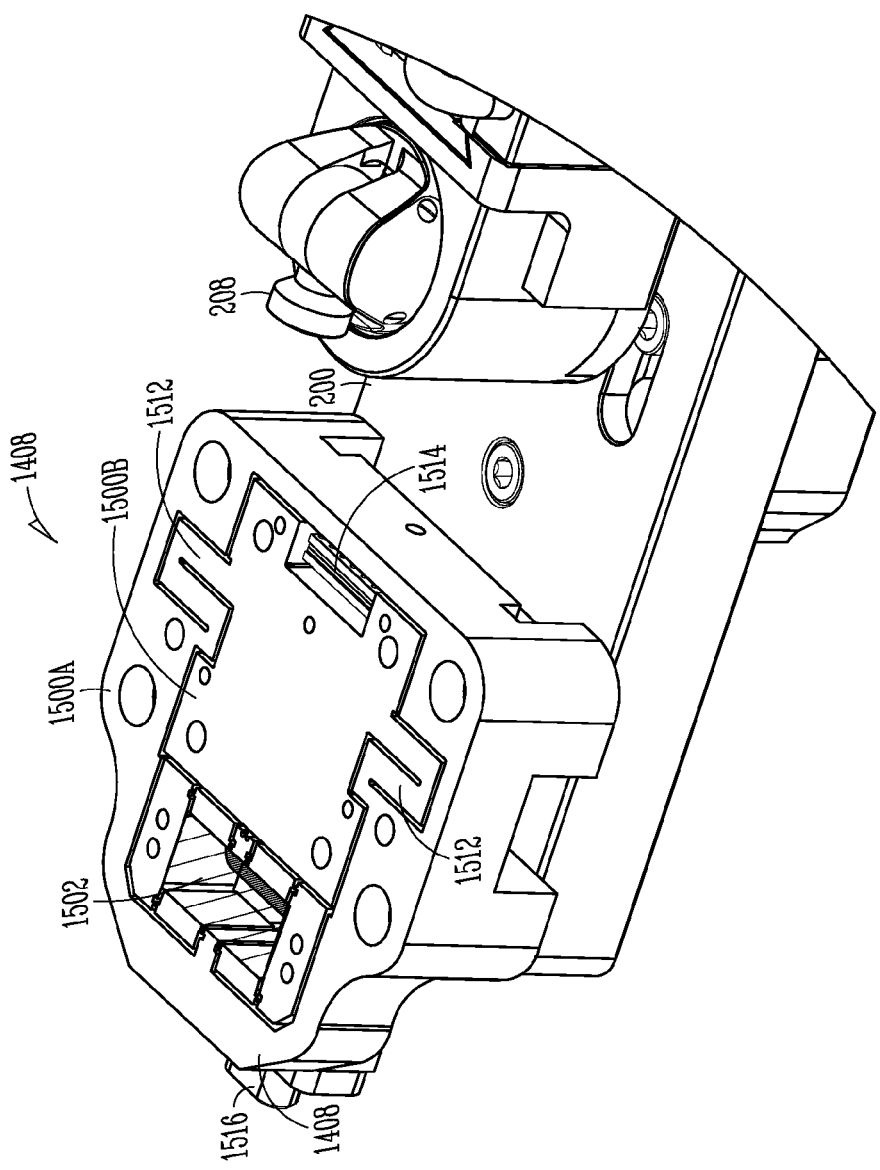
FIG. 12 is an isometric view of the stage shown in FIG. 11.

FIGS. 10A and 10B show respective perspective and cross sectional views of the tilt stage 602 of the rotation and tilt stage assembly 206 previously shown in FIG. 2. Referring first to FIG. 10A, the tilt stage 602 is shown including the tilt stage platform 1010B and the tilt stage base 1010A. As previously described, in one example the tilt stage base 1010A is incorporated in the rotation spindle assembly 1018 previously described and shown in FIGS. 8A and 8B. The tilt stage platform 1010B is incorporated into a tilt spindle assembly 1020 rotatably coupled with the rotation spindle assembly 1018. As shown in FIG. 12, the tilt spindle assembly 1020 is supported in one example by the tilt bearings 1016 that facilitate rotational movement of the tilt spindle assembly 1020 relative to the rotation spindle assembly 1018. In one example, an axle 1200 extends through the tilt spindle assembly 1020 and supports both the tilt bearings 1016 as well as the tilt spindle assembly 1020 therebetween. Optionally, the sample rotation stage 610 shown in FIG. 6 is configured similarly to the tilt stage 602 (e.g. with similar motor assemblies and a similar clamping assembly).

As previously described, the tilt stage 602 is configured to provide tilting movement to the sample stage surface 208. For instance, the tilt stage 602 includes motor assemblies 1202A, B (e.g., piezo motor assemblies, or motors), positioned for driving engagement with the tilt spindle assembly 1020. As shown in FIG. 10A, the piezo motor assemblies 1202A, B, include two piezo motor assemblies. In another example, two or more piezo motor assemblies are provided. The piezo motor assemblies 1202A, B are positioned within a motor support saddle 1206 coupled with the tilt stage base 1010A (e.g., the rotation spindle assembly 1018). The piezo motor assemblies 1202A, B each include first and second opposed motors 1204A, B (e.g., motor elements). In one example, the first and second opposed motors 1204A, B include piezo elements. Referring to FIG. 10B, the piezo motors 1204A are configured to work in parallel (e.g., simultaneously expand and contract (relax)) to rotate the tilt spindle assembly 1020 in a clockwise direction while the piezo motors 1204B are configured to work in parallel to rotate the tilt spindle assembly 1020 in a counterclockwise direction. As shown, each of the first and second opposed motors 1204A, B are engaged with respective drive shoes 1205 associated with each of piezo motor assemblies 1202A, B. Stated another way, each of the first and second opposed motors 1204A, B of each piezo motor assembly 1202A, B engage with a single drive shoe 1205. The drive shoes 1205 of each piezo motor assembly 1202A, B thereby receive driving forces (from expansion of the piezo motors) from one or both of the first and second opposed motors 1204A, B of each of the piezo motor assemblies. Optionally, separate drive shoes are provided for each of the first and second opposed motors 1204A, B. In yet another option, the first opposed motors 1204A of each of the assemblies 1202A, B act in sequence (preceding or succeeding relative to each other) to rotate the tilt spindle assembly 1020 in a first direction, and the second opposed motors 1204B act in sequence to rotate the tilt spindle assembly 1020 in a second opposed direction.

The tilt stage 602 further includes a clamping assembly 1208 configured to fix the tilt spindle assembly 1020 in a static orientation upon conclusion of movement through the piezo motor assemblies 1202A, B. In one example, the clamping assembly 1208 includes opposed clamping surfaces provided by one or more of the axle 1200 and the piezo motor assembly 1202-B including, for instance, the drive shoes 1205. For instance, as shown in FIG. 10B, the tilt spindle assembly 1020 is shown interposed between the axle 1200 and the drive shoes 1205 of each of the piezo motor assemblies 1202A, B. In one example the axle 1200 is supported by the tilt bearings 1016 coupled with the tilt stage base 1010A. Through one or more of the tilt bearings 1016 or direct coupling of the axle 1200 with the tilt stage base 1010A, the axle is supported by the tilt stage base 1010A to provide structural support for the clamping assembly 1208 and to assist the drive shoes 1205 in affirmatively engaging the tilt spindle assembly 1020 for static positioning of the assembly after the sample stage surface 208 is positioned as desired.

Referring again to FIG. 10B the clamping assembly 1208 includes a support base 1210 forming a portion of the rotation spindle assembly 1018 in one example. The support base 1210 is sized and shaped to receive a plurality of axial spring elements 1212A, B. The axial spring elements 1212A, B extend between the support base 1210 and the motor support saddle 1206. In one example, the axial spring elements 1212A, B bias the motor support saddle 1206 and thereby bias the piezo motor assemblies 1202A, B as well as the drive shoes 1205 into an affirmative engagement with the tilt spindle assembly 1020. The affirmative engagement of the drive shoes 1205 with the tilt spindle assembly 1020 ensures the drive shoes 1205 frictionally engage the tilt spindle assembly 1020 to ensure driving of the piezo motor assemblies 1202A, B results in accurate tilting of the tilt spindle assembly 1020. Additionally, the bias provided by the axial spring elements 1212A, B ensures the affirmative engagement provided by the drive shoes 1205 provides a static frictional engagement with the tilt spindle assembly 1020 while the piezo motor assemblies 1202A, B are relaxed (e.g., not operated) to thereby clamp the tilt spindle assembly 1020 between the piezo motor assemblies 1202A, B as well as the axle 1200 (e.g., the tilt bearings 1016).

In one example, the axial spring elements 1212A, B include axial spring elements 1212A, B each associated with respective sides of the piezo motor assemblies 1202A, B. For instance, the axial spring element 1212A is associated with the piezo motor 1204B and the axial spring element 1212B is associated with the piezo motor 1204A. The axial spring elements 1212A, B thereby provide opposed biasing to each of the piezo motors 1204A, B to ensure that the piezo motors including the drive shoes 1205 are affirmatively biased into engagement with the tilt spindle assembly 1020 to ensure static clamping of the tilt spindle assembly while the piezo motor assemblies 1202A, B are not operated. Stated another way, a biasing force is provided to each of the opposed first and second piezo motors 1204A, B to provide a corresponding force vector through each of the piezo motors to the drive shoe 1205 and thereby substantially prevent tilting or sliding of the drive shoe 1205 off of the tilt spindle assembly 1020. The axial spring elements 1212A, B associated with each of the piezo motor assemblies 1202A, B thereby provide affirmative engagement on at least two points around the tilt spindle assembly 1020. The axle 1200 thereby clamps the tilt spindle assembly 1020 at a point of contact at the axle and the tilt spindle assembly 1020 between two points of contact formed by the drive shoes 1205 and the tilt spindle assembly 1020. The tilt spindle assembly 1020 is thereby clamped at three points on opposed surfaces of the tilt spindle assembly to ensure that the tilt spindle assembly is statically held in place when the first and second opposed motors 1204A, B of the motor assemblies 1202A, B are not operated. Optionally, the axial spring elements 1212A, B are consolidated into unitary springs that support each of the piezo motor assemblies 1202A, B (e.g., to the left and the right sides of the motor support saddle 1206, immediately below each of the assemblies 1202A, B, or the like).

Lateral Spring Elements of the Tilt Stage

Referring again to FIG. 10A, in another example the tilt stage 602, for instance the clamping assembly 1208, further includes lateral spring elements 1214A, B to provide lateral support to the support saddle 1206 and the axial spring elements 1212A, B. The lateral spring elements 1214A, B support the motor support saddle 1206 and the axial spring elements 1212A, B as they bias the drive shoes 1205 of each of the piezo motor assemblies 1202A, B into engagement with the tilt spindle assembly 1020. For instance, the lateral spring elements 1214A, B substantially prevent the lateral movement of the piezo motor assemblies 1202A, B out of engagement or out of alignment with the tilt spindle assembly 1020. Instead, the lateral spring elements 1214A, B constrain depression and elevation of the motor support saddle 1206 (through deflection of the axial spring elements 1212A, B) to substantially axial depression and elevation to ensure that the drive shoes 1205 engage in surface-to-surface contact with the tilt spindle assembly 1020 throughout operation of the piezo motor assemblies 1202A, B as well as static positioning of the tilt spindle assembly 1020.

As shown in FIG. 10A, the lateral spring elements 1214A, B are coupled between the tilt stage base 1010B, such as the rotation spindle assembly 1018 (the support base 1210), and the motor support saddle 1206. Gaps 1300 are formed between the motor support saddle 1206 and the support base 1210 to facilitate the axial deflection of the axial spring elements 1212A, B with corresponding movement of the motor support saddle 1206 and the first and second piezo motor assemblies 1202A, B. As shown, the lateral spring elements 1214A, B bridge the respective gaps 1300 (on either side of the saddle 1206) and thereby provide deflectable lateral support to each side of the motor support saddle 1206. The lateral spring elements 1214A, B thereby ensure the motor support saddle 1206 is able to move upwardly and downwardly according to the bias provided by the axial spring elements 1212A, B as well as deflection caused by movement of the first and second opposed motors 1204A, B of each of the piezo motor assemblies 1202A, B.

The lateral spring elements 1214A, B constrain the motion of the support saddle 1206, the axial spring elements 1212A, B as well as the piezo motor assemblies 1202A, B to axial movement while substantially preventing lateral movement of the associated components. By constraining the motor support saddle 1206 the axial spring elements 1212A, B and the piezo motor assemblies 1202A, B to axial movement lateral misalignment of the drive shoes 1205, for instance, with the tilt spindle assembly 1020 shown in FIGS. 10A and 10B is thereby substantially avoided. The drive shoes 1205 are thereby maintained in an affirmative surface-to-surface engagement with the tilt spindle assembly 1020 throughout operation of the piezo motor assemblies 1202A, B, as well as in the static retaining configuration where the drive shoes 1205 frictionally engage with the tilt spindle assembly 1020 to substantially prevent undesired tilting movement of the tilt spindle assembly 1020 (e.g., the tilt stage platform 1010B) relative to the tilt stage base 1010A (e.g., the support base 1210 where the rotation spindle assembly 1018).

Testing Assembly Including a Stage for Use with a Mechanical Testing Instrument

Figure 11:
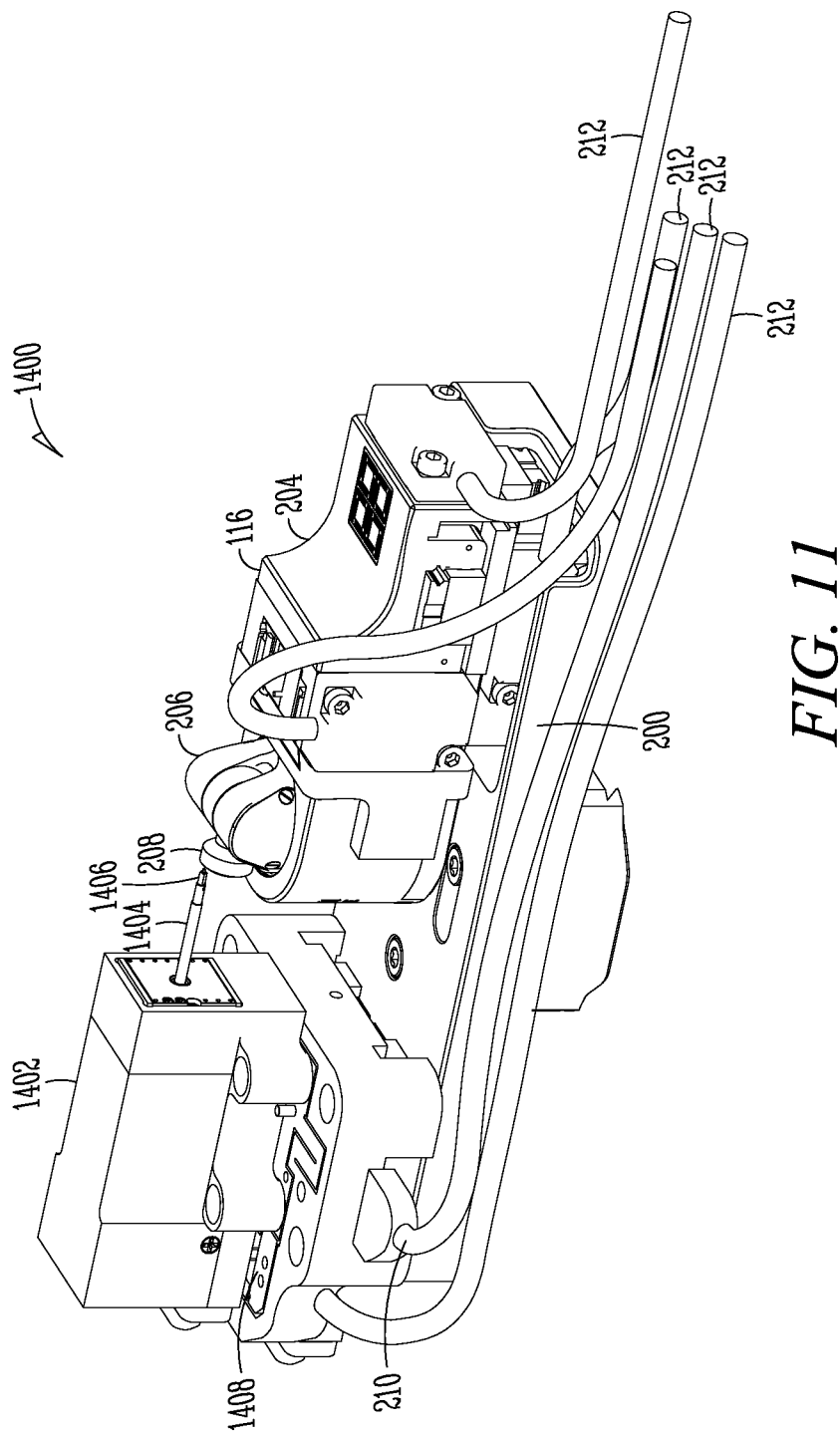
FIG. 11 is an isometric view of another example of a testing assembly that includes a stage coupled with a mechanical testing instrument.

FIG. 11 shows another example of the testing assembly 1400 configured for use, for instance, with the multi-instrument assembly 100 shown in FIG. 1. At least some of the features of the testing assembly 1400 are similar or identical to previously described features herein and are incorporated with regard to the testing assembly 1400. As shown in FIG. 11, the testing assembly 1400 includes a multiple degree of freedom sample stage 116 including a linear stage assembly 204 and a rotation and tilt stage assembly 206 coupled with the linear stage assembly 204. The rotation and tilt stage assembly 206 includes a sample stage surface 208. The multiple degree of freedom sample stage 116 as previously described, is configured to move the sample stage surface 208 into a variety of orientations and positions to facilitate observation and interaction with a sample on the sample stage surface 208, for instance, for with the mechanical testing instrument 1402 as well as any of the first-fourth instruments 104-110 shown in FIG. 1.

In one example, the multiple degree of freedom sample stage 116 is configured to move the sample stage surface 208 into these configurations to facilitate one or more of observation and interaction of the sample on the sample stage surface 208 contemporaneously. For instance, two or more instruments observe or interact with the sample on the sample stage surface at the same time according to the positioning of the sample stage surface 208 with one or more of rotation, tilting, and linear positioning of the sample stage surface 208 (e.g., with the multiple degree of freedom sample stage 116). In another example, the mechanical testing instrument linear stage 210 cooperates with the multiple degree of freedom sample stage 116 to facilitate the positioning of the mechanical testing instrument 1402 relative to the sample stage surface 208 within the microscope chamber 102 shown in FIG. 1.

As shown in FIG. 11, the testing assembly 1400 includes the mechanical testing instrument 1402, such as an indenter, scratching instrument, tensile instrument, sensor, observation tool and the like. In one example the mechanical testing instrument 1402 includes a modular instrument configured for selective coupling with a stage 1408. For instance, the mechanical testing instrument 1402 includes, but is not limited to, a high load and a low load indenter wherein the high load mechanical testing instrument 1402 is configured to provide much larger indentation forces to a sample compared to the low load mechanical testing instrument. As shown in FIG. 11, each of the mechanical testing instruments 1402 includes an instrument shaft 1404 coupled with a transducer or sensor positioned within the mechanical testing instrument. Each of the mechanical testing instruments 1402 further includes an instrument tip 1406 configured for engagement with and interaction with a sample on the sample stage surface 208.

In one example, the mechanical testing instrument 1402 includes a plurality of modular replaceable transducers configured to provide varying forces and displacement ranges for the instrument tip 1406. For instance, in one example the mechanical testing instrument 1402 includes the low load transducer configured for 10 milli-Newtons of force and actuation of plus or minus 15 microns of bidirectional electrostatic actuation. In another example, the mechanical testing instrument 1402 includes another transducer, for instance, the high load transducer (described above) configured for maximum forces of at least 30 milli-Newtons with at least 80 microns worth of travel in the direction of the sample stage surface 208 provided by actuation stage 1408. Optionally, a variety of selectable load cells are available for one or more of the high or low load transducers that provide varying force ranges and sensitivity.

The stage 1408 (e.g., a stage providing linear movement along the Y axis) as described herein on the mechanical testing instrument linear stage 210 (providing linear movement along the X axis) provides a supplemental means or an alternative means for engaging the instrument tip 1406 or indenting the instrument tip 1406 into the sample on the sample stage surface 208. Stated another way, the stage 1408 is configured to provide the actuation force, for instance, the force for indenting the instrument tip 1406 into the sample on the sample stage surface 208. The stage 1408 in one example is configured to provide displacement of the test instrument while the mechanical testing instrument 1402 including a transducer therein is configured to detect the force applied to the sample stage surface 208 as well as the displacement of the instrument tip 1406 upon engagement with the sample according to operation of the stage 1408.

Referring now to FIG. 12, one example of the stage 1408 is shown in detail with the mechanical testing instrument 1402 removed. As shown in FIG. 12 the stage 1408 includes a stage base 1500A and a stage platform 1500B movably coupled with the stage base 1500B. As shown, the stage platform 1500B is movably coupled relative to the stage base 1500A, for instance with flexural springs 1512. An actuator, such as a piezo actuator 1502, is coupled between the stage base 1500A and the stage platform 1500B. The piezo actuator 1502 cooperates with the flexural springs 1512 to guide the stage platform 1500B along a linear axis (e.g., an X, Y or Z axis dependent on the orientation of the stage 1408). In the example shown in FIG. 12, the stage 1408 guides movement of the stage platform 1500B along a linear Y axis (e.g., toward the sample stage surface 208). The stage 1408 for positioning and actuating the mechanical testing instrument 1402 includes, but is not limited to, linear drive stages having stepper motors, piezo actuators or motors, voicecoil actuators, stick-slip actuators and the like. The stage 1408 includes, but is not limited to, one or more linear stages manufactured and sold by Physik Instrumente GmbH & CO. of Germany; Dynamic Structures and Materials, LLC of Franklin Tenn.; Attocube Systems AG of Germany; SmarAct GmbH of Germany; and PiezoSystem Jena GmbH of Germany. One example of the stage 1408 is a flexural stage provided by Dynamic Structures and Materials, LLC. The operation of the stage 1408, for instance one or more of the stages provided above, moves the stage platform 1500B relative to the stage base 1500A in a guided, controlled manner that substantially ensures that the motion of the mechanical testing instrument 1402 (see FIG. 11) is in a linear direction and not otherwise tilted, canted, or the like relative to the desired linear axis of movement.

In another example the stage 1408 includes a displacement sensor 1514 configured to measure the displacement of the stage platform 1500B. The displacement sensor 1514 is thereby able to cooperate with the transducer of the mechanical testing instrument 1402 to measure the displacement of the stage platform 1500B and the corresponding displacement of the mechanical testing instrument 1402, as well as its instrument tip 1406 during operation of the testing assembly 1400. In one example, upon engagement of the instrument tip 1406 with a sample on the sample stage surface 208, the force measurement through the transducer in the mechanical testing instrument 1402 begins to rise. When coupled with the displacement measurements of the displacement sensor 1514, the force measurements and displacement measurements of the respective transducer of the mechanical testing instrument 1402 and the displacement sensor 1514 are together used to determine one or more mechanical properties of the sample on the sample stage surface 208. In another example, the stage 1408 includes an electrical socket 1516 configured to operate the actuator 1502 as well as receive measurements from the displacement sensor 1514 and interface those measurements with a processor and user interface configured for displaying such information.

Operation of the Testing Assembly

Referring again to FIG. 2, the testing assembly 112 is shown with the multiple degree of freedom sample stage 116 and the mechanical testing instrument 114 positioned on a testing assembly platform 200. As previously described, in one example, the multiple degree freedom sample stage 116 includes both a linear stage assembly 204 and a rotation and tilt stage assembly 206. The linear stage assembly 204 and the rotation and tilt stage assembly 206 are configured to move the sample stage surface 208 including, for instance, a sample thereon within a region within a microscope assembly, for instance, a localized coincidence region such as the region 222 shown in FIG. 2.

In one example, the localized coincidence region 222 is defined by the working regions of the instruments, such as the instruments 104, 106, 108, 110 shown in FIG. 2. Operation of the testing assembly 112 begins with the sample stage surface 208 as shown. For instance, the sample stage surface 208 is shown at a substantially orthogonal angle to the mechanical testing instrument 114 including, for instance, the instrument shaft 406 and the instrument tip 408 previously shown in FIG. 4. In this orientation the mechanical testing instrument 114 is configured to indent or scratch the sample present on the sample stage surface 208. In this particular configuration one of the instruments 104-110 is similarly configured to contemporaneously observe or interact with the sample on the sample stage surface 208 while the mechanical testing instrument 114 performs one or more mechanical tests on the sample.

In another example, where it is desirable to move the sample stage surface 208, for instance, to orient the sample relative to another instrument within the multi-instrument assembly 100 the multiple degree of freedom sample stage 116 is operated to orient the sample stage surface 208 and the sample thereon relative to the desired instrument. The testing assembly 112, for instance the linear stage assembly 210 of the mechanical testing instrument 114, is similarly operated to position the mechanical testing instrument 114 in alignment with at least a portion of the sample to allow for in situ contemporaneous mechanical testing of the sample while the sample is observed or interacted with by one or more of the instruments 104-110.

Figure 13A:
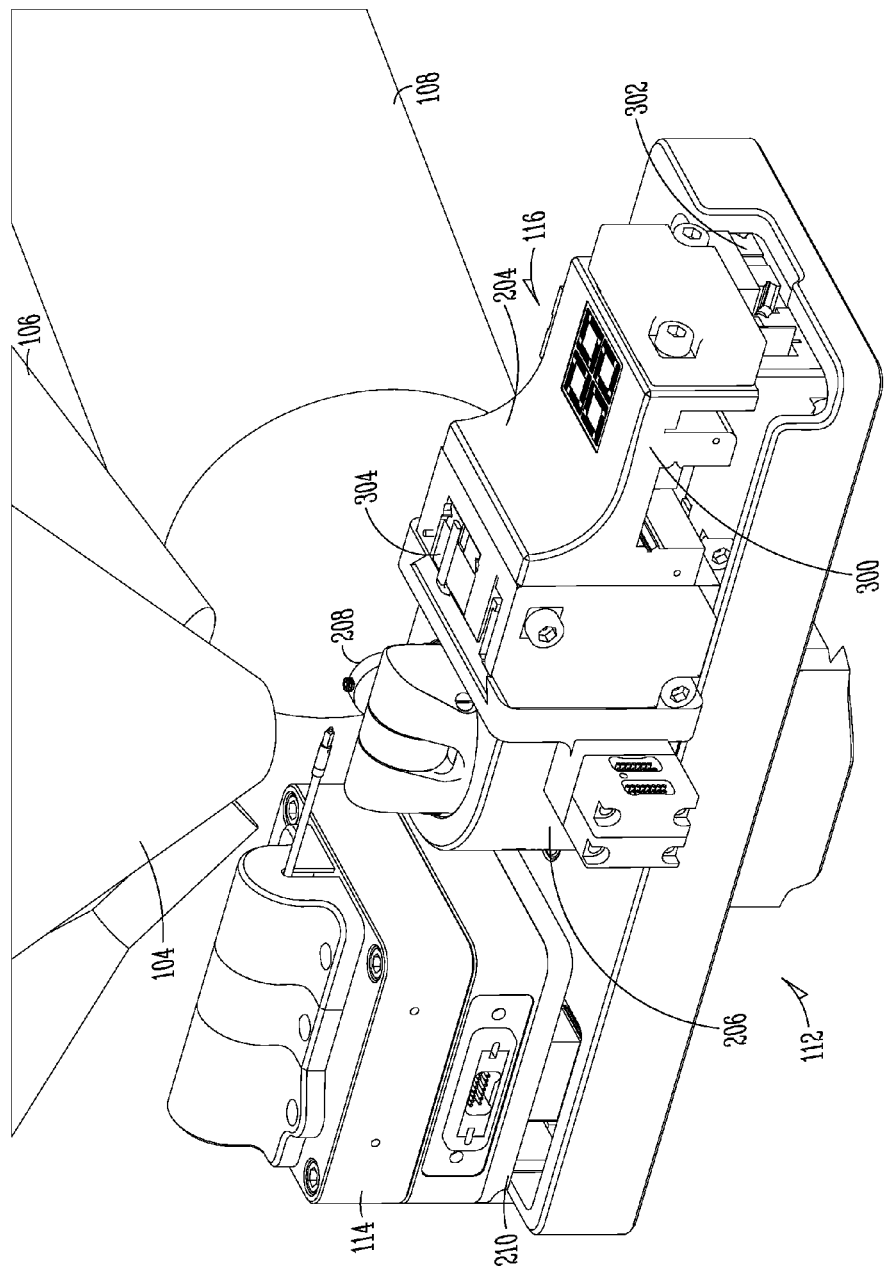
FIG. 13A is an isometric view of the testing assembly of FIG. 2 with a sample stage surface in a second orientation.

Referring now to FIG. 13A, the sample stage surface 208 is shown oriented in a second configuration relative to the first configuration shown in FIG. 2. As shown, the sample stage surface 208 is positioned in a substantially orthogonal position to the position shown in FIG. 2. For instance, the rotation and tilt stage assembly 206, in one example, including the rotation stage 600 is operated to move the sample stage surface 208 into the substantially orthogonal orientation shown. As similarly shown in FIG. 13A, in another example, the tilt stage 602 (shown in FIG. 6) is operated to tilt or orient the sample stage surface 208 in a slightly elevated orientation to the substantially vertical orientation shown in FIG. 2. Stated another way, the planar surface of the sample stage surface 208 is oriented at a tilted angle relative to the orientation shown in FIG. 2. In one example, as shown in FIG. 13A, the orienting of the sample stage surface 208 as well as the sample thereon is conducted to position the sample in an orientation directed toward one of the instruments, such as the third instrument 108 including, for instance, a second electronic back scatter detector (EBSD).

In another example, the linear stage assembly 204 including, for instance, the X, Y and Z linear stages 300, 302, 304 are operated through the actuators 301 to linearly position the sample stage surface 208, coupled with the linear stage assembly 204 by way of the rotation and tilt stage assembly 206, relative to one or more of the instruments 104-110. Stated another way, the linear stage assembly 204 is configured to elevate and translate the sample stage surface 208 relative to the first position shown in FIG. 2. That is to say, the linear stage assembly 204 is configured to move the sample stage surface 208 into and out of the page, to the left and right of the page, and vertically (upwardly or downwardly) relative to the page as shown in FIG. 13A.

Figure 13B:
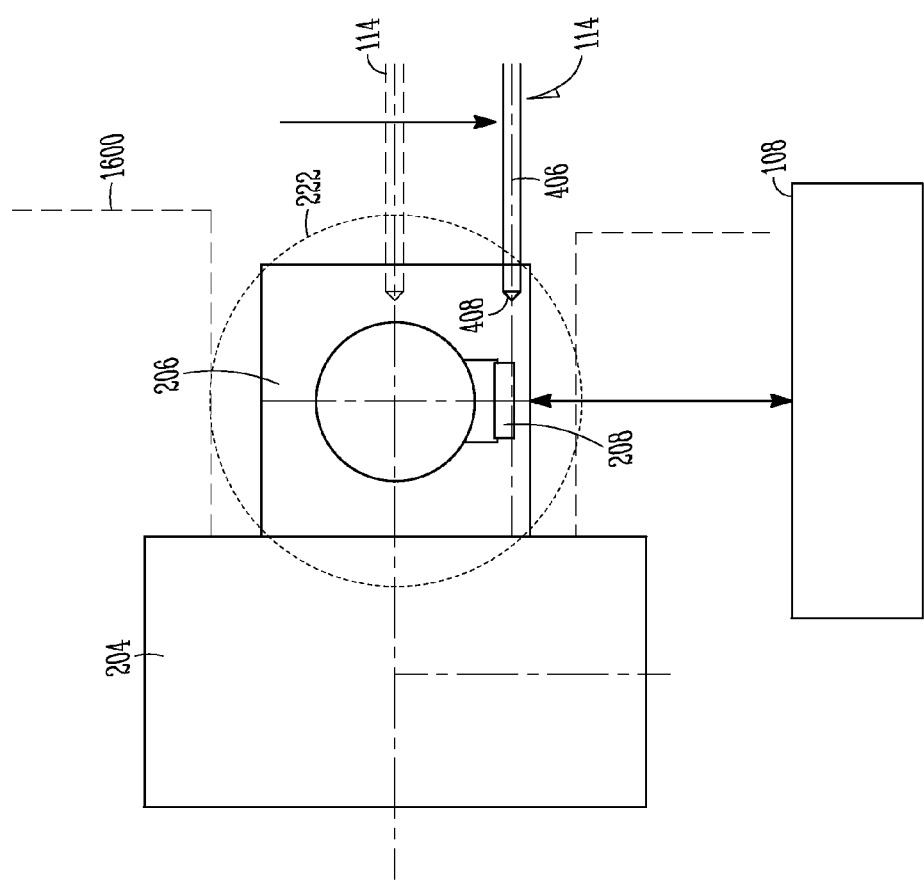
FIG. 13B is a schematic view of the testing assembly in FIG. 13A in the second orientation.

Referring now to FIG. 13B, a schematic representation of the testing assembly 112 previously shown in FIGS. 2 and 13A is provided showing the sample stage surface 208 in the orientation provided in FIG. 13A. Stated another way, the sample stage surface 208 is rotated from the orientation shown in FIG. 2 and tilted according to operation of the rotation and tilt stage assembly 206 including, for instance, the rotation stage 600 and the tilt stage 602. As shown in the example in FIG. 13B, the sample stage surface 208 is oriented in the new orientation shown in FIG. 13A, for instance to orient the sample on the sample stage surface 208 with the instrument 108. As previously described, the combination of the linear stage assembly 204 including the X, Y and Z stages 300-304 and the rotation and tilt stage assembly 206 including the rotation and tilt stages 600, 602 provides the flexibility desired for the sample stage surface 208 to be oriented in substantially any orientation directed to or usable with any one of the instruments 104-110 as previously described herein. Additionally, in at least some examples, the orientation of the sample stage surface 208 allows for the contemporaneous use of the mechanical testing instrument 114 with the sample on the sample stage surface 208 while the sample is observed or interacted with by any one of the instruments 104-110.

In the example shown in FIG. 13B, an instrument composite footprint 1600 is shown in phantom lines extending around at least a portion of the sample stage surface 208. As previously described, in one example, the instruments such as the instruments 104-110 are tightly clustered around the sample stage surface 208, for instance due to space constraints within a multiple instrument assembly 100 as previously shown in FIG. 1. Because of the space constraints the linear stage assembly 204 and the rotation and tilt stage assembly 206 work in concert to flexibly position and orient the sample stage surface 208 in any of a plurality of positions to accordingly orient the sample on the sample stage surface with respect to any of the one or more of the instruments 104-110. That is to say the linear stage assembly 204 and the rotation and tilt stage assembly 206 cooperate to position and orient the sample stage surface 208 within a localized coincidence region optionally defined at least in part by the instrument composite footprint 1600.

In some examples, it is desired to not only orient the sample stage surface 208 with one or more of the instruments 104-110 but to also align a portion of the sample on the sample stage surface 208 with, for instance, the mechanical testing instrument 114. The alignment of the sample on the sample stage surface 208 with the mechanical testing instrument 114 as well as one or more of the instruments 104-110 allows for the contemporaneous mechanical testing with the instrument 114 and observation or interaction with the sample by one or more of the instruments 104-110. As shown in FIG. 13B, with rotation of the sample stage surface 208, for instance from the orientation originally shown in FIG. 2, the sample stage surface 208 is not only rotated relative to the instrument 108 but it is also rotated relative to the mechanical testing instrument 114 shown in the original position in FIG. 13B with dashed lines. In one example, the testing assembly 112 includes a fixed mechanical testing instrument 114 sized and shaped to be positioned at the orientation shown in phantom lines in FIG. 13B. As shown, in order for the sample stage surface 208 to align with the mechanical testing instrument 114 as positioned, the linear stage assembly 204 must be operated to recess the sample stage surface 208 (upward along the page) to align the sample stage surface 208 with the mechanical testing instrument 114 while at the same time positioning the sample relative to the instrument 108 for one or more of observation or analysis. Positioning of the sample stage surface 208 in the orientation shown in FIG. 13B (i.e., not recessed) is desirable for at least two reasons. In one example, by recessing the sample stage surface 208 away from the instrument 108, for instance to align the sample stage surface 208 with the fixed mechanical testing instrument 114, the sample on the sample stage surface 208 is positioned outside of or at the edge of the working region of the instrument 108 thereby frustrating observation with the instrument 108 if contemporaneous mechanical testing is also desired. Accordingly, it is desirable to move the sample stage surface 208 and the sample thereon into coincidence with the working region of the instrument 108 within the localized coincidence region 222 while at the same time aligning the mechanical testing instrument 114 with the sample on the sample stage surface 208 for mechanical testing. Providing the linear stage assembly, such as the linearly stage assembly 210 shown in FIG. 13A, facilitates positioning of the mechanical testing instrument 114 in the orientation shown in FIG. 13B. That is to say, the mechanical testing instrument 114 is aligned with the sample stage surface 208 while at the same time the sample stage surface 208 is positioned within the working region of the instrument 108.

Additionally, it is advantageous to move the mechanical testing instrument 114 in the manner shown to facilitate the continued positioning of the sample stage surface 208 including, for instance, the rotation and tilt stage assembly 206 outside of an instrument footprint 1600. As shown in FIG. 13B, the instrument footprint 1600, in one example, extends around at least a portion of the localized coincidence region 222. As previously described, the instruments, such as the instruments 104-110, provide a clustered series of instruments around the sample stage surface 208 and the components of the multiple degree of freedom sample stage 116 thereby crowding the region and accordingly requiring the flexible positioning of the sample stage surface 208, for instance, with the combination of the linear stage assembly 204 and the rotation and tilt stage assembly 206. Where alignment of the sample stage surface 208 with the mechanical testing instrument 114 is desired along with interaction and observation by the instruments 104-110 it becomes important to provide additional degrees of freedom to facilitate the alignment of the mechanical testing instrument 114 with the sample stage surface 208. For instance, as shown in FIG. 13B, without movement of the mechanical testing instrument 114 (the mechanical testing instrument as shown by the dashed lines when fixed) the recessing of the sample stage surface 208 would position at least the rotation and tilt stage assembly 206 in an intercepting configuration with the instrument footprint 1600. Stated another way, at least the rotation and tilt stage assembly 206 would collide with the instruments within the instrument footprint 1600 when the sample stage surface 208 is aligned with the mechanical testing instrument 114 and positioned relative to the instrument 108 for observation by the instrument.

By providing the linear stage actuator 210 (e.g., an X axis actuator) shown in FIG. 13A, one or more of the linear stage assembly 204 and the linear stage assembly 210 of the mechanical testing instrument 114 may be operated alone or together to position the sample stage surface 208 and the mechanical testing instrument 114 to not only orient the sample stage surface 208 relative to the instrument 108 but also at the same time align the sample stage surface 208 with the mechanical testing instrument 114. This added flexibility (in addition to the Y axis linear movement provided by the stage 1408) allows for the alignment of the mechanical testing instrument 114 with the sample stage surface 208 in substantially any orientation where the sample stage surface 208 is oriented with respect to any of the instruments 104-110, for instance while the sample stage surface 208 is rotated approximately 180 degrees from an upward direction and a downward direction where the downward direction is shown in FIG. 13B and the upward direction would be 180 degrees opposite from the orientation shown in FIG. 13B.

Referring again to FIG. 13B, to maintain the orientation of the sample stage surface 208 within the localized coincidence region 222 and thereby avoid collision with the instruments formed by the instrument footprint 1600 the rotation and tilt stage assembly 206 is moved with the linear stage assembly 204, for instance, with one or more of the stage actuators 300-304 while at the same time the mechanical testing instrument 114 is moved as shown in FIG. 13B. Stated another way, the mechanical testing instrument 114 is moved a first linear direction, for instance, downwardly along the page as shown in FIG. 13B and the rotation and tilt stage assembly 206 is moved upward relative to the instrument 108 to align the sample stage surface 208 with the mechanical testing instrument 114 while at the same time orienting the sample stage surface 208 within the working region of the instrument 108. By combining the linear translation of the sample stage surface 208, for instance by the linear stage assembly 204, and the linear stage assembly 210 of the mechanical testing instrument the overall translation of each of the components such as the mechanical testing instrument 114 and the sample stage surface 208 is substantially minimized thereby maintaining the rotation and tilt stage assembly 206 and the surface 208 safely within the instrument footprint 1600. The multiple degree of freedom sample stage 116 as well as the mechanical testing instrument 114 are thereby able in combination (or separately in the case of the multiple degree of the freedom sample stage 116 operated by itself) to thereby flexibly position the sample stage surface 208 in one or more orientations within the localized coincidence region 222 without colliding the sample stage surface 208 (or any of the stages described herein) with any of the instruments shown by the instrument footprint 1600 formed by the instruments 104-110 previously shown in FIG. 2.

The addition of the linear stage assembly 210 of the mechanical testing instrument 114 provides enhanced flexibility to thereby enable the alignment of the mechanical testing instrument 114 with the sample stage surface 208 in substantially any orientation of the sample stage surface 208 relative to the instruments 104-110. Further, the provision of the linear stage assembly 210 with the mechanical testing instrument 114 provides enhanced flexibility to the overall system by minimizing the overall translation needed for the rotation and tilt stage assembly 206 while at the same time allowing for alignment of the mechanical testing instrument 114 with the sample stage surface 208 as the sample on the sample stage is otherwise oriented within the working region of one or more of the instruments 104-110.

Further, as shown herein, the combination of the linear stage assembly 204 with the rotation and tilt stage assembly 206 provides a system configured to move the sample stage surface 208 around the mechanical testing instrument 114. Stated another way, with a static (or movable) instrument 114 the rotation and tilt stage assembly 206 in combination with the linear stages of the assembly 204 ensures the sample stage surface 208 is movable around at least the tip of the instrument including, but not limited to, positions on either side of the tip (left, right, below and above), in front of the tip (e.g., with the end of the tip point orthogonal to the surface 208), and a near infinite variety of positions therebetween. Conversely, the mechanical testing instrument 114 is able to access and engage with the sample stage surface 208 from a variety of angles according to the coordinated operation of one or more of the rotation and tilt stage assembly 206 and the linear stage assembly 204 (and optionally, the stages associated with the mechanical testing instrument 114).

Positioning and Locking of a Sample Position with the Multiple Degree of Freedom Sample Stage As previously described above, the multiple degree of freedom sample stage 116 provides substantial flexibility for the positioning of the sample stage surface 208 and a sample thereon relative to one or more of the instruments 104-110 while at the same time allowing for access by the mechanical testing instrument 114. The movable coupling of each of the stage platforms with respective stage bases for each of the stages of the linear stage assembly 204 and the rotation and tilt assembly 206 provides an opportunity to undesirably introduce tolerances to the overall multiple degree of freedom sample stage 116. Such tolerances include lateral displacement and tilting tolerances that allow movement of the sample stage surface 208 after or during positioning that misalign the sample stage surface 208 and the sample thereon relative to one or more of the instruments 104-110 and a mechanical testing instrument 114. Tolerances frustrate the accurate and reliable testing of a desired testing location of the sample.

As previously described herein, one or more cross roller bearing assemblies 706 as well as the clamping assemblies as described herein, such as the clamping assembly 1100 for the rotation stage 600, the clamping assembly 1208 for the tilt stage 600, as well as the clamping provided through the linear stages 210, 300, 302, 304 substantially minimizes any inaccuracies caused by tolerances and allows for the accurate and reliable positioning of any sample on the sample stage surface 208. Stated another way, even with the flexibility provided by the multiple degree of freedom sample stage 116 robust supporting surfaces, clamping and locking engagement, and the like are provided throughout the multiple degree of freedom sample stage 116 to ensure a sample on the sample stage surface 208, when positioned at a desired position, is accurately and reliably positioned at the desired position and thereafter held or locked in that position despite actuation or interaction with instruments such as the mechanical testing instrument 114. That is to say, forces incident on the sample stage surface 208, for instance, from the mechanical testing instrument 114 engaged with the sample stage surface 208 as well as environmental forces such as gravity incident on the stages of the multiple degree of freedom sample stage 116 have minimal effect on the positioning and retention of the sample stage surface 208 and the sample thereon relative to the desired position.

Figure 14:
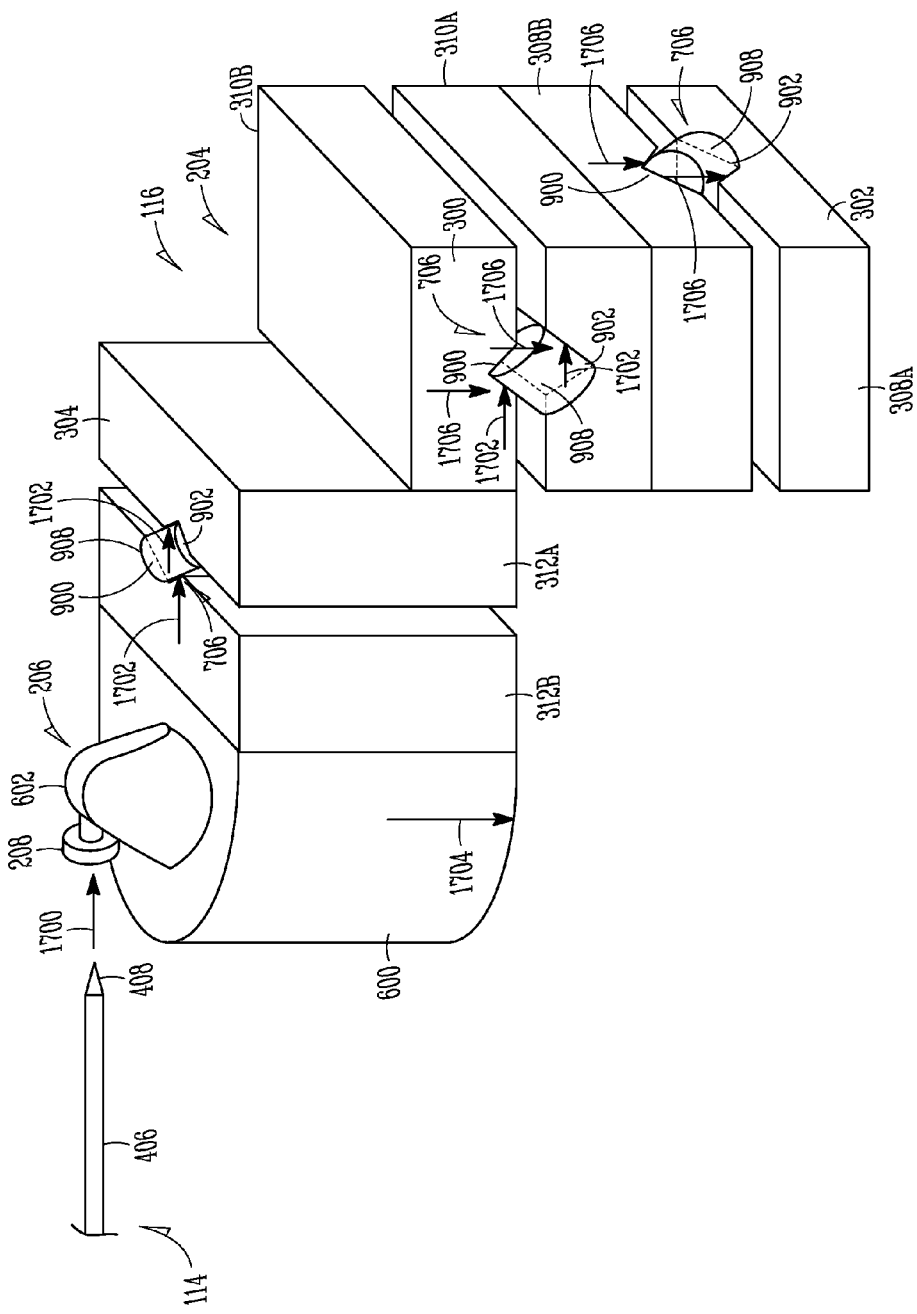
FIG. 14 is a schematic view of an example of the multiple degree of freedom sample stage including force vectors applied and transmitted through the sample stage.

Referring now to FIG. 14, a schematic example of the multiple degree of freedom sample stage 116 is provided. As shown, the multiple degree of freedom sample stage 116 includes a linear stage assembly 204 and a rotation and tilt stage assembly 206. As previously described, in one example, the linear stage assembly 204 includes a plurality of linear stages such as X, Y and Z stages 300-304. The linear stages 300-304 allow for the linear positioning of the sample stage surface 208 (including for instance, the rotation and tilt stage assembly 206) into one or more translated orientations as previously described herein. As shown in FIG. 14, in one example, each of the X, Y and Z stages 300-304 includes corresponding cross roller bearing assemblies 706. As shown in FIG. 14, one cross roller bearing assembly is provided between each of the stage platforms and stage bases of each of the X, Y and Z stages 300-304. In other examples and as shown herein, two or more cross roller bearing assemblies 706 are provided for each of the X, Y and Z stages 300-304 to provide enhanced support and minimize tolerances (e.g., deflection, tilting and the like of the stage platforms relative to the stage bases).

As shown, each of the cross roller bearing assemblies 706 includes a plurality of roller bearings 908 positioned within the first and second rail channels 900, 902. As previously described herein, the roller bearings 908 provide surface to surface interfaces between the stage bases and stage platforms of each of the X, Y and Z stages 300-304. The roller bearings 908 are provided in an alternately crossed configuration within the first and second rail channels 900, 902. As shown, for instance in FIG. 7, the opposed pairs of interface surfaces, for instance, 906A, 906B and 904A, 904B allow the stage platforms and stage bases to interface in surface to surface contact with the roller bearings 908 therebetween. For instance, the rolling interfaces of the roller bearings 902 are received in planar contact along each of the interface surfaces 904A, B and 906A, B to support and transmit forces, torques and the like through surface contact between the roller bearings 908 and the opposed stage platforms and stage bases. This surface to surface engagement between the stage platforms and the stage bases with the intervening roller bearings 908 substantially prevents the deflection or tilting of the stage platforms relative to the stage bases and thereby provides a robust supported interface between the stage platforms and stage bases of each of the X, Y and Z stages 300-304. The robust support at the same time allows for ready movement of the stage platforms relative to the stage bases through guidance provided by the cross roller bearing assemblies 706 when translation of one or more of the stages (e.g., to orient the sample stage surface 208) is desired.

In the schematic example shown in FIG. 14, one or more forces such as an instrument force 1700 and gravity 1704 are applied to the multiple degree of freedom sample stage 116 to illustrate the robust supporting features of the sample stage 116 during operation. As shown in FIG. 14, the stages 300-304 and 600, 602 are oriented to position the sample stage surface 208 in a substantially orthogonal orientation relative to the instrument shaft 406 and instrument tip 408 of the mechanical testing instrument 114. The engagement of the mechanical testing instrument 114 with the sample stage surface 208 applies the instrument force 1700 including corresponding moments to the components of the multiple degree of freedom sample stage 116. To ensure the sample stage surface 208 and the sample thereon are maintained in the desired position (e.g., to ensure accurate placement of the instrument tip 408 at the desired testing location) the entire chain of components of the multiple degree of freedom sample stage 116 from the sample stage surface 208 to the stage base 308A of the Y stage 302 must remain substantially static from the time positioning is finished through at least the instrument testing procedure. As described below, the components of the multiple degree of freedom sample stage 116 ensure that the sample is accurately and precisely moved during positioning and reliably held in a static specified position and orientation (e.g., locked, clamped, held in place, and the like) during interaction with the mechanical testing instrument 114. Minimizing deflection of the sample and/or mechanical testing instrument 114 due to compliance in the stage and/or platform assembly reduces error and uncertainty in the mechanical test procedure. Further the multiple degree of freedom sample stage reliably holds the sample in the desired position and orientation for post-interaction observation of the sample, for instance, by one or more of the instruments 104-110.

As shown in FIG. 14, the instrument force 1700 is applied to the sample stage surface 208. Optionally, the instrument force 1700 is applied in an opposed fashion, for instance during tensile testing. The clamping assemblies 1110 and 1208 for the respective rotation and tilt stages 600, 602 clamp the components of the rotation and tilt stage assembly 206 in the orientation shown in FIG. 14. For instance, as described above multiple points of contact are engaged with the spindle assemblies of each of the rotation and tilt stages 600, 602 to substantially prevent the movement of the spindles (e.g., stage platforms) relative to the respective stage bases. The instrument force 1700 is thereby transmitted from the rotation and tilt stage assembly 206 to the adjacent Z stage 304 without moving the components of the rotations tilt stages 600, 602 from their respective static orientations.

As shown in FIG. 14, the instrument force 1702 is transmitted through the linear stage assembly 204 as described herein. The instrument force 1702 is applied to the roller bearings 908 from the stage platform 312B by surface to surface engagement of the first rail channel 900 with the roller bearings 908. The roller bearings 908 transmit the instrument force 1702 to the second rail channel 902 (e.g., to the opposed interface surface as shown in FIG. 7). The instrument force 1702 is thereafter transmitted to the stage platform 310B of the X stage 300 and through the interface of the first rail channel 900 is transmitted to the roller bearings 908 of the cross roller bearing assembly 706 of the X stage 300. The roller bearings 908 of the cross roller bearing assembly 706 transmit the instrument force 1702 to the opposed rail channel 902 of the stage base 310A of the X stage 300. As shown in FIG. 14, the stage base 310A of the X stage 300 is coupled with the stage platform 308B of the Y stage 302. As shown in FIG. 14, because the cross roller bearing assembly 706 is aligned with the vector of the instrument force 1700 as well as the transmitted instrument force 1702 the cross roller bearing assembly 706 provides minimal support to the Y stage 302 against movement. Instead, the clamping or locking engagement provided by the linear stage 302 (e.g., with the actuator 301) previously shown in FIG. 3 statically fixes the stage platform 308B relative to the stage base 308A. Accordingly, the instrument force 1700 including the transmitted instrument force 1702 is transmitted through the multiple degree of freedom sample stage 116 through one or more of clamping and locking assemblies that substantially prevent the movement of the associated components and through surface to surface engagement between the respective stage platforms and stage bases of each of the X, Y and Z stages 300-304 to provide robust supported engagement between the respective components that substantially prevents the movement of the components relative to one another.

In another example, other forces (e.g., with different directional vector components) are incident on the multiple degree of freedom sample stage 116. In one example, a force such as gravity 1704 and associated moments created by gravity are applied to one or more of the components of the multiple degree of freedom sample stage 116. Gravity in combination with interaction forces provided by the mechanical testing of the instrument 114 (e.g., indentation, scratching, or tensile forces) deflects components of other stages that provide tolerances. The robust supporting features of each of the components of the multiple degree of freedom sample stage 116 substantially prevents the tilting or deflection of the sample stage surface 208 even with the multiple degrees of freedom provided. For instance, as shown in FIG. 14, gravity 1704 is indicated with an arrow applied through the rotation stage 600. As with the instrument force 1700, the force of gravity 1704 is similarly applied to each of the components of the multiplied degree of sample stage 116, for instance, each of the stage platforms and stage bases of respective stages 300-304 and 600, 602. For instance, gravity at each of the components is transmitted (e.g., a transmitted force of gravity 1706) to one or more of the components from adjacent components. Obviously each of the components is subject to gravity individually as well. For the purpose of this illustration gravity 1704 is only examined as a force transmitted from one end to the other end of the stage 116.

As shown, for instance, in FIG. 14, the force of gravity 1704 is incident on the rotation stage 600. The force of gravity 1704 as well as the associated force of gravity incident on the stage platform 312B of the Z stage 304 creates a corresponding moment to the multiple degree of freedom sample stage 116. The clamping or locking engagement of the linear Z stage 304 (e.g., through the actuator 301) substantially prevents the movement of the stage platform 312B relative to the stage base 312A. Stated another way, tilting, deflection and the like of any of the components of the associated Z stage 304, for instance, by way of gravity 1704 is substantially prevented by the clamping and reliable locking of the stage platform relative to the stage base. Continuing down the chain of components as shown in FIG. 14, the transmitted force of gravity 1706 is transmitted through the cross roller bearing assembly 706 associated with the X stage 300 for instance, by surface to surface contact between the first and second rail channels 900, 902 and the interposing roller bearings 908. For instance, the transmitted force of gravity 1706 is applied across the first rail channel 900 to the alternating crossed roller bearings 908 of the cross roller bearing assembly 706 associated with the X stage 300. The transmitted force of gravity 1706 from the stage platform 310B is transmitted to the stage base 310 by the engagement of the alternatingly cross roller bearings 908 engaged along the interface surfaces of the second rail channel 902. As shown in FIG. 14, the transmitted force of gravity 1706 is thereby applied to the second rail channel 902.

The force of gravity 1706 is thereafter applied to the Y stage 302, for instance, the stage platform 308B. The transmitted gravity force 1706 is applied to the alternating cross roller bearings 908 from the first rail channel 900. The transmitted force of gravity 1706 is transmitted across the roller bearings 908 to the interface surfaces of the second rail channel 902. As shown in FIG. 14, the force of gravity 1704 as well as moments resulting from gravity are substantially prevented from generating deflection of the components of the multiple degree of freedom sample stage 116. Stated another way, the clamping or locking features associated with each of the linear stages 300-304 (e.g., the actuators 301) as well as the cross roller bearing assemblies 706 substantially prevent the deflection of the components of the linear stage assembly 204. That is to say, with positioning of the sample stage surface 208 and a sample thereon in a desired orientation and position, the application of forces such as from the mechanical testing instrument 114 and environmental forces such as gravity (but also including vibration, equipment movement and the like) generate substantially no deflection, tilting and the like of any of the components of the multiple degree of freedom sample stage 116. Stated another way, the sample stage surface 208 and the sample thereon when positioned as desired are substantially locked in that orientation and robustly supported by the components of the multiple degree of freedom sample stage 116 to ensure a desired testing location of the sample is held at a desired location, for instance for interaction with the mechanical testing instrument 114 and one or more of the instruments 104-110.

Figure 15:
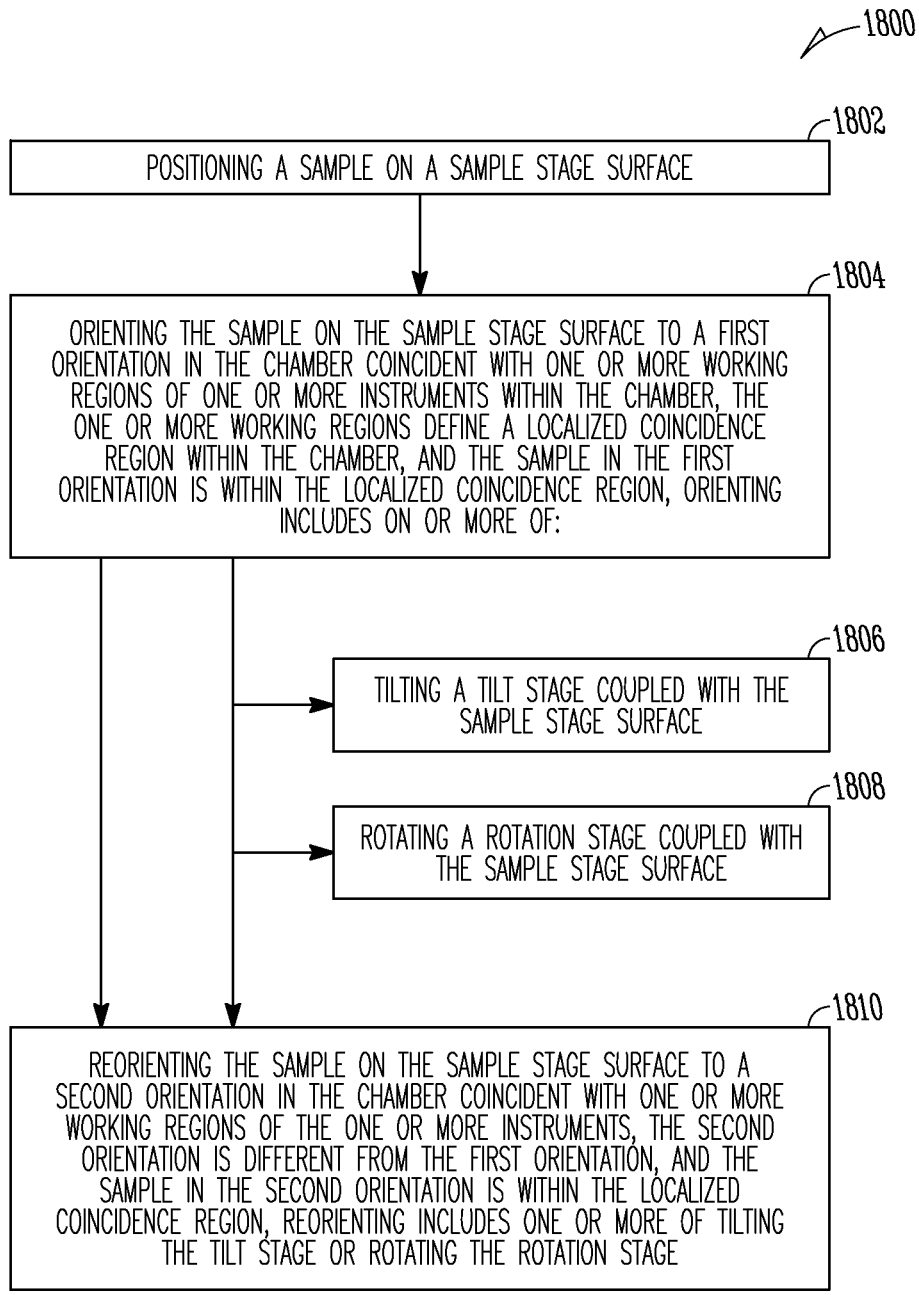
FIG. 15 is a block diagram showing one example of a method for orienting a sample within a chamber of a multi-instrument assembly using the multiple degree of freedom sample stage assembly.

Method for Positioning a Sample within a Chamber of a Multi-Instrument Assembly FIG. 15 shows one example of a method 1800 for orienting a sample within a chamber of a multi-instrument assembly (such as a multi-instrument microscope assembly) using the multiple degree of freedom sample stage 116 described herein. In describing the method in 1800, reference is made to one or more components, features, functions and the like previously described herein. Where convenient reference is made to the components and features with reference numerals. The reference numerals provided are exemplary and are not exclusive. For instance, the features, components, functions and the like described in the method 1800 include the corresponding numbered elements other corresponding features described herein (both numbered and unnumbered) as well as their equivalents.

At 1802, a sample is positioned on a sample stage surface such as the sample stage surface 208 shown in FIG. 2. At 1804, the sample on the sample stage surface 208 is oriented to the first orientation in the chamber such as a chamber 102 of the multi-instrument assembly 100 shown in FIG. 1. In the first orientation the sample on the sample stage surface 208 is oriented with one or more working regions of one or more instruments, such as the instruments 104-110 within the chamber 102. As described herein, the working regions are formed at least, in part, by the instrument axis and focal points 214-220 shown in FIG. 2 which in turn when consolidated form a composite localized coincidence region 222. Orienting the sample on the sample stage surface 208 to the first orientation in the chamber 102 coincident with one or more of the working regions of one or more of the instruments 104-110 includes positioning and orienting the sample within the localized coincidence region 222 formed by the working regions. The sample on the sample stage surface 208 in the first orientation is within the localized coincidence region 222. For instance, the sample on the sample stage surface 208 in one or more orientations within the localized coincidence region 222 is within a clustered space between one or more of the instruments 104-110 shown in FIGS. 1 and 2, for instance.

Orienting the sample includes one or more of, for instance tilting a tilt stage 602 coupled with the sample stage surface 608 at step 1806 or rotating a rotation stage 600 coupled with the sample stage surface 208 at step 1808. In one example, orienting includes one or more of tilting and rotation of the corresponding tilt stage 602 and the rotation stage 600.

At 1810, the method 1800 includes reorienting the sample on the sample stage surface 208 to a second orientation in the chamber 102 coincident with one or more working regions of the one or more instruments 104-110. The second orientation is different from the first orientation (e.g., a second orientation relative to the same instrument or a second orientation directed toward a second instrument) in the sample. The second orientation is within the localized coincidence region 222. Reorienting includes one or more of tilting the tilt stage 602 or rotating the rotation stage 600 as previously described herein. In another example, the method 1800 includes coupling a testing assembly platform, such as the platform 200 shown in FIG. 2 supporting the sample stage surface 208 and the rotation and tilt stages 600, 602, to a mounting stage 101 of the multi-instrument assembly 100. The mounted testing assembly 112 is recessed from the walls of the multi-instrument assembly 100 as shown in FIG. 1. Stated another way, the testing assembly 112 is positioned centrally or in another example away from the walls of the multi-instrument assembly to enhance the flexibility of positioning of the multiple degree of freedom sample stage 116 with respect to one or more of the instruments 104-110 tightly clustered around the sample stage surface 208.

Several options for the method 1800 follow. In one example, orienting the sample on the sample stage surface 208 to the first orientation and reorienting the sample to the second orientation including orienting the sample on the sample stage surface to the first orientation coincident with the first working region of a first instrument (such as one of the instruments 104-110) of the one or more instruments having the one or more working regions. Reorienting the sample on the sample stage surface 208 includes orienting the sample on the sample stage surface 208 to the second orientation coincident with the first working region on the first instrument. Stated another way, in one example, orienting and reorienting includes adjusting the position and alignment of the sample position on the sample stage surface 208 (as well as the alignment of the sample stage surface 208) within the same working region of a single instrument. For instance, the sample stage surface and the sample thereon are positioned in one example orthogonal to the axis of the first instrument. In another example, the sample stage surface 208 and the sample thereon are positioned in an alignment coincident with the axis. That is to say, the axis of the instrument is directed along the surface of the sample stage surface 208.

In another example, orienting the sample on the sample stage surface to the first orientation includes orienting the sample of the sample stage surface 208 to the first orientation coincident with the first working region of a first instrument of the one or more instruments 104-110 having one or more working regions. Reorienting the sample on the sample stage surface 208 includes orienting the sample stage surface 208 and the sample thereon to the second orientation coincident with a second working region of a second instrument, such as the instrument 106 of the one or more instruments 104-110 having one or more working regions different from the working region of the first instrument.

In still another example, at least one of orienting and reorienting the sample stage surface 208 includes linearly moving the sample stage surface with one or more linear stages 300-304 coupled with the rotation and tilt stages. As described herein, in one example, the one or more linear stages 300-304 are included in a linear stage assembly 204 shown, for instance, in FIG. 2. Optionally, the method 1800 including orienting and reorienting of the sample stage surface 208 includes constraining movement of the sample stage surface and one or more of the tilting and rotation stages 602, 600 toward one or more of the instruments 104-110 in the chamber 102 with linear translation of the one or more linear stages 300-304. For instance, the linear stages 300-304 are operated to maintain the sample stage surface 208 within the localized coincidence region while also precluding collision with one or more of the instrument 104-110. That is to say, the linear stages 300-304 maintain the sample stage surface 208 in a substantially centralized location away from the instrument composite footprint 1600. Constraining movement of the sample stage surface 208 and one or more of the tilt and rotation stages 602, 600 includes moving a mechanical testing instrument 114, for instance, with a linear stage actuator 210 in an opposed direction to the linear translation of the one or more stages (as shown in FIG. 13B). The mechanical testing instrument 114 is configured to mechanically interact with a sample of a sample stage surface in one or more of the first and second orientations.

In yet another example, linearly moving the sample stage surface 208 includes moving a stage platform (e.g., one or more of 308B, 310B, 312B) relative to a stage base (one or more of 308A, 310A, 312A) with an actuator 301. The actuators 301 include, but are not limited to, piezo motors, stepper motors, voice coil actuators, stick-slip actuators and the like. Optionally, the method 1800 includes clamping one or more of the stage platforms relative to the respective stage bases (e.g., of one or more of the linear stages 300, 302, 304) with a clamping or locking feature operated by the actuator 301.

In still other examples, the method 1800 including, for instance, orienting and reorienting of the sample stage surface 208 includes moving a mechanical testing instrument 114 into alignment with the sample on the sample stage surface 208 in at least the first and second orientations. For instance, moving the mechanical testing instrument 114 includes operating a linear stage actuator (e.g., one or more of a X, Y or Z axis linear stage actuator 210) coupled with the mechanical testing instrument 114. As described herein, moving the mechanical testing instrument 114 in combination with orientation of the sample stage surface 208 (e.g., orienting the sample stage surface in one or more disparate orientations through linear translation, rotation and tilting of the sample stage surface 208) allows for alignment of the mechanical testing instrument with the sample stage surface in substantially any orientation relative to the instruments 104-110 while at the same time minimizing the overall movement of the sample stage surface 208. Minimizing the overall movement (especially translation) of the sample stage surface 208 correspondingly minimizes any opportunity for collision of the multiple degree of freedom the sample stage 116 with one or more of the instruments 104-110 tightly clustered around the stage 116.

Optionally, one or more of tilting the tilt stage 602 or rotating the rotation stage 600 includes actuating first motor elements 1104A of motors (for instance, of motors 1102A-C) in a first direction wherein the motors include the first motor element 1104A and a second motor element 1104B. Actuating of the first motor elements 1104A of the motors 1102A, 1102B (and optionally, 1102C) includes simultaneous actuation of the first motor element 1104A of the first motor 1102A and of the first motor element 1104A of the second motor 1102B to rotate the rotation stage platform in the first direction relative to the rotation stage base (e.g., 1108B relative to 1108A). Similarly, through operation of the first motor elements 1204A of the first and second motors 1202A, 1202B the tilt stage platform 1010B is rotated relative to the tilt stage base 1010A as shown in FIG. 10A.

Similarly, one or more of tilting of the tilt stage or rotating of the rotation stage 600, 602 includes actuating second motor elements, for instance second motor elements 1204B of the motors 1202A, 1202B, in a second direction opposed to the first direction. Actuating of the second motor elements 1204B, 1204B of the motors 1202A, 1202B includes simultaneous actuation of the second motor element of the first motor 1202A and the second motor element of the second motor 1202B to rotate the tilt stage platform 1010B in a second direction relative to the tilt stage base 1010A. Referring to FIG. 9, actuation of the second motor elements 1104B of at least two of the motors 1102A-C, for instance, by simultaneous actuation of the second motor elements 1104B moves the rotation stage platform 1010B relative to the rotation stage base 1008A.

Method for Locking a Stage of Stage Assembly

Figure 16:
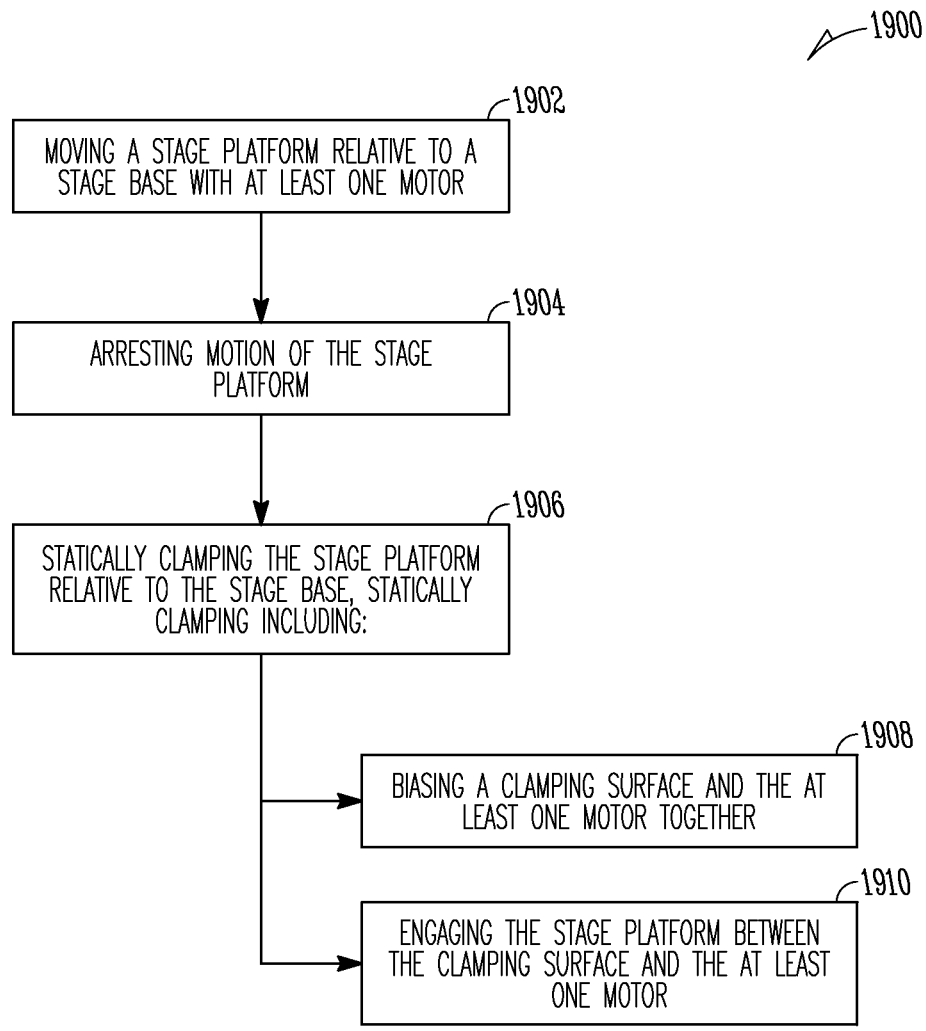
FIG. 16 is a block diagram showing one example of a method for locking a stage of a sample stage assembly in an orientation.

FIG. 16 shows one example of the method 1900 for locking a stage of a sample stage assembly in an orientation (e.g., in an orientation or position as previously described herein). In describing the method 1900 reference is made to one or more components, features, functions and the like previously described herein. Where convenient reference is made to the components and features with reference numerals. The reference numerals provided are exemplary and are not exclusive. For instance, the features, components, functions and the like described in the method 1900 include the corresponding numbered elements, other corresponding features described herein, as well as their equivalents.

At 1902, a stage platform is moved relative to a stage base with at least one motor. For instance, as described herein, multiple linear, rotation and tilt stages 300-304, 600, 602 are described. Each of the stages includes respective stage platforms and stage bases. As described herein, one or more motors are operated to move the stage platforms relative to the stage bases. At 1904, the method 1900 includes arresting motion of the stage platform relative to its respective stage base. Optionally, the method 1900 includes moving the testing assembly 112, for instance by operation of actuators associated with the multi-instrument assembly 100. Actuation by the assembly 100, for instance transmitted through the interface of the mounting stage 101 with the testing assembly mount 202 provides additional flexibility for movement of the stage platform (e.g., the sample stage surface 208).

At 1906, the method 1900 includes statically clamping the stage platform relative to the stage base. For instance, examples of clamping assemblies are shown in FIGS. 9 and 10A including clamp assemblies 1110 and 1208. Respective stage platforms 1008B and 1010B are shown in FIGS. 9 and 10A and corresponding stage bases 1008A and 1010A are shown in FIGS. 9 and 10A as well. Static clamping includes one or more of the following. At 1908, a clamping surface and the at least one motor are biased together, for instance, by operation, of one or more actuators, springs and the like as described herein. At 1910, the stage platform is engaged between the clamping surface and the at least one motor. In one example, the clamping surface is shown in FIG. 9 by at least one portion of the rotational bearing 1014. Another example of a clamping surface is shown in FIG. 10A by the axle 1200 (see also FIG. 10B a cross-sectional view of the tilt spindle assembly 1020 including the axle 1200 extending therethrough). Examples of motors are similarly provided in FIGS. 9 and 10A corresponding to features 1102A-1102C and 1202A, 1202B, respectively.

In one example, the at least one motor described in the method 1900 includes a piezo motor configured to provide at least one way directional movement of the stage platform relative to the stage base. For instance, as shown in FIG. 9 the motors 1102A-C each include separate motor elements 1104A, 1104B (first and second motor elements) configured to provide rotational movement in opposed first and second directions. In one example, arresting motion of the stage platform such as stage platform 1008B relative to the stage base 1008A includes relaxing the at least one motor, for instance, each of the motor elements 1104A, 1104B. In another example, the method 1900 incorporates arresting motion of the stage platform, for instance, by relaxation of the at least one motor with clamping of the stage platform 1008B relative to the stage base 1008A. Optionally, as previously described herein the relaxation of one or more of the motor elements 1104A, 1104B of each of the motors 1102A, 1102C (or their counterparts in the tilt stage 602) automatically initiates static clamping of the stage platform 1008B relative to the stage base 1008A.

Several options for the method 1900 follow. In one example, biasing the clamping surface and the at least one motor together includes biasing at least one motor such as one or more of the motors 1102A, 1102C with at least one biasing element 1114A, 1114B coupled with the at least one motor. The at least one motor 1102A-C is biased toward the clamping surface such as a portion of the rotational bearing 1014. In another example, as shown in FIG. 10A the biasing elements 1212A, 1212B (shown in FIG. 10B) bias the motors 1202A, 1202B toward the clamping surface such as the axle 1200. In another example, biasing the at least one motor includes applying a first bias to a first motor element, such as the motor element 1104A shown in FIG. 9 of at least one of the motors 1102A, with a first spring element 1114A of the at least one biasing element. A second bias is applied to a second motor element, such as the motor element 1104B of the at least one motor 1102A, with a second spring element 1114B of the at least one biasing element wherein the first motor element 1104A is configured to move the stage platform in a first direction and the second motor element 1104B is configured to move the stage platform in a second direction, for instance, opposed to the first direction. Optionally, moving the stage platform such as the stage platform 1008B or 1010B relative to the respective stage bases includes moving one or more drive shoes, such as the drive shoes 1106, 1206 shown in FIGS. 9, 10A, with one or more of the first and second motor elements previously described herein. As shown in the figures, the drive shoes 1106, 1206 are respectively coupled between the first and second motor elements of each of the motors.

In still another example, the method 1900 further includes constraining lateral deflection of the at least one biasing element such as the biasing elements 1212A, 1212B shown in FIGS. 10A, 10B with at least one lateral support biasing element 1214A, 1214B. The at least one lateral support biasing element 1214A, 1214B is coupled with the at least one biasing element 1212A, 1212B. Optionally, the lateral support biasing elements are coupled with the biasing elements with an intervening structure, such as the motor support saddle 1206 shown in FIG. 10A.

Referring now to FIG. 9, in one example, biasing the clamping surface and the at least one motor together includes biasing at least one motor (for instance, three motors 1102A-1102C) positioned around the stage platform 1008B toward a first surface of the stage platform, for instance, a surface of the stage platform engaged with one or more of the drive shoes 1106 as shown in FIG. 9. Engaging the stage platform 1008B includes engaging the one or more motors 1102A-C with the first surface and engaging the clamping surface (for instance, a portion of the rotational bearing 1014 shown in FIG. 10A) with a second surface of the stage platform opposed to the first surface. In one example, the stage platform 1008B includes a rotation flange 1100 associated with the stage platform 1008B, and the rotation flange 1100 includes the first and second opposed surfaces as shown in FIG. 9. For instance, as shown the first and second surfaces of the rotation flange 1100 are shown respectively engaged with the drive shoes 1106 and a portion of the rotational bearing 1014.

In still yet another example, biasing the clamping surface and the at least one motor together includes biasing at least two motors 1202A, 1202B spaced around the stage platform 1010B toward a first surface of the stage platform such as an outer perimeter of a tilt spindle 1020 shown in FIGS. 10A and 10B. Similarly, engaging the stage platform 1010B includes engaging the at least two motors 1202A, B with the first surface such as the outer perimeter surface of the tilt spindle 1020 and engaging the clamping surface such as the axle 1200 with the second surface of the stage platform opposed to the first surface. For instance, as shown in FIG. 10B, the axle 1200 is engaged with an inner perimeter surface of the tilt spindle 1020. As shown in FIG. 10B, the tilt spindle 1020 is a portion of the tilt stage platform 1010B and includes the first surface extending along an outer perimeter of the tilt spindle and the second surface extending along an inner perimeter of the tilt spindle.

Operation of a Cross Roller Bearing Assembly

Figure 17:
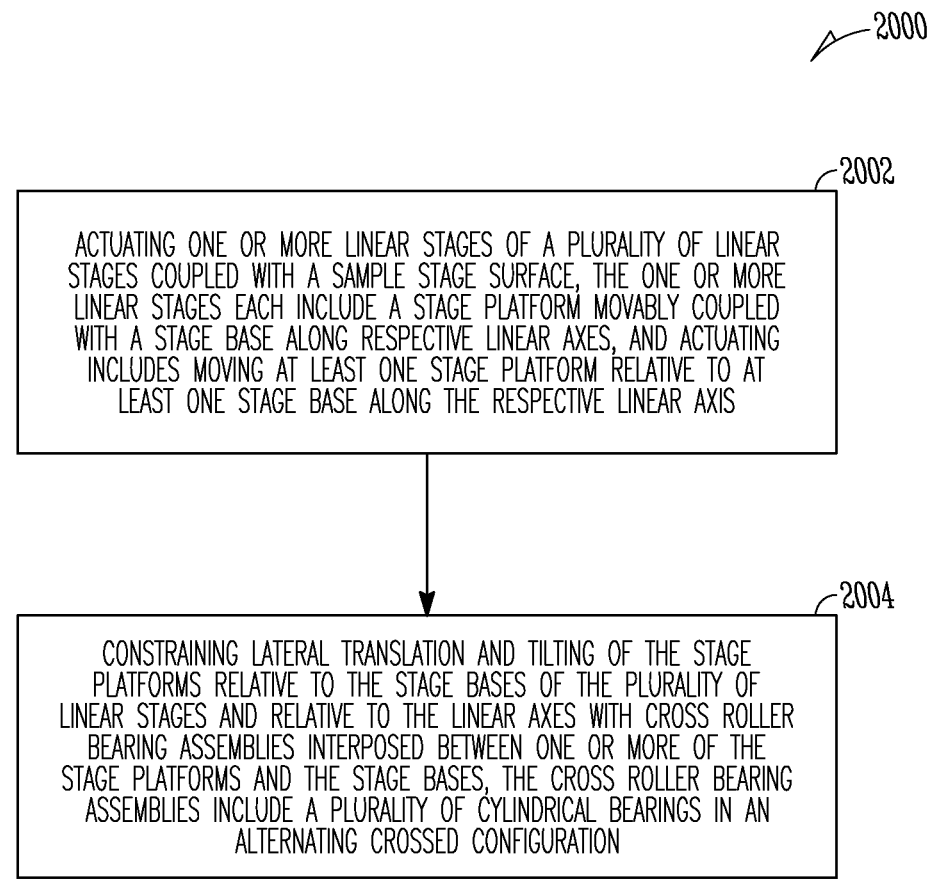
FIG. 17 is a block diagram showing one example of a method for using a multiple degree of freedom sample stage including a plurality of linear stages.

FIG. 17 shows one example of a method 2000 for using a multiple degree of freedom sample stage, such as the sample stage 116 shown in FIGS. 1 and 2. In describing the method 2000, reference is made to one or more components, features, functions, and the like previously described herein. Where convenient reference is made to the components and features with reference numerals. Reference numerals provided are exemplary and are not exclusive. For instance, the features, components, functions, and the like described in the method 2000 include the corresponding numbered elements, other corresponding features described herein (both numbered and unnumbered) as well as their equivalents.

At 2002, the method 2000 includes actuating one or more linear stages 300-304 of a plurality of linear stages coupled with a sample stage surface 208. The one or more linear stages 300-304 each include a stage platform moveably coupled with a stage base along respective linear axes (e.g., x, y, and z axes). Actuating includes moving at least one stage platform relative to the at least one stage base along the respective linear axis for one or more of the linear stages 300-304. As shown, for instance, in FIG. 3, each of the linear stages 300-304 each include corresponding stage bases 308A, 310A, 312A and stage platforms 308B, 310B, 312B. Each of the stage platforms are movable with respect to the corresponding stage bases of the associated linear stages 300-304, for instance with actuators 301 associate with each of the stages. Optionally, actuating the one or more linear stages 300-304 includes aligning the sample stage surface 208 with one or more instruments including a mechanical testing instrument 114.

At 2004, the method 2000 further includes constraining lateral translation and tilting of the stage platforms relative to the respective stage bases of the plurality of linear stages 300-304 and relative to the linear axis of each of the stages with cross roller bearing assemblies 706 interposed between one or more of the stage platforms and the stage bases. As described herein, the cross roller bearing assemblies 706 include a plurality of cylindrical bearings (e.g., roller bearings 908) in an alternating crossed configuration. For instance, each adjacent roller bearing 908 within a cross roller bearing assembly 706 is at a right angle relative to the adjacent roller bearings on either side of that bearing.

Referring now to FIG. 7, in one example constraining lateral translation and tilting of the stage platforms included engaging platform planar interface surfaces that of 904A, 906B (of the rail channel 900) with cylindrical bearing surfaces of the plurality of cylindrical bearings 908, (e.g., cylindrical bearing surfaces 910 shown in FIG. 7). Further, constraining lateral translation and tilting includes engaging base planar interface surfaces of the stage base, such as 906A, 904B (of the rail channel 902) with the cylindrical bearing surfaces 910 of the plurality of cylindrical bearings 908. In another example, constraining lateral translation and tilting includes engaging opposed pairs of platform and base planar interface surfaces with cylindrical bearing surfaces of the plurality of cylindrical bearings 908. For instance, a first array of cylindrical bearing surfaces 910, for instance, a cylindrical bearing oriented in a first direction (see the left bearing 908 shown in FIG. 7) are engaged with a first pair of the opposed pairs of platform and base planar interface surfaces 904A-904B. Similarly, a second array of cylindrical bearing surfaces 910 are engaged with a second pair of the opposed pairs of platform and base planar interface surfaces, such as the surfaces 904A, 904B as shown with the right bearing 908 in FIG. 7.

As previously described herein, each of the rail channels 900, 902 containing a plurality of roller bearings 908 therein includes roller bearings in an alternating crossed relationship. For instance, as previously described herein, the roller bearing 908 as shown in FIG. 7 includes its cylindrical bearing surface 910 engaged with each of the pair of opposed interface surfaces 904A, 904B. A preceding or succeeding roller bearing 908 within the rail channels 900, 902 includes a second array of cylindrical bearing surfaces 910 engaged with the second pair of the opposed pairs of platform and base planar interface surfaces such as the interface surfaces 906A, 906B. As shown in FIG. 7, the first pair of interface surfaces 904A, 904B are at an angle to the second pair of interface surfaces 906A, 906B corresponding to the alternating crossed configuration of the cylindrical bearings. Stated another way, the rail channels 900, 902 of each of the stage platforms and stage bases include opposed interface surfaces 904A, 904B and 906A, 906B sized and shaped to engage surface to surface contact with corresponding cylindrical bearing surfaces 910 of each of the plurality of roller bearings 908.

Several options for the method 2000 follow. In one example, constraining lateral translation and tilting further includes guiding the movement of at least one of the stage platforms, such as stage platform 310B shown in FIG. 7, relative to at least of the respective stage bases 310A along the respective linear axis of one of the linear stages of the plurality of linear stages 300-304 with one of the cross roller bearer assemblies 706. As described herein, the cross roller bearing assemblies 706 substantially prevent or constrain the lateral translation and tilting of the stage platforms relative to the respective stage bases where the translation and tilting are not coincident with the stage linear axis. The cross roller bearing assemblies 706 thereby provide a solid continuous chain of surface-to-surface engagement from the sample stage surface 208 throughout the multiple degree of freedom sample stage 116. Additionally, the cross roller bearing assembly 706 ensure that translation of the stage platforms, such as the stage platforms 308B, 310B, 312B are constrained to move along the respective linear axes of the respective linear stages 300-304 according to the interfacing relationship of the roller bearings 908 within the assembly 706 as they are correspondingly movably engaged with the respective stage bases 308A, 310A, 312A. The cross roller bearing assemblies 706 thereby substantially prevent deflection and tilting of the linear stages 300-304 while at the same time the cross roller bearing assemblies 706 accurately and reliably guide the translation of the plurality of stage platforms relative to the respective stage bases along the desired linear axes.

In yet another example, actuating the one or more linear stages 300-304 includes moving one or more of the stage platforms 308B, 310B, 312B relative to the respective stage bases, for instance with actuators 301 associated with each of the stages 300-304. In one example, the actuators 301 include, but are not limited to, piezo motors, stepper motors, voice coil actuators, stick-slip actuators and the like.

In still another example, the method 2000 includes aligning the sample stage surface 208 with one or more instruments such as the mechanical testing instrument 114 with the actuation of one or more of the linear stages 300-304 of the linear stage assembly 204 previously shown in FIGS. 2 and 3. Optionally, aligning the sample stage surface with one or more instruments 114 includes one or more of rotating or tilting the sample stage surface 208 with one or more rotation or tilt stages 600, 602 coupled with the plurality of linear stages 300-304. For instance, the rotation or tilt stages 600, 602 are incorporated into a rotation and tilt stage assembly 206 that is coupled in series with the plurality of linear stages and the linear stage assembly 204.

CONCLUSION

The apparatus and methods described herein provide a system configured for positioning a sample for observation and mechanical interaction and testing within a compact chamber of an instrument housing. The chamber of such an instrument housing includes a series of instruments and detectors (e.g., FIB instruments, one or more electron back scatter detectors (EBSD), an electron gun for a scanning electron microscope and the like) tightly clustered around a centralized testing location as well as the physical boundaries of the instrument housing walls.

The testing assembly apparatus and methods described herein allow for flexible maneuvering of the sample within the tight cluster of instruments by with the multiple degree of freedom sample stage. The testing assembly uses a multiple degree of freedom sample stage including linear, rotation and tilt stages to accurately, reliably and quickly position and reposition a sample within the chamber according to the testing parameters (e.g., working regions, such as focal points, instrument ranges and the like) of each of the instruments used successively or at the same time. Further, the positioning and orienting of the sample occurs within the centralized location (localized coincidence region) of the compact chamber surrounded by the clustered instruments and the detectors. The combination of rotation, tilt and linear positioning facilitates the orienting and positioning of a sample at the centralized location according to the working regions of the one or more instruments. Moreover, the positioning and repositioning of the sample is performed without opening of the chamber and manual repositioning.

In another example, the testing assembly includes one or more stages coupled with a mechanical testing instrument (e.g., a transducer including an indentation, scratch tip, tensile grips or the like) to provide at least one additional degree of freedom to the testing assembly. For instance, a sample that is tilted and rotated to direct the sample toward a first instrument is retained in close proximity to the centralized location of the compact chamber defined by the focal points or working distances (e.g., the working regions) of the one or more instruments and detectors as well as their physical housings. The mechanical testing instrument is similarly positionable relative to the sample to mechanically test the sample. The testing assembly thereby positions and orients the sample according to the parameters of each of the instruments originally present within the compact chamber of the instrument housing while at the same time positioning a mechanical testing instrument to interact with the sample. Moving the mechanical testing instrument maintains the sample in the desired orientation of the instruments and detectors, allows for their use and also allows for contemporaneous mechanical testing of the sample.

As described herein, the multiple degree of freedom sample stage (and in some examples the mechanical testing instrument) allows for the positioning and orienting of a sample within a centralized location (e.g., localized coincidence region) of the compact chamber and substantially prevents impingement or collision of the multiple degree of freedom sample stage with the instruments and detectors tightly clustered around the centralized location.

Moreover, the testing apparatus, for instance the linear stage assembly including one or more of X, Y and Z stages includes one or more bearing assemblies with substantially rigid lateral support and linear guidance mechanisms. In one example, the one or more bearing assemblies include, but are not limited to, cross roller bearing assemblies for one or more of the linear stages that provide a solid structural interface between each stage platform and stage base. The surface to surface engagement between the cylindrical bearing surfaces and the opposed interface surfaces substantially eliminates relative movement of the components of each linear stage along axes not coincident with the linear axes of the respective stages. Additionally, one or more of the rotation and tilt stages includes clamping assemblies that affirmatively hold the stage platform of each actuator static relative to the respective stage base. The clamping assemblies bias the stage platform into engagement with the stage base with multiple points of contact to tightly hold the stage platform in the desired position. Even with engagement by the mechanical testing instrument with the sample (e.g., indenting, scratching, tensile loading and the like) and corresponding transmission of forces to the multiple degree of freedom sample stage, the sample is reliably held in the desired position and orientation for testing and observation. The multiple degree of freedom stage is thereby able to provide the flexibility of the linear, tilt and rotation positioning without the compounded tolerances provided in other multiple degree of freedom assemblies.

VARIOUS NOTES & EXAMPLES

Example 1 can include subject matter such as an apparatus, such as can include a testing assembly configured for operation within a chamber of a multi-instrument assembly, each instrument of the multi-instrument assembly includes a working region, the working regions defining a localized coincidence region, the testing assembly comprising: a testing assembly platform configured for coupling with a mounting stage of the multi-instrument assembly; a mechanical testing instrument coupled with the testing assembly platform, the mechanical testing instrument is configured to engage and test a sample on a sample stage surface; a multiple degree of freedom sample stage assembly coupled with the testing assembly platform, the multiple degree of freedom sample stage includes: the sample stage surface, a plurality of linear stages coupled in series with the testing assembly platform, a rotation stage, and a tilt stage, wherein the rotation and tilt stages are coupled in series and are coupled between the sample stage surface and the plurality of linear actuators; and wherein the multiple degree of freedom sample stage is configured to orient the sample stage surface to each of the working regions in the localized coincidence region through a combination of movement of two or more of the plurality of linear, rotation and tilt stages.

Example 2 can include, or can optionally be combined with the subject matter of Example 1, to optionally include wherein the rotation stage includes a rotation stage platform movably coupled with a rotation stage base, and the tilt stage includes a tilt stage platform movably coupled with a tilt stage base.

Example 3 can include, or can optionally be combined with the subject matter of one or any combination of Examples 1 or 2 to optionally include comprising a rotation and tilt assembly including the rotation and tilt stages, wherein the rotation and tilt assembly is coupled with the plurality of linear stages, and the rotation and tilt assembly includes: the rotation stage base coupled with the plurality of linear stages, a rotation spindle movably coupled with the rotation stage base, and the rotation spindle includes the rotation stage platform and the tilt stage base, and a tilt spindle movably coupled with the rotation spindle.

Example 4 can include, or can optionally be combined with the subject matter of one or any combination of Examples 1 through 3 to optionally include wherein the rotation stage base surrounds the tilt stage base.

Example 5 can include, or can optionally be combined with the subject matter of one or any combination of Examples 1 through 4 to optionally include wherein the rotation stage includes one or more motors interposed between the rotation stage platform and the rotation stage base, and the one or more motors are biased into direct or indirect engagement with one or more of the rotation stage platform or base.

Example 6 can include, or can optionally be combined with the subject matter of one or any combination of Examples 1 through 6 to optionally include wherein the tilt stage includes one or more motors interposed between the tilt stage platform and the tilt stage base, and the one or more motors are biased into direct or indirect engagement with one or more of the tilt stage platform or base.

Example 7 can include, or can optionally be combined with the subject matter of one or any combination of Examples 1 through 6 to optionally include wherein at least one of the rotation stage and the tilt stage includes one or more motors, and each of the one or more motors includes: a first motor element configured to move one of the rotation stage platform or the tilt stage platform in a first direction relative to the respective rotation stage base or the tilt stage base, a second motor element configured to move one of the rotation stage platform or the tilt stage platform in second direction relative to the respective rotation stage base or the tilt stage base, wherein the second direction is opposed to the first direction, and a drive shoe coupled between the first and second motor elements, the drive shoe is movably engaged with one of the rotation or tilt stage platforms or the rotation or tilt stage bases.

Example 8 can include, or can optionally be combined with the subject matter of one or any combination of Examples 1 through 7 to optionally include wherein the rotation and tilt stages are positioned at an end of the plurality of linear stages remote from the location of coupling between the testing assembly platform and the plurality of linear stages, and rotation and tilting of the sample stage surface is localized near the end of the plurality of linear stages.

Example 9 can include, or can optionally be combined with the subject matter of one or any combination of Examples 1 through 8 to optionally include wherein the multiple degree of freedom sample stage assembly is isolated from walls of a chamber of a multi-instrument assembly.

Example 10 can include, or can optionally be combined with the subject matter of one or any combination of Examples 1 through 9 to optionally include wherein the tilt stage includes a tilting range of motion, and the rotation stage includes a rotation range of motion, and the tilt and rotation stages are movable throughout the respective tilting and rotation ranges of motion while the sample stage surface is oriented to each of the working regions in the localized coincidence region.

Example 11 can include, or can optionally be combined with the subject matter of one or any combination of Examples 1 through 10 to optionally include wherein the tilting range of motion is around 180 degrees, and the rotation range of motion is around 180 degrees.

Example 12 can include, or can optionally be combined with the subject matter of one or any combination of Examples 1 through 11 to optionally include wherein at least one linear stage of the plurality of linear stages includes a stage platform movably coupled with a stage base.

Example 13 can include, or can optionally be combined with the subject matter of one or any combination of Examples 1 through 12 to optionally include wherein the stage platform of a first stage of the plurality of linear stages is included in the stage base of a second stage of the linear stages.

Example 14 can include, or can optionally be combined with the subject matter of one or any combination of Examples 1 through 13 to optionally include wherein at least one cross roller bearing assembly is coupled between the stage platform and the stage base of one or more of the plurality of linear stages.

Example 15 can include, or can optionally be combined with the subject matter of one or any combination of Examples 1-14 to include, subject matter such as a method, such as can include positioning a sample on a sample stage surface; orienting the sample on the sample stage surface to a first orientation in the chamber coincident with one or more working regions of one or more instruments within the chamber including a mechanical testing instrument, the one or more working regions define a localized coincidence region within the chamber, and the sample in the first orientation is within the localized coincidence region, orienting includes one or more of: tilting a tilt stage coupled with the sample stage surface, or rotating a rotation stage coupled with the sample stage surface; and reorienting the sample on the sample stage surface to a second orientation in the chamber coincident with one or more working regions of the one or more instruments, the second orientation is different from the first orientation, and the sample in the second orientation is within the localized coincidence region, reorienting includes one or more of tilting the tilt stage or rotating the rotation stage.

Example 16 can include, or can optionally be combined with the subject matter of one or any combination of Examples 1 through 15 to optionally include, wherein orienting the sample on the sample stage surface to the first orientation and reorienting the sample on the sample stage surface to the second orientation respectively include: orienting the sample on the sample stage surface to the first orientation coincident with a first working region of a first instrument of the one or more instruments having the one or more working regions, and reorienting the sample on the sample stage surface to the second orientation coincident with the first working region of the first instrument.

Example 17 can include, or can optionally be combined with the subject matter of one or any combination of Examples 1 through 16 to optionally include wherein orienting the sample on the sample stage surface to the first orientation and reorienting the sample on the sample stage surface to the second orientation respectively include: orienting the sample on the sample stage surface to the first orientation coincident with a first working region of a first instrument of the one or more instruments having one or more working regions, and reorienting the sample on the sample stage surface to the second orientation coincident with a second working region of a second instrument of the one or more instruments having one or more working regions.

Example 18 can include, or can optionally be combined with the subject matter of one or any combination of Examples 1 through 17 to optionally include wherein at least one of orienting and reorienting includes linearly moving the sample stage surface with one or more linear stages coupled with one or more of the rotation and tilt stages.

Example 19 can include, or can optionally be combined with the subject matter of one or any combination of Examples 1 through 18 to optionally include wherein orienting and reorienting includes constraining movement of the sample stage surface and one or more of the tilt and rotation stages toward one or more of the instruments in the chamber with linear translation of the one or more linear stages.

Example 20 can include, or can optionally be combined with the subject matter of one or any combination of Examples 1 through 19 to optionally include wherein constraining movement of the sample stage surface and one or more of the tilt and rotation stages includes moving the mechanical testing instrument in an opposed direction to the linear translation of the one or more linear stages, the mechanical testing instrument is configured to mechanically interact with a sample on the sample stage surface.

Example 21 can include, or can optionally be combined with the subject matter of one or any combination of Examples 1 through 20 to optionally include wherein orienting the sample on the sample stage surface to the first orientation includes one or more of: tilting a tilt stage coupled with the sample stage surface, or rotating a rotation stage coupled with the sample stage surface, and rotating the sample stage surface around a sample surface rotational axis extending through the sample stage surface; and reorienting the sample on the sample stage surface to the second orientation includes one or more of tilting the tilt stage or rotating the rotation stage, and rotating the rotation stage coupled with the sample stage surface.

Example 22 can include, or can optionally be combined with the subject matter of one or any combination of Examples 1 through 21 to optionally include wherein at least one of orienting and reorienting includes moving the mechanical testing instrument into alignment with the sample on the sample stage surface in at least the first and second orientations.

Example 23 can include, or can optionally be combined with the subject matter of one or any combination of Examples 1 through 22 to optionally include wherein moving the mechanical testing instrument includes operating a linear stage actuator coupled with the mechanical testing instrument.

Example 24 can include, or can optionally be combined with the subject matter of one or any combination of Examples 1 through 23 to optionally include coupling a testing assembly platform including the sample stage surface and the rotation and tilt stages to a mounting stage of the multi-instrument assembly, and the mounted testing assembly platform is recessed from walls of the multi-instrument assembly.

Example 25 can include, or can optionally be combined with the subject matter of one or any combination of Examples 1 through 24 to optionally include wherein one or more of tilting the tilt stage or rotating the rotation stage includes: actuating a first motor element of a first motor in a first direction, wherein the first motor includes the first motor element and a second motor element, actuating a first motor element of a second motor in the first direction, wherein the second motor includes the first motor element and a second motor element, and wherein actuation of the first motor element of the first motor is simultaneous with actuation of the first motor element of the second motor to rotate in the first direction one or more of the tilt stage platform relative to the tilt stage base or the rotation stage platform relative to the rotation stage base.

Example 26 can include, or can optionally be combined with the subject matter of one or any combination of Examples 1 through 25 to optionally include wherein one or more of tilting of the tilt stage or rotating of the rotation stage includes: actuating the second motor element of the first motor in a second direction, wherein the second direction is opposed to the first direction, actuating the second motor element of the second motor in the second direction, and wherein actuation of the second motor element of the first motor is simultaneous with actuation of the second motor element of the second motor to rotate in the second direction one or more of the tilt stage platform relative to the tilt stage base or the rotation stage platform relative to the rotation stage base.

Example 27 can include, or can optionally be combined with the subject matter of one or any combination of Examples 1 through 26 to optionally include wherein at least one of orienting and reorienting includes linearly translating the sample stage surface with one or more linear stages coupled with one or more of the rotation and tilt stages.

Example 28 can include, or can optionally be combined with the subject matter of one or any combination of Examples 1-27 to include, subject matter such as an apparatus, such as can include a rotation stage; a tilt stage coupled with the rotation stage; a sample stage surface coupled with one of the rotation stage or the tilt stage; and wherein one or both of the rotation and tilt stages includes: a stage base, a stage platform coupled with the stage base, and at least one motor movably coupled with one of the stage base or the stage platform, the at least one motor is configured to move the stage platform relative to the stage base; and wherein one or both of the rotation and tilt stages includes a clamping assembly, the clamping assembly comprising: a clamping surface extending along the stage platform, and at least one biasing element coupled with at least one of the motor and the clamping surface, wherein the at least one biasing element biases one or more of the motor and the clamping surface together, and the clamping surface and the motor clamp the stage platform therebetween.

Example 29 can include, or can optionally be combined with the subject matter of one or any combination of Examples 1 through 28 to optionally include wherein the at least one motor includes at least one piezo motor.

Example 30 can include, or can optionally be combined with the subject matter of one or any combination of Examples 1 through 29 to optionally include wherein the at least one biasing element includes a first spring and a second spring, and the at least one motor is positioned between the first and second springs.

Example 31 can include, or can optionally be combined with the subject matter of one or any combination of Examples 1 through 30 to optionally include wherein the at least one motor includes: a first motor element configured to move the stage platform in a first direction relative to the stage base, a second motor element configured to move the stage platform in a second direction relative to the stage base, wherein the second direction is opposed to the first direction, and a drive shoe coupled between the first and second motor elements, the drive shoe is movably engaged with one of the stage platform or the stage base.

Example 32 can include, or can optionally be combined with the subject matter of one or any combination of Examples 1 through 31 to optionally include wherein the at least one biasing element includes one or more springs, wherein the first and second motor elements are interposed between first and second spring contact points.

Example 33 can include, or can optionally be combined with the subject matter of one or any combination of Examples 1 through 32 to optionally include wherein the at least one motor includes at least two motors interposed between the stage platform and the stage base.

Example 34 can include, or can optionally be combined with the subject matter of one or any combination of Examples 1 through 33 to optionally include wherein the rotation stage includes: at least three motors spaced around the stage platform and movably coupled with a first surface of the stage platform, and the clamping surface is movably coupled along a second surface of the stage platform, the second surface is opposed to the first surface, and in a clamping configuration the at least three motors are engaged along the first surface and the clamping surface is engaged along the second surface.

Example 35 can include, or can optionally be combined with the subject matter of one or any combination of Examples 1 through 34 to optionally include wherein the stage platform includes a rotation flange extending around a perimeter of the stage platform, the rotation flange includes the first and second opposed surfaces, and the rotation flange is interposed between the clamping surface and the at least three motors.

Example 36 can include, or can optionally be combined with the subject matter of one or any combination of Examples 1 through 35 to optionally include wherein the tilt stage includes: at least two motors spaced around the stage platform and movably coupled with a first surface of the stage platform, and the clamping surface is movably coupled along a second surface of the stage platform, wherein the second surface is opposed to the first surface.

Example 37 can include, or can optionally be combined with the subject matter of one or any combination of Examples 1 through 36 to optionally include wherein the stage platform includes a tilt spindle including the first surface and the second surface, the first surface extends along an outer perimeter of the tilt spindle and the second surface extends along an inner perimeter of the tilt spindle, and in a clamping configuration the clamping surface is engaged along the second surface and the at least two motors are engaged along the first surface.

Example 38 can include, or can optionally be combined with the subject matter of one or any combination of Examples 1 through 37 to optionally include wherein the clamping surface includes an axle extending through the tilt spindle.

Example 39 can include, or can optionally be combined with the subject matter of one or any combination of Examples 1 through 38 to optionally include one or more lateral support biasing elements coupled with the at least one biasing element, and the one or more lateral support biasing elements constrains lateral deflection of the at least one biasing element.

Example 40 can include, or can optionally be combined with the subject matter of one or any combination of Examples 1 through 39 to optionally include wherein the at least one biasing element is coupled with the motor, and the at least one biasing element biases the motor toward the clamping surface with the stage platform therebetween.

Example 41 can include, or can optionally be combined with the subject matter of one or any combination of Examples 1 through 40 to optionally include one or more linear stages coupled with at least one of the rotation and tilt stages.

Example 42 can include, or can optionally be combined with the subject matter of one or any combination of Examples 1 through 41 to optionally include wherein the one or more linear stages includes a plurality of linear stages coupled in series with each other.

Example 43 can include, or can optionally be combined with the subject matter of one or any combination of Examples 1 through 42 to optionally include a testing assembly base coupled with the one or more linear stages.

Example 44 can include, or can optionally be combined with the subject matter of one or any combination of Examples 1 through 43 to optionally include wherein the tilt stage is directly coupled with the rotation stage, and the rotation stage is directly coupled with the one or more linear stages.

Example 45 can include, or can optionally be combined with the subject matter of one or any combination of Examples 1-44 to include, subject matter such as a method, such as can include moving a stage platform relative to a stage base with at least one motor; arresting motion of the stage platform; and statically clamping the stage platform relative to the stage base, wherein statically clamping includes: biasing a clamping surface and the at least one motor together, and engaging the stage platform between the clamping surface and the at least one motor.

Example 46 can include, or can optionally be combined with the subject matter of one or any combination of Examples 1 through 45 to optionally include wherein arresting motion of the stage platform includes relaxing the at least one motor.

Example 47 can include, or can optionally be combined with the subject matter of one or any combination of Examples 1 through 46 to optionally include wherein arresting motion of the stage platform automatically initiates static clamping of the stage platform.

Example 48 can include, or can optionally be combined with the subject matter of one or any combination of Examples 1 through 47 to optionally include wherein biasing the clamping surface and the at least one motor together includes biasing the at least one motor with at least one biasing element coupled with the at least one motor, and the at least one motor is biased toward the clamping surface.

Example 49 can include, or can optionally be combined with the subject matter of one or any combination of Examples 1 through 48 to optionally include wherein biasing the at least one motor includes: applying a first bias to a first motor element of the at least one motor with a first spring element of the at least one biasing element, and applying a second bias to a second motor element of the at least one motor with a second spring element of the at least one biasing element, wherein the first motor element is configured to move the stage platform in a first direction, and the second motor element is configured to move the stage platform in a second direction.

Example 50 can include, or can optionally be combined with the subject matter of one or any combination of Examples 1 through 49 to optionally include wherein moving the stage platform includes moving a drive shoe with one or more of first and second motor elements of the at least one motor, and the drive shoe is coupled between the first and second motor elements.

Example 51 can include, or can optionally be combined with the subject matter of one or any combination of Examples 1 through 50 to optionally include constraining lateral deflection of the at least one biasing element with at least one lateral support biasing element, wherein the at least one lateral support biasing element is coupled with the at least one biasing element.

Example 52 can include, or can optionally be combined with the subject matter of one or any combination of Examples 1 through 51 to optionally include wherein biasing the clamping surface and the at least one motor together includes biasing at least one motor positioned around the stage platform toward a first surface of the stage platform, and engaging the stage platform includes: engaging the at least one motor with the first surface, and engaging the clamping surface with a second surface of the stage platform opposed to the first surface.

Example 53 can include, or can optionally be combined with the subject matter of one or any combination of Examples 1 through 52 to optionally include wherein engaging the stage platform includes engaging a rotation flange of the stage platform, the rotation flange includes the first and second opposed surfaces.

Example 54 can include, or can optionally be combined with the subject matter of one or any combination of Examples 1 through 53 to optionally include wherein biasing the lamping surface and the at least one motor together includes biasing at least two motors spaced around the stage platform toward a first surface of the stage platform, and engaging the stage platform includes: engaging the at least two motors with the first surface, and engaging the clamping surface with a second surface of the stage platform opposed to the first surface.

Example 55 can include, or can optionally be combined with the subject matter of one or any combination of Examples 1 through 54 to optionally include wherein engaging the stage platform includes engaging a tilt spindle of the stage platform, the tilt spindle includes: the first surface extending along an outer perimeter of the tilt spindle, and the second surface extending along an inner perimeter of the tilt spindle.

Example 56 can include, or can optionally be combined with the subject matter of one or any combination of Examples 1 through 55 to optionally include wherein engaging the clamping surface with the second surface of the stage platform includes engaging an axle with the second surface of the tilt spindle.

Example 57 can include, or can optionally be combined with the subject matter of one or any combination of Examples 1-56 to include, subject matter such as an apparatus, such as can include a sample stage surface; a plurality of linear stages coupled in series and coupled with the sample stage surface, each of the plurality of linear stages includes: a stage base, a stage platform movably coupled with the stage base, and an actuator coupled with at least one of the stage base or stage platform, and the actuator is configured to move the stage platform relative to the stage base along a linear axis; and at least one cross roller bearing assembly interposed between the stage base and the stage platform of at least one of the plurality of linear stages, wherein the at least one cross roller bearing assembly includes a plurality of cylindrical bearings in an alternating crossed configuration, and each of the plurality of cylindrical bearings includes a cylindrical bearing surface engaged between opposed planar interface surfaces on the stage platform and the stage base.

Example 58 can include, or can optionally be combined with the subject matter of one or any combination of Examples 1 through 57 to optionally include wherein the plurality of linear stages includes three linear stages, and the linear axes of each of the stages are non-parallel, wherein:

with a first force vector applied to the plurality of linear stages the cross roller bearing assemblies of at least two linear stages of the three linear stages provide a first array of the opposed planar interface surfaces on the respective stage platforms and the stage bases engaged with the cylindrical bearing surfaces interposed therebetween, and with a second force vector applied to the plurality of linear stages the cross roller bearing assemblies of at least two linear stages of the three linear stages provide a second array of the opposed planar interface surfaces on the respective stage platforms and the stage bases engaged with the cylindrical bearing surfaces interposed therebetween, wherein the second force vector is non-parallel to the first force vector.

Example 59 can include, or can optionally be combined with the subject matter of one or any combination of Examples 1 through 58 to optionally include wherein the at least one cross roller bearing assembly includes: a first rail channel in the stage base, a second rail channel in the stage platform, the second rail channel is opposed to and aligned with the first rail channel, wherein the first and second rail channels include a first pair of opposed interface surfaces, and the first and second rail channels include a second pair of opposed interface surfaces, the second pair of opposed interface surfaces at an angle to the first pair of opposed interface surfaces, and the plurality of cylindrical bearings are arranged in the first and second rail channels with the cylindrical bearing surfaces in the alternating crossed configuration and engaged between the first and second pair of opposed interface surfaces.

Example 60 can include, or can optionally be combined with the subject matter of one or any combination of Examples 1 through 59 to optionally include wherein the first and second pairs of opposed interface surfaces are aligned with and extend parallel to the linear axis.

Example 61 can include, or can optionally be combined with the subject matter of one or any combination of Examples 1 through 60 to optionally include wherein the first and second pair of opposed interface surfaces extend around the plurality of cylindrical bearings.

Example 62 can include, or can optionally be combined with the subject matter of one or any combination of Examples 1 through 61 to optionally include wherein the at least one cross roller bearing assembly includes first and second cross roller bearing assemblies, and the actuator is positioned between the first and second cross roller bearing assemblies.

Example 63 can include, or can optionally be combined with the subject matter of one or any combination of Examples 1 through 62 to optionally include mechanical testing instrument coupled with a testing assembly platform, the testing assembly platform coupled with at least one of the plurality of linear stages, and the testing assembly platform is configured for coupling with a mounting stage of the multi-instrument assembly.

Example 64 can include, or can optionally be combined with the subject matter of one or any combination of Examples 1 through 63 to optionally include wherein two or more of the plurality of cylindrical bearings in the alternating crossed configuration are engaged with each other along adjacent cylindrical bearing surfaces, and the adjacent cylindrical bearing surfaces are orthogonal to each other.

Example 65 can include, or can optionally be combined with the subject matter of one or any combination of Examples 1 through 64 to optionally include wherein each of the plurality of cylindrical bearings includes planar end surfaces, the cylindrical bearing surfaces are interposed between the planar end surfaces, and a diameter of the planar end surfaces is greater than a length of the cylindrical bearing surfaces.

Example 66 can include, or can optionally be combined with the subject matter of one or any combination of Examples 1 through 65 to optionally include wherein the stage platform of one of linear stages of the plurality of linear stages includes the stage base of another of the linear stages of the plurality of linear stages.

Example 67 can include, or can optionally be combined with the subject matter of one or any combination of Examples 1 through 66 to optionally include wherein the actuator is fixed with one of the stage platform or the stage base, and the actuator moves with the stage platform or the stage base the actuator is fixed to.

Example 68 can include, or can optionally be combined with the subject matter of one or any combination of Examples 1-67 to include, subject matter such as a method, such as can include actuating one or more linear stages of a plurality of linear stages coupled with a sample stage surface, the one or more linear stages each include a stage platform movably coupled with a stage base along respective linear axes, and actuating includes moving at least one stage platform relative to at least one stage base along the respective linear axis; actuating the one or more linear stages includes aligning the sample stage surface with one or more instruments including a mechanical testing instrument; and constraining lateral translation and tilting of the stage platforms relative to the stage bases of the plurality of linear stages and relative to the linear axes with cross roller bearing assemblies interposed between one or more of the stage platforms and the stage bases, wherein the cross roller bearing assemblies include a plurality of cylindrical bearings in an alternating crossed configuration.

Example 69 can include, or can optionally be combined with the subject matter of one or any combination of Examples 1 through 68 to optionally include wherein constraining lateral translation and tilting includes: engaging platform planar interface surfaces of the stage platform with cylindrical bearing surfaces of the plurality of cylindrical bearings, and engaging base planar interface surfaces of the stage base with the cylindrical bearing surfaces of the plurality of cylindrical bearings.

Example 70 can include, or can optionally be combined with the subject matter of one or any combination of Examples 1 through 69 to optionally include wherein constraining lateral translation and tilting includes engaging opposed pairs of platform and base planar interface surfaces with cylindrical bearing surfaces of the plurality of cylindrical bearings with: a first array of cylindrical bearing surfaces engaged with a first pair of the opposed pairs of platform and base planar interface surfaces, and a second array of cylindrical bearing surfaces engaged with a second pair of the opposed pairs of platform and base planar interface surfaces, wherein the first pair of interface surfaces is at an angle to the second pair of interface surfaces corresponding to the alternating crossed configuration of the cylindrical bearings.

Example 71 can include, or can optionally be combined with the subject matter of one or any combination of Examples 1 through 70 to optionally include, wherein constraining lateral translation and tilting includes guiding the movement of at least one of the stage platforms relative to at least one of the respective stage bases along the respective linear axis of one of the linear stages of the plurality of linear stages with one of the cross roller bearing assemblies.

Example 72 can include, or can optionally be combined with the subject matter of one or any combination of Examples 1 through 71 to optionally include wherein aligning the sample stage surface with one or more instruments includes one or more of rotating or tilting the sample stage surface with one or more of rotation or tilt stages coupled with the plurality of linear stages.

Example 73 can include, or can optionally be combined with the subject matter of one or any combination of Examples 1-72 to include, subject matter such as a method, such as can include a modular instrument assembly comprising: a stage including: a stage base, a stage mount movably coupled with the stage base, the stage mount includes a stage interface profile configured for coupling with one or more mechanical testing instruments, and one or more actuators coupled with the stage mount, the one or more actuators are configured to move the stage mount relative to the stage base; and at least one mechanical testing assembly configured for coupling with the stage, the at least one mechanical testing assembly including: a mechanical testing instrument, and an instrument housing, wherein the instrument housing includes an instrument interface profile complementary to the stage interface profile, and the at least one mechanical testing assembly is removably coupled with the stage mount when the instrument interface profile is engaged with the stage interface profile.

Example 74 can include, or can optionally be combined with the subject matter of one or any combination of Examples 1 through 73 to optionally include one or more displacement sensors coupled between the stage base and the stage mount, wherein the one or more displacement sensors are configured to measure the displacement of the stage mount.

Example 75 can include, or can optionally be combined with the subject matter of one or any combination of Examples 1 through 74 to optionally include wherein the at least one mechanical testing assembly includes first and second mechanical testing assemblies and: the first mechanical testing assembly includes a first mechanical testing instrument and a first instrument interface profile complementary to the stage interface profile, and the second mechanical testing assembly includes a second mechanical testing instrument and a second instrument interface profile complementary to the stage interface profile.

Example 76 can include, or can optionally be combined with the subject matter of one or any combination of Examples 1 through 75 to optionally include a linear stage coupled with the flexural stage, the linear stage is configured to move the flexural stage and the at least one mechanical testing assembly.

Example 77 can include, or can optionally be combined with the subject matter of one or any combination of Examples 1 through 76 to optionally include wherein the flexural stage includes one or more springs coupled between the stage base and the stage mount, the one or more strings constrain movement of the stage mount to a uniaxial direction.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the inventors also contemplate examples in which only those elements shown or described are provided. Moreover, the inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A testing assembly configured for operation within a chamber of a multi-instrument assembly, each instrument of the multi-instrument assembly includes a working region, the working regions defining a localized coincidence region, the testing assembly comprising:
   a testing assembly platform configured for coupling with a mounting stage of the multi-instrument assembly, the testing assembly platform movable relative to the mounting stage;
   a mechanical deformation based testing instrument coupled with the testing assembly platform, the mechanical testing instrument is configured to engage and conduct deformation based testing on a sample on a sample stage surface;
   a multiple degree of freedom sample stage assembly coupled with the testing assembly platform, the multiple degree of freedom sample stage includes:
      the sample stage surface,
      a plurality of linear stages coupled in series with the testing assembly platform, and one or more of:
         a rotation stage, or
         a tilt stage, wherein the one or more rotation or tilt stages are coupled between the sample stage surface and the plurality of linear stages;
   wherein the multiple degree of freedom sample stage is configured to orient the sample stage surface within the localized coincidence region to each of the working regions in the localized coincidence region through a combination of movement of linear stages and one or more of rotation or tilt stages; and
   wherein in an installed configuration with the testing assembly platform coupled with the mounting stage of the multi-instrument assembly, the mechanical deformation based testing instrument and the multiple degree of freedom sample stage are recessed from walls of the multi-instrument assembly chamber, and movement of the testing assembly platform orients the mechanical deformation based testing instrument and the multiple degree of freedom sample stage assembly relative to the working regions.

2. The testing assembly of claim 1, wherein the rotation stage includes a rotation stage platform movably coupled with a rotation stage base, and the tilt stage includes a tilt stage platform movably coupled with a tilt stage base.

3. The testing assembly of claim 2 comprising a rotation and tilt assembly including the rotation and tilt stages, wherein the rotation and tilt assembly is coupled with the plurality of linear stages, and the rotation and tilt assembly includes:
   the rotation stage base coupled with the plurality of linear stages,
   a rotation spindle movably coupled with the rotation stage base, and the rotation spindle includes the rotation stage platform and the tilt stage base, and
   a tilt spindle movably coupled with the rotation spindle.

4. The testing assembly of claim 2, wherein at least one of the rotation stage and the tilt stage includes one or more motors, and each of the one or more motors includes:
   a first motor element configured to move one of the rotation stage platform or the tilt stage platform in a first direction relative to the respective rotation stage base or the tilt stage base,
   a second motor element configured to move one of the rotation stage platform or the tilt stage platform in second direction relative to the respective rotation stage base or the tilt stage base, wherein the second direction is opposed to the first direction, and
   a drive shoe coupled between the first and second motor elements, the drive shoe is movably engaged with one of the rotation or tilt stage platforms or the rotation or tilt stage bases.

5. The testing assembly of claim 1, wherein the multiple degree of freedom sample stage assembly is isolated from walls of a chamber of a multi-instrument assembly.

6. The testing assembly of claim 1, wherein the tilt stage includes a tilting range of motion, and the rotation stage includes a rotation range of motion, and the tilt and rotation stages are movable throughout the respective tilting and rotation ranges of motion while the sample stage surface is oriented to each of the working regions in the localized coincidence region.

7. A method for orienting a sample within a chamber of a multi-instrument assembly using a multiple degree of freedom sample stage assembly, the method comprising:
   orienting a sample on a sample stage surface to a first orientation in the chamber coincident with two or more working regions of two or more instruments within the chamber including a deformation based mechanical testing instrument, the two or more working regions define a localized coincidence region within the chamber, and the sample in the first orientation is within the localized coincidence region, orienting includes one or more of:
      tilting a tilt stage coupled with the sample stage surface, or
      rotating a rotation stage coupled with the sample stage surface;
   reorienting the sample on the sample stage surface to a second orientation in the chamber coincident with two or more working regions of the two or more instruments, the second orientation is different from the first orientation, and the sample in the second orientation is within the localized coincidence region, reorienting includes one or more of tilting the tilt stage or rotating the rotation stage; and
   wherein the sample stage surface, one or more of the rotation or tilt stages and the deformation based mechanical testing instrument are coupled with a testing assembly platform coupled to a mounting stage of the multi-instrument assembly, and the mounted testing assembly platform is recessed from walls of the multi-instrument assembly.

8. The method of claim 7, wherein orienting the sample on the sample stage surface to the first orientation includes one or more of:
   tilting a tilt stage coupled with the sample stage surface, or
   rotating a rotation stage coupled with the sample stage surface, and
   rotating the sample stage surface around a sample surface rotational axis extending through the sample stage surface; and
   reorienting the sample on the sample stage surface to the second orientation includes one or more of tilting the tilt stage or rotating the rotation stage, and rotating the rotation stage coupled with the sample stage surface.

9. A sample stage assembly of a testing assembly, the sample stage assembly comprising:
   a rotation stage;
   a tilt stage coupled with the rotation stage;
   a sample stage surface coupled with one of the rotation stage or the tilt stage; and wherein one or both of the rotation and tilt stages includes:
a stage base,
a stage platform coupled with the stage base, and
at least one motor movably coupled with one of the stage base or the stage platform, the at least one motor is configured to move the stage platform relative to the stage base;
wherein one or both of the rotation and tilt stages includes a clamping assembly, the clamping assembly comprising:
a clamping surface extending along the stage platform, and
at least one biasing element coupled with at least one of the motor and the clamping surface, wherein the at least one biasing element biases one or more of the motor and the clamping surface together, and the clamping surface and the motor clamp the stage platform therebetween;
a deformation based mechanical testing instrument; and
a testing assembly platform, the deformation based mechanical testing instrument, the rotation and tilt stages, and the sample stage surface are mounted on the testing assembly platform, and wherein the testing assembly platform is configured for actuation to orient each of the deformation based mechanical testing instrument, the rotation and tilt stages, and the sample stage surface relative to two or more instruments of a multi instrument assembly.

10. The sample stage assembly of claim 9, wherein the at least one motor includes at least one piezo motor.

11. The sample stage assembly of claim 9, wherein the rotation stage includes:
at least three motors spaced around the stage platform and movably coupled with a first surface of the stage platform, and
the clamping surface is movably coupled along a second surface of the stage platform, the second surface is opposed to the first surface, and in a clamping configuration the at least three motors are engaged along the first surface and the clamping surface is engaged along the second surface.

12. The sample stage assembly of claim 9, wherein the tilt stage includes:
at least two motors spaced around the stage platform and movably coupled with a first surface of the stage platform, and
the clamping surface is movably coupled along a second surface of the stage platform, wherein the second surface is opposed to the first surface.

13. The sample stage assembly of claim 9 comprising one or more linear stages coupled with at least one of the rotation and tilt stages.

14. A multiple degree of freedom sample stage assembly configured for operation within the chamber of a multi-instrument assembly, the multiple degree of freedom sample stage assembly comprises:
a sample stage surface;
a plurality of linear stages coupled in series and coupled with the sample stage surface, each of the plurality of linear stages includes:
a stage base,
a stage platform movably coupled with the stage base, and
an actuator coupled with at least one of the stage base or stage platform, and the actuator is configured to move the stage platform relative to the stage base along a linear axis; and
at least two cross roller bearing assembly assemblies interposed between the stage base and the stage platform of at least one of the plurality of linear stages, wherein the at least two cross roller bearing assembly assemblies includes a plurality of cylindrical bearings in an alternating crossed configuration, and each of the plurality of cylindrical bearings includes a cylindrical bearing surface engaged between opposed planar interface surfaces on the stage platform and the stage base; and
wherein the at least two cross roller bearing assemblies includes first and second cross roller bearing assemblies, and the actuator is positioned between the first and second cross roller bearing assemblies;
the multiple degree of freedom sample stage assembly further comprising a deformation based mechanical testing instrument coupled with a testing assembly platform, the testing assembly platform coupled with at least one of the plurality of linear stages, and the testing assembly platform is configured for coupling with a mounting stage of the multi-instrument assembly.

15. The multiple degree of freedom sample stage assembly of claim 14, wherein the plurality of linear stages includes three linear stages, and the linear axes of each of the stages are non-parallel, wherein:
with a first force vector applied to the plurality of linear stages the cross roller bearing assemblies of at least two linear stages of the three linear stages provide a first array of the opposed planar interface surfaces on the respective stage platforms and the stage bases engaged with the cylindrical beating surfaces interposed therebetween, and
with a second force vector applied to the plurality of linear stages the cross roller bearing assemblies of at least two linear stages of the three linear stages provide a second array of the opposed planar interface surfaces on the respective stage platforms and the stage bases engaged with the cylindrical beating surfaces interposed therebetween, wherein the second force vector is non-parallel to the first force vector.

16. A method for using a multiple degree of freedom sample stage comprising:
actuating one or more linear stages of a plurality of linear stages coupled with a sample stage surface, the one or more linear stages each include a stage platform movably coupled with a stage base along respective linear axes, and actuating includes moving at least one stage platform relative to at least one stage base along the respective linear axis;
actuating with an actuator the one or more linear stages includes aligning the sample stage surface with one or more instruments including a deformation based mechanical testing instrument; and
constraining lateral translation and tilting of the stage platforms relative to the stage bases of the plurality of linear stages and relative to the linear axes with two cross roller bearing assemblies interposed between one or more of the stage platforms and the stage bases, wherein the cross roller bearing assemblies include a plurality of cylindrical bearings in an alternating crossed configuration, and the actuator is positioned between the two cross roller bearing assemblies.

17. The method of claim 16, wherein aligning the sample stage surface with one or more instruments includes one or more of rotating or tilting the sample stage surface with one or more of rotation or tilt stages coupled with the plurality of linear stages.

18. A modular instrument assembly comprising:
a stage including:
  a stage base,
  a stage mount movably coupled with the stage base, the stage mount includes a stage interface profile configured for coupling with one or more mechanical testing instruments, and
  one or more actuators coupled with the stage mount, the one or more actuators are configured to move the stage mount relative to the stage base; and
at least one mechanical testing assembly configured for coupling with the stage, the at least one mechanical testing assembly including:
  a deformation based mechanical testing instrument coupled with the stage, and
  an instrument housing, wherein the instrument housing includes an instrument interface profile complementary to the stage interface profile, and the at least one mechanical testing assembly is removably coupled with the stage mount when the instrument interface profile is engaged with the stage interface profile.

19. The modular instrument assembly of claim 18 comprising one or more displacement sensors coupled between the stage base and the stage mount, wherein the one or more displacement sensors are configured to measure the displacement of the stage mount.

20. The method of claim 7 comprising moving the testing assembly platform including the sample stage surface, one or more of the rotation or tilt stages and the deformation based mechanical testing instrument relative to at least one of the working regions.

* * * * *